US007442767B2

(12) United States Patent
Franco

(10) Patent No.: US 7,442,767 B2
(45) Date of Patent: Oct. 28, 2008

(54) $\alpha_{1D}$ CALCIUM CHANNEL EXPRESSED IN ATRIUM

(75) Inventor: Rodrigo Franco, Westford, MA (US)

(73) Assignee: Wyeth, Madison, NJ (US)

( * ) Notice: Subject to any disclaimer, the term of this patent is extended or adjusted under 35 U.S.C. 154(b) by 394 days.

(21) Appl. No.: 10/875,892

(22) Filed: Jun. 23, 2004

(65) Prior Publication Data
US 2005/0042723 A1 Feb. 24, 2005

Related U.S. Application Data

(60) Provisional application No. 60/480,949, filed on Jun. 23, 2003.

(51) Int. Cl.
*C07K 14/435* (2006.01)
*C07K 14/705* (2006.01)
*C12P 21/02* (2006.01)
*A61K 38/17* (2006.01)
(52) U.S. Cl. .............................. 530/350; 514/2; 514/12; 536/23.5; 435/69.1
(58) Field of Classification Search ....................... None
See application file for complete search history.

(56) References Cited

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 492-495.*
Skolnick et al. (2000). From genes to protein structure and function: novel applications of computational approaches in the genomic era. Trends in Biotech. 18(1):34-39.*
Bork, A. (2000). Powers and pitfalls in sequence analysis: the 70% hurdle. Genome Res. 10:398-400.*
Doerks et al. (1998). Protein annotation: detective work for function prediction. Trends in Genetics. 14(6):248-250.*
Smith et al. (1997). The challenges of genome sequence annotation or the devil is in the details. Nature Biotech. 15:1222-1223.*
Brenner, S.E. (1999). Errors in genome function. Trends in Genetics. 15(4):132-133.*
Bork et al. (1996). Go hunting in sequence databases but watch out for the traps. Trends in Genetics. 12(10):425-427.*
Platzer, Josef, et al. (Jul. 7, 2000). *Cell*. Congenital Deafness and Sinoactrial Node Dysfunction in Mice Lacking Class D L-Type $Ca^{2+}$ Channels. vol. 102, 89-97.
Catterall, William A., et al. (2000). *Annu. Rev. Cell Dev. Biol.* Structure and Regulation of Voltage-Gated $Ca^{2+}$ Channels. 16:521-55.
Zhang, Zhao, et al. (2002). *Cellular Biology*. Functional Roles of $Ca_v1.3$ ($\alpha_{1D}$) Calcium Channel in Sinoatrial Nodes—Insight Gained Using Gene-Targeted Null Mutant Mice. 90:981-987.
Mangoni, Matteo E. et al. (Apr. 29, 2003). *PNAS*. Funtional role of L-type $Ca_v1.3$ $Ca^{2+}$ channels in cardiac pacemaker activity. vol. 100, No. 9, 5543-5548.
Kamp, Timothy J., et al. (2002). *Circulation Research Journal of the American Heart Association*. L-Type $Ca^{2+}$ Channels Gaining Respect in Heart Failure. 91:451-453.
Xiao, Guang-Qian, et al. (2001). *Circulation Journal of the American Heart Association*. Direct Inhibition of Expressed Cardiac L- and T-Type Calcium Channels by IgG from Mothers Whose Children Have Congenital Heart Block. 103:1599-1604.
Takimoto, Koichi, et al. (Apr. 1997). *J Moll Cell Cardiol*. Distribution, Splicing and Glucocorticoid-Induced Expression of Cardiac $\alpha_{1C}$ and $\alpha_{1D}$ Voltage-gated $Ca^{2+}$ Channels mRNAs. 29:3035-3042.

* cited by examiner

*Primary Examiner*—Chrstine J Saoud
*Assistant Examiner*—Jon M Lockard
(74) *Attorney, Agent, or Firm*—Joseph E. Zahner

(57) ABSTRACT

Novel calcium channel nucleic acids and polypeptides are disclosed herein. Methods of using the novel nucleic acids and polypeptides are also disclosed.

3 Claims, No Drawings

SEQUENCE LISTING

<160> NUMBER OF SEQ ID NOS: 10

<210> SEQ ID NO 1
<211> LENGTH: 12

```
<212> TYPE: DNA
<213> ORGANISM: Homo sapiens

<400> SEQUENCE: 1
aaaattgtag cg                                                         12

<210> SEQ ID NO 2
<211> LENGTH: 4
<212> TYPE: PRT
<213> ORGANISM: Homo sapiens

<400> SEQUENCE: 2

Lys Ile Val Ala
  1

<210> SEQ ID NO 3
<211> LENGTH: 6426
<212> TYPE: DNA
<213> ORGANISM: Homo sapiens

<400> SEQUENCE: 3
atgatgatga tgatgatgat gaaaaaaatg cagcatcaac ggcagcagca agcggaccac        60
gcgaacgagg caaactatgc aagaggcacc agacttcctc tttctggtga aggaccaact       120
tctcagccga atagctccaa gcaaactgtc ctgtcttggc aagctgcaat cgatgctgct       180
agacaggcca aggctgccca aactatgagc acctctgcac ccccacctgt aggatctctc       240
tcccaaagaa aacgtcagca atacgccaag agcaaaaaac agggtaactc gtccaacagc       300
cgacctgccc gcgcccttt ctgtttatca ctcaataacc ccatccgaag agcctgcatt        360
agtatagtgg aatggaaacc atttgacata tttatattat tggctatttt tgccaattgt       420
gtggccttag ctatttacat cccattccct gaagatgatt ctaattcaac aaatcataac       480
ttggaaaaag tagaatatgc cttcctgatt attttttacag tcgagacatt tttgaagatt       540
atagcgtatg gattattgct acatcctaat gcttatgtta ggaatggatg gaatttactg       600
gattttgtta tagtaatagt aggattgttt agtgtaattt tggaacaatt aaccaaagaa       660
acagaaggcg ggaaccactc aagcggcaaa tctggaggct ttgatgtcaa agccctccgt       720 gccttcgag tgttgcgacc acttcgacta gtgtcaggag tgcccagttt acaagttgtc        780
ctgaactcca ttataaaagc catggttccc ctccttcaca tagccctttt ggtattattt       840
gtaatcataa tctatgctat tataggattg gaacttttta ttggaaaaat gcacaaaaca       900
tgtttttttg ctgactcaga tatcgtagct gaagaggacc cagctccatg tgcgttctca       960
gggaatggac gccagtgtac tgccaatggc acggaatgta gagtggctg ggttggcccg       1020 aacggaggca tcaccaactt tgataacttt gcctttgcca tgcttactgt gtttcagtgc       1080
atcaccatgg agggctggac agacgtgctc tactggatga atgatgctat gggatttgaa       1140
ttgccctggg tgtattttgt cagtctcgtc atctttgggt cattttcgt actaaatctt       1200 gtacttggtg tattgagcgg agaattctca aaggaaagag agaaggcaaa agcacgggga       1260
gatttccaga agctccggga gaagcagcag ctggaggagg atctaaaggg ctacttggat       1320
tggatcaccc aagctgagga catcgatccg gagaatgagg aagaaggagg agaggaaggc       1380
aaacgaaata ctagcatgcc caccagcgag actgagtctg tgaacacaga gaacgtcagc       1440
ggtgaaggcg agaaccgagg ctgctgtgga agtctctgtc aagccatctc aaaatccaaa       1500
ctcagccgac gctggcgtcg ctggaaccga ttcaatcgca agaagatgtag ggccgccgtg       1560 aagtctgtca cgtttactg ctggttatc gtcctggtgt ttctgaacac cttaaccatt       1620
```

```
tcctctgagc actacaatca gccagattgg ttgacacaga ttcaagatat tgccaacaaa    1680
gtcctcttgg ctctgttcac ctgcgagatg ctggtaaaaa tgtacagctt gggcctccaa    1740
gcatatttcg tctctctttt caaccggttt gattgcttcg tggtgtgtgg tggaatcact    1800
gagacgatct tggtggaact ggaaatcatg tctcccctgg ggatctctgt gtttcggtgt    1860
gtgcgcctct taagaatctt caaagtgacc aggcactgga cttccctgtg caacttagtg    1920
gcatccttat taaactccat gaagtccagt gcttcgctgt tgcttctgct ttttctcttc    1980
attatcatct tttccttgct tgggatgcag ctgtttggcg gcaagtttaa ttttgatgaa    2040
acgcaaacca agcggagcac ctttgacaat ttccctcaag cacttctcac agtgttccag    2100
atcctgacag gcgaagactg gaatgctgtg atgtacgatg gcatcatggc ttacgggggc    2160
ccatcctctt caggaatgat cgtctgcatc tacttcatca tcctcttcat ttgtggtaac    2220
tatattctac tgaatgtctt cttggccatc gctgtagaca atttggctga tgctgaaagt    2280
ctgaacactg ctcagaaaga agaagcggaa gaaaaggaga ggaaaaagat tgccagaaaa    2340
gagagcctag aaaataaaaa gaacaacaaa ccagaagtca accagatagc caacagtgac    2400
aacaaggtta caattgatga ctatagagaa gaggatgaag acaaggaccc ctatccgcct    2460
tgcgatgtgc cagtagggga agaggaagag gaagaggagg aggatgaacc tgaggttcct    2520
gccggacccc gtcctcgaag gatctcggag ttgaacatga aggaaaaaat tgcccccatc    2580
cctgaaggga gcgctttctt cattcttagc aagaccaacc cgatccgcgt aggctgccac    2640
aagctcatca ccaccacat cttcaccaac ctcatccttg tcttcatcat gctgagcagt    2700
gctgccctgg ccgcagagga ccccatccgc agccactcct tccggaacac gatactgggt    2760
tactttgact atgccttcac agccatcttt actgttgaga tcctgttgaa gatgacaact    2820
tttggagctt cctccacaa aggggccttc tgcaggaact acttcaattt gctggatatg    2880
ctggtggttg gggtgtctct ggtgtcattt gggattcaat ccagtgccat ctccgttgtg    2940
aagattctga gggtcttaag ggtcctgcgt cccctcaggg ccatcaacag agcaaaagga    3000
cttaagcacg tggtccagtg cgtcttcgtg gccatccgga ccatcggcaa catcatgatc    3060
gtcaccaccc tcctgcagtt catgtttgcc tgtatcgggg tccagttgtt caaggggaag    3120
ttctatcgct gtacgatga agccaaaagt aaccctgaag aatgcagggg acttttcatc    3180
ctctacaagg atggggatgt tgacagtcct gtggtccgtg aacggatctg gcaaaacagt    3240
gatttcaact tcgacaacgt cctctctgct atgatggcgc tcttcacagt ctccacgttt    3300
gagggctggc ctgcgttgct gtataaagcc atcgactcga atggagagaa catcggccca    3360
atctacaacc accgcgtgga gatctccatc ttcttcatca tctacatcat cattgtagct    3420
ttcttcatga tgaacatctt tgtgggcttt gtcatcgtta catttcagga acaaggagaa    3480
aaagagtata agaactgtga gctggacaaa aatcagcgtc agtgtgttga atacgccttg    3540
aaagcacgtc ccttgcggag atacatcccc aaaaaccct accagtacaa gttctggtac    3600
gtggtgaact cttcgccttt cgaatacatg atgtttgtcc tcatcatgct caacacactc    3660
tgcttggcca tgcagcacta cgagcagtcc aagatgttca atgatgccat ggacattctg    3720
aacatggtct tcaccggggt gttcaccgtc gagatggttt tgaaagtcat cgcatttaag    3780
cctaaggggt attttagtga cgcctggaac acgtttgact ccctcatcgt aatcggcagc    3840
attatagacg tggccctcag cgaagcgac aaaattgtag cgaactctga agagagcaat    3900
agaatctcca tcacctttt ccgtcttttc cgagtgatgc gattggtgaa gcttctcagc    3960
```

```
aggggggaag gcatccggac attgctgtgg acttttatta agttctttca ggcgctcccg    4020
tatgtggccc tcctcatagc catgctgttc ttcatctatg cggtcattgg catgcagatg    4080
tttgggaaag ttgccatgag agataacaac cagatcaata ggaacaataa cttccagacg    4140
tttccccagg cggtgctgct gctcttcagg tgtgcaacag gtgaggcctg gcaggagatc    4200
atgctggcct gtctcccagg gaagctctgt gaccctgagt cagattacaa ccccggggag    4260
gagcatacat gtgggagcaa ctttgccatt gtctatttca tcagttttta catgctctgt    4320
gcatttctga tcatcaatct gtttgtggct gtcatcatgg ataatttcga ctatctgacc    4380
cgggactggt ctattttggg gcctcaccat ttagatgaat caaaagaat atggtcagaa     4440
tatgaccctg aggcaaaggg aaggataaaa caccttgatg tggtcactct gcttcgacgc    4500
atccagcctc ccctggggtt tgggaagtta tgtccacaca gggtagcgtg caagagatta    4560
gttgccatga acatgcctct caacagtgac gggacagtca tgtttaatgc aaccctgttt    4620
gctttggttc gaacggctct taagatcaag accgaaggga acctggagca agctaatgaa    4680
gaacttcggg ctgtgataaa gaaaatttgg aagaaaacca gcatgaaatt acttgaccaa    4740
gttgtccctc cagctggtga tgatgaggta accgtgggga agttctatgc cactttcctg    4800
atacaggact actttaggaa attcaagaaa cggaaagaac aaggactggt gggaaagtac    4860
cctgcgaaga caccacaat tgccctacag gcgggattaa ggacactgca tgacattggg     4920
ccagaaatcc ggcgtgctat atcgtgtgat ttgcaagatg acgagcctga ggaaacaaaa    4980
cgagaagaag aagatgatgt gttcaaaaga aatggtgccc tgcttggaaa ccatgtcaat    5040
catgttaata gtgataggag agattccctt cagcagacca ataccaccca ccgtcccctg    5100
catgtccaaa ggccttcaat tccacctgca agtgatactg agaaaccgct gtttcctcca    5160
gcaggaaatt cggtgtgtca taaccatcat aaccataatt ccataggaaa gcaagttccc    5220
acctcaacaa atgccaatct caataatgcc aatatgtcca aagctgccca tggaaagcgg    5280
cccagcattg ggaaccttga gcatgtgtct gaaaatgggc atcattcttc ccacaagcat    5340
gaccgggagc ctcagagaag gtccagtgtg aaaaggtccg actcaggaga tgaacagctc    5400
ccaactattt gccgggaaga cccagagata catggctatt tcagggaccc ccactgcttg    5460
ggggagcagg agtatttcag tagtgaggaa tgctacgagg atgacagctc gcccacctgg    5520
agcaggcaaa actatggcta ctacagcaga tacccaggca gaaacatcga ctctgagagg    5580
ccccgaggct accatcatcc ccaaggattc ttggaggacg atgactcgcc cgtttgctat    5640
gattcacgga gatctccaag gagacgccta ctacctccca ccccagcatc ccaccggaga    5700
tcctccttca ctttgagtg cctgcgccgg cagagcagcc aggaagaggt cccgtcgtct    5760
cccatcttcc cccatcgcac ggccctgcct ctgcatctaa tgcagcaaca gatcatggca    5820
gttgccggcc tagattcaag taaagcccag aagtactcac cgagtcactc gacccggtcg    5880
tgggccaccc ctccagcaac ccctccctac cgggactgga caccgtgcta cacccccctg    5940
atccaagtgg agcagtcaga ggccctggac caggtgaacg gcagcctgcc gtccctgcac    6000
cgcagctcct ggtacacaga cgagcccgac atctcctacc ggactttcac accagccagc    6060
ctgactgtcc ccagcagctt ccggaacaaa acagcgaca agcagaggag tgcggacagc    6120
ttggtggagg cagtcctgat atccgaaggc ttggacgct atgcaaggga cccaaaattt    6180
gtgtcagcaa caaaacacga aatcgctgat gcctgtgacc tcaccatcga cgagatggag    6240
agtgcagcca gcaccctgct taatgggaac gtgcgtcccc gagccaacgg ggatgtgggc    6300
cccctctcac accggcagga ctatgagcta caggactttg gtcctggcta cagcgacgaa    6360
```

-continued

```
gagccagacc ctgggaggga tgaggaggac ctggcggatg aaatgatatg catcaccacc    6420
ttgtag                                                                6426
```

<210> SEQ ID NO 4
<211> LENGTH: 2141
<212> TYPE: PRT
<213> ORGANISM: Homo sapiens

<400> SEQUENCE: 4

```
Met Met Met Met Met Met Lys Lys Met Gln His Gln Arg Gln Gln
1               5                   10                  15

Gln Ala Asp His Ala Asn Glu Ala Asn Tyr Ala Arg Gly Thr Arg Leu
            20                  25                  30

Pro Leu Ser Gly Glu Gly Pro Thr Ser Gln Pro Asn Ser Ser Lys Gln
        35                  40                  45

Thr Val Leu Ser Trp Gln Ala Ala Ile Asp Ala Ala Arg Gln Ala Lys
    50                  55                  60

Ala Ala Gln Thr Met Ser Thr Ser Ala Pro Pro Val Gly Ser Leu
65                  70                  75                  80

Ser Gln Arg Lys Arg Gln Gln Tyr Ala Lys Ser Lys Lys Gln Gly Asn
                85                  90                  95

Ser Ser Asn Ser Arg Pro Ala Arg Ala Leu Phe Cys Leu Ser Leu Asn
            100                 105                 110

Asn Pro Ile Arg Arg Ala Cys Ile Ser Ile Val Glu Trp Lys Pro Phe
        115                 120                 125

Asp Ile Phe Ile Leu Leu Ala Ile Phe Ala Asn Cys Val Ala Leu Ala
    130                 135                 140

Ile Tyr Ile Pro Phe Pro Glu Asp Asp Ser Asn Ser Thr Asn His Asn
145                 150                 155                 160

Leu Glu Lys Val Glu Tyr Ala Phe Leu Ile Ile Phe Thr Val Glu Thr
                165                 170                 175

Phe Leu Lys Ile Ile Ala Tyr Gly Leu Leu Leu His Pro Asn Ala Tyr
            180                 185                 190

Val Arg Asn Gly Trp Asn Leu Leu Asp Phe Val Ile Val Val Gly
        195                 200                 205

Leu Phe Ser Val Ile Leu Glu Gln Leu Thr Lys Glu Thr Glu Gly Gly
    210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
                245                 250                 255

Leu Gln Val Val Leu Asn Ser Ile Ile Lys Ala Met Val Pro Leu Leu
            260                 265                 270

His Ile Ala Leu Leu Val Leu Phe Val Ile Ile Tyr Ala Ile
        275                 280                 285

Gly Leu Glu Leu Phe Ile Gly Lys Met His Lys Thr Cys Phe Phe Ala
    290                 295                 300

Asp Ser Asp Ile Val Ala Glu Glu Asp Pro Ala Pro Cys Ala Phe Ser
305                 310                 315                 320

Gly Asn Gly Arg Gln Cys Thr Ala Asn Gly Thr Glu Cys Arg Ser Gly
                325                 330                 335

Trp Val Gly Pro Asn Gly Gly Ile Thr Asn Phe Asp Asn Phe Ala Phe
            340                 345                 350
```

-continued

```
Ala Met Leu Thr Val Phe Gln Cys Ile Thr Met Glu Gly Trp Thr Asp
            355                 360                 365
Val Leu Tyr Trp Met Asn Asp Ala Met Gly Phe Glu Leu Pro Trp Val
        370                 375                 380
Tyr Phe Val Ser Leu Val Ile Phe Gly Ser Phe Val Leu Asn Leu
385                 390                 395                 400
Val Leu Gly Val Leu Ser Gly Glu Phe Ser Lys Glu Arg Glu Lys Ala
                405                 410                 415
Lys Ala Arg Gly Asp Phe Gln Lys Leu Arg Glu Lys Gln Gln Leu Glu
            420                 425                 430
Glu Asp Leu Lys Gly Tyr Leu Asp Trp Ile Thr Gln Ala Glu Asp Ile
        435                 440                 445
Asp Pro Glu Asn Glu Glu Gly Gly Glu Gly Lys Arg Asn Thr
    450                 455                 460
Ser Met Pro Thr Ser Glu Thr Glu Ser Val Asn Thr Glu Asn Val Ser
465                 470                 475                 480
Gly Glu Gly Glu Asn Arg Gly Cys Cys Gly Ser Leu Cys Gln Ala Ile
                485                 490                 495
Ser Lys Ser Lys Leu Ser Arg Arg Trp Arg Arg Trp Asn Arg Phe Asn
            500                 505                 510
Arg Arg Arg Cys Arg Ala Ala Val Lys Ser Val Thr Phe Tyr Trp Leu
        515                 520                 525
Val Ile Val Leu Val Phe Leu Asn Thr Leu Thr Ile Ser Ser Glu His
    530                 535                 540
Tyr Asn Gln Pro Asp Trp Leu Thr Gln Ile Gln Asp Ile Ala Asn Lys
545                 550                 555                 560
Val Leu Leu Ala Leu Phe Thr Cys Glu Met Leu Val Lys Met Tyr Ser
                565                 570                 575
Leu Gly Leu Gln Ala Tyr Phe Val Ser Leu Phe Asn Arg Phe Asp Cys
            580                 585                 590
Phe Val Val Cys Gly Gly Ile Thr Glu Thr Ile Leu Val Glu Leu Glu
        595                 600                 605
Ile Met Ser Pro Leu Gly Ile Ser Val Phe Arg Cys Val Arg Leu Leu
    610                 615                 620
Arg Ile Phe Lys Val Thr Arg His Trp Thr Ser Leu Cys Asn Leu Val
625                 630                 635                 640
Ala Ser Leu Leu Asn Ser Met Lys Ser Ser Ala Ser Leu Leu Leu Leu
                645                 650                 655
Leu Phe Leu Phe Ile Ile Ile Phe Ser Leu Leu Gly Met Gln Leu Phe
            660                 665                 670
Gly Gly Lys Phe Asn Phe Asp Glu Thr Gln Thr Lys Arg Ser Thr Phe
        675                 680                 685
Asp Asn Phe Pro Gln Ala Leu Leu Thr Val Phe Gln Ile Leu Thr Gly
    690                 695                 700
Glu Asp Trp Asn Ala Val Met Tyr Asp Gly Ile Met Ala Tyr Gly Gly
705                 710                 715                 720
Pro Ser Ser Ser Gly Met Ile Val Cys Ile Tyr Phe Ile Ile Leu Phe
                725                 730                 735
Ile Cys Gly Asn Tyr Ile Leu Leu Asn Val Phe Leu Ala Ile Ala Val
            740                 745                 750
Asp Asn Leu Ala Asp Ala Glu Ser Leu Asn Thr Ala Gln Lys Glu Glu
        755                 760                 765
Ala Glu Glu Lys Glu Arg Lys Lys Ile Ala Arg Lys Glu Ser Leu Glu
```

-continued

```
            770                 775                 780
Asn Lys Lys Asn Asn Lys Pro Glu Val Asn Gln Ile Ala Asn Ser Asp
785                 790                 795                 800

Asn Lys Val Thr Ile Asp Asp Tyr Arg Glu Glu Asp Glu Asp Lys Asp
                805                 810                 815

Pro Tyr Pro Pro Cys Asp Val Pro Val Gly Glu Glu Glu Glu Glu Glu
                820                 825                 830

Glu Asp Glu Pro Glu Val Pro Ala Gly Pro Arg Pro Arg Arg Ile
                835                 840                 845

Ser Glu Leu Asn Met Lys Glu Lys Ile Ala Pro Ile Pro Glu Gly Ser
850                 855                 860

Ala Phe Phe Ile Leu Ser Lys Thr Asn Pro Ile Arg Val Gly Cys His
865                 870                 875                 880

Lys Leu Ile Asn His His Ile Phe Thr Asn Leu Ile Leu Val Phe Ile
                885                 890                 895

Met Leu Ser Ser Ala Ala Leu Ala Ala Glu Asp Pro Ile Arg Ser His
                900                 905                 910

Ser Phe Arg Asn Thr Ile Leu Gly Tyr Phe Asp Tyr Ala Phe Thr Ala
                915                 920                 925

Ile Phe Thr Val Glu Ile Leu Leu Lys Met Thr Thr Phe Gly Ala Phe
                930                 935                 940

Leu His Lys Gly Ala Phe Cys Arg Asn Tyr Phe Asn Leu Leu Asp Met
945                 950                 955                 960

Leu Val Val Gly Val Ser Leu Val Ser Phe Gly Ile Gln Ser Ser Ala
                965                 970                 975

Ile Ser Val Val Lys Ile Leu Arg Val Leu Arg Val Leu Arg Pro Leu
                980                 985                 990

Arg Ala Ile Asn Arg Ala Lys Gly Leu Lys His Val Val Gln Cys Val
                995                 1000                1005

Phe Val Ala Ile Arg Thr Ile Gly Asn Ile Met Ile Val Thr Thr Leu
                1010                1015                1020

Leu Gln Phe Met Phe Ala Cys Ile Gly Val Gln Leu Phe Lys Gly Lys
1025                1030                1035                1040

Phe Tyr Arg Cys Thr Asp Glu Ala Lys Ser Asn Pro Glu Glu Cys Arg
                1045                1050                1055

Gly Leu Phe Ile Leu Tyr Lys Asp Gly Asp Val Asp Ser Pro Val Val
                1060                1065                1070

Arg Glu Arg Ile Trp Gln Asn Ser Asp Phe Asn Phe Asp Asn Val Leu
                1075                1080                1085

Ser Ala Met Met Ala Leu Phe Thr Val Ser Thr Phe Glu Gly Trp Pro
                1090                1095                1100

Ala Leu Leu Tyr Lys Ala Ile Asp Ser Asn Gly Glu Asn Ile Gly Pro
1105                1110                1115                1120

Ile Tyr Asn His Arg Val Glu Ile Ser Ile Phe Phe Ile Ile Tyr Ile
                1125                1130                1135

Ile Ile Val Ala Phe Phe Met Met Asn Ile Phe Val Gly Phe Val Ile
                1140                1145                1150

Val Thr Phe Gln Glu Gln Gly Glu Lys Glu Tyr Lys Asn Cys Glu Leu
                1155                1160                1165

Asp Lys Asn Gln Arg Gln Cys Val Glu Tyr Ala Leu Lys Ala Arg Pro
                1170                1175                1180

Leu Arg Arg Tyr Ile Pro Lys Asn Pro Tyr Gln Tyr Lys Phe Trp Tyr
1185                1190                1195                1200
```

```
Val Val Asn Ser Ser Pro Phe Glu Tyr Met Met Phe Val Leu Ile Met
            1205                1210                1215

Leu Asn Thr Leu Cys Leu Ala Met Gln His Tyr Glu Gln Ser Lys Met
        1220                1225                1230

Phe Asn Asp Ala Met Asp Ile Leu Asn Met Val Phe Thr Gly Val Phe
    1235                1240                1245

Thr Val Glu Met Val Leu Lys Val Ile Ala Phe Lys Pro Lys Gly Tyr
1250                1255                1260

Phe Ser Asp Ala Trp Asn Thr Phe Asp Ser Leu Ile Val Ile Gly Ser
1265                1270                1275                1280

Ile Ile Asp Val Ala Leu Ser Glu Ala Asp Lys Ile Val Ala Asn Ser
            1285                1290                1295

Glu Glu Ser Asn Arg Ile Ser Ile Thr Phe Phe Arg Leu Phe Arg Val
        1300                1305                1310

Met Arg Leu Val Lys Leu Leu Ser Arg Gly Glu Gly Ile Arg Thr Leu
    1315                1320                1325

Leu Trp Thr Phe Ile Lys Phe Phe Gln Ala Leu Pro Tyr Val Ala Leu
1330                1335                1340

Leu Ile Ala Met Leu Phe Phe Ile Tyr Ala Val Ile Gly Met Gln Met
1345                1350                1355                1360

Phe Gly Lys Val Ala Met Arg Asp Asn Asn Gln Ile Asn Arg Asn Asn
            1365                1370                1375

Asn Phe Gln Thr Phe Pro Gln Ala Val Leu Leu Leu Phe Arg Cys Ala
        1380                1385                1390

Thr Gly Glu Ala Trp Gln Glu Ile Met Leu Ala Cys Leu Pro Gly Lys
    1395                1400                1405

Leu Cys Asp Pro Glu Ser Asp Tyr Asn Pro Gly Glu Glu His Thr Cys
    1410                1415                1420

Gly Ser Asn Phe Ala Ile Val Tyr Phe Ile Ser Phe Tyr Met Leu Cys
1425                1430                1435                1440

Ala Phe Leu Ile Ile Asn Leu Phe Val Ala Val Ile Met Asp Asn Phe
            1445                1450                1455

Asp Tyr Leu Thr Arg Asp Trp Ser Ile Leu Gly Pro His His Leu Asp
        1460                1465                1470

Glu Phe Lys Arg Ile Trp Ser Glu Tyr Asp Pro Glu Ala Lys Gly Arg
    1475                1480                1485

Ile Lys His Leu Asp Val Val Thr Leu Leu Arg Arg Ile Gln Pro Pro
    1490                1495                1500

Leu Gly Phe Gly Lys Leu Cys Pro His Arg Val Ala Cys Lys Arg Leu
1505                1510                1515                1520

Val Ala Met Asn Met Pro Leu Asn Ser Asp Gly Thr Val Met Phe Asn
            1525                1530                1535

Ala Thr Leu Phe Ala Leu Val Arg Thr Ala Leu Lys Ile Lys Thr Glu
        1540                1545                1550

Gly Asn Leu Glu Gln Ala Asn Glu Glu Leu Arg Ala Val Ile Lys Lys
    1555                1560                1565

Ile Trp Lys Lys Thr Ser Met Lys Leu Leu Asp Gln Val Val Pro Pro
    1570                1575                1580

Ala Gly Asp Asp Glu Val Thr Val Gly Lys Phe Tyr Ala Thr Phe Leu
1585                1590                1595                1600

Ile Gln Asp Tyr Phe Arg Lys Phe Lys Lys Arg Lys Glu Gln Gly Leu
            1605                1610                1615
```

-continued

```
Val Gly Lys Tyr Pro Ala Lys Asn Thr Thr Ile Ala Leu Gln Ala Gly
            1620                1625                1630

Leu Arg Thr Leu His Asp Ile Gly Pro Glu Ile Arg Arg Ala Ile Ser
        1635                1640                1645

Cys Asp Leu Gln Asp Asp Glu Pro Glu Thr Lys Arg Glu Glu
    1650                1655                1660

Asp Asp Val Phe Lys Arg Asn Gly Ala Leu Leu Gly Asn His Val Asn
1665                1670                1675                1680

His Val Asn Ser Asp Arg Arg Asp Ser Leu Gln Gln Thr Asn Thr Thr
            1685                1690                1695

His Arg Pro Leu His Val Gln Arg Pro Ser Ile Pro Ala Ser Asp
        1700                1705                1710

Thr Glu Lys Pro Leu Phe Pro Pro Ala Gly Asn Ser Val Cys His Asn
    1715                1720                1725

His His Asn His Asn Ser Ile Gly Lys Gln Val Pro Thr Ser Thr Asn
1730                1735                1740

Ala Asn Leu Asn Asn Ala Asn Met Ser Lys Ala Ala His Gly Lys Arg
1745                1750                1755                1760

Pro Ser Ile Gly Asn Leu Glu His Val Ser Glu Asn Gly His His Ser
            1765                1770                1775

Ser His Lys His Asp Arg Glu Pro Gln Arg Arg Ser Ser Val Lys Arg
        1780                1785                1790

Ser Asp Ser Gly Asp Glu Gln Leu Pro Thr Ile Cys Arg Glu Asp Pro
    1795                1800                1805

Glu Ile His Gly Tyr Phe Arg Asp Pro His Cys Leu Gly Glu Gln Glu
    1810                1815                1820

Tyr Phe Ser Ser Glu Glu Cys Tyr Glu Asp Ser Ser Pro Thr Trp
1825                1830                1835                1840

Ser Arg Gln Asn Tyr Gly Tyr Tyr Ser Arg Tyr Pro Gly Arg Asn Ile
            1845                1850                1855

Asp Ser Glu Arg Pro Arg Gly Tyr His His Pro Gln Gly Phe Leu Glu
        1860                1865                1870

Asp Asp Asp Ser Pro Val Cys Tyr Asp Ser Arg Arg Ser Pro Arg Arg
    1875                1880                1885

Arg Leu Leu Pro Pro Thr Pro Ala Ser His Arg Ser Ser Phe Asn
    1890                1895                1900

Phe Glu Cys Leu Arg Arg Gln Ser Ser Gln Glu Glu Val Pro Ser Ser
1905                1910                1915                1920

Pro Ile Phe Pro His Arg Thr Ala Leu Pro Leu His Leu Met Gln Gln
            1925                1930                1935

Gln Ile Met Ala Val Ala Gly Leu Asp Ser Ser Lys Ala Gln Lys Tyr
        1940                1945                1950

Ser Pro Ser His Ser Thr Arg Ser Trp Ala Thr Pro Ala Thr Pro
    1955                1960                1965

Pro Tyr Arg Asp Trp Thr Pro Cys Tyr Thr Pro Leu Ile Gln Val Glu
    1970                1975                1980

Gln Ser Glu Ala Leu Asp Gln Val Asn Gly Ser Leu Pro Ser Leu His
1985                1990                1995                2000

Arg Ser Ser Trp Tyr Thr Asp Glu Pro Asp Ile Ser Tyr Arg Thr Phe
            2005                2010                2015

Thr Pro Ala Ser Leu Thr Val Pro Ser Ser Phe Arg Asn Lys Asn Ser
        2020                2025                2030

Asp Lys Gln Arg Ser Ala Asp Ser Leu Val Glu Ala Val Leu Ile Ser
```

```
                2035                2040                2045
Glu Gly Leu Gly Arg Tyr Ala Arg Asp Pro Lys Phe Val Ser Ala Thr
    2050                2055                2060

Lys His Glu Ile Ala Asp Ala Cys Asp Leu Thr Ile Asp Glu Met Glu
2065                2070                2075                2080

Ser Ala Ala Ser Thr Leu Leu Asn Gly Asn Val Arg Pro Arg Ala Asn
                2085                2090                2095

Gly Asp Val Gly Pro Leu Ser His Arg Gln Asp Tyr Glu Leu Gln Asp
            2100                2105                2110

Phe Gly Pro Gly Tyr Ser Asp Glu Glu Pro Pro Gly Arg Asp Glu
        2115                2120                2125

Glu Asp Leu Ala Asp Glu Met Ile Cys Ile Thr Thr Leu
    2130                2135                2140

<210> SEQ ID NO 5
<211> LENGTH: 6486
<212> TYPE: DNA
<213> ORGANISM: Homo sapiens

<400> SEQUENCE: 5
atgatgatga tgatgatgat gaaaaaaatg cagcatcaac ggcagcagca agcggaccac     60
gcgaacgagg caaactatgc aagaggcacc agacttcctc tttctggtga aggaccaact    120
tctcagccga atagctccaa gcaaactgtc ctgtcttggc aagctgcaat cgatgctgct    180
agacaggcca aggctgccca actatgagc acctctgcac ccccacctgt aggatctctc    240
tcccaaagaa aacgtcagca atacgccaag agcaaaaaac agggtaactc gtccaacagc    300
cgacctgccc gcgcccttt ctgtttatca ctcaataacc ccatccgaag agcctgcatt    360
agtatagtgg aatggaaacc atttgacata tttatattat tggctatttt tgccaattgt    420
gtggccttag ctatttacat cccattccct gaagatgatt ctaattcaac aaatcataac    480
ttggaaaaag tagaatatgc cttcctgatt attttttacag tcgagacatt tttgaagatt    540
atagcgtatg gattattgct acatcctaat gcttatgtta ggaatggatg gaatttactg    600
gattttgtta tagtaatagt aggattgttt agtgtaattt tggaacaatt aaccaaagaa    660
acagaaggcg ggaaccactc aagcggcaaa tctggaggct ttgatgtcaa agccctccgt    720
gcctttcgag tgttgcgacc acttcgacta gtgtcaggag tgcccagttt acaagttgtc    780
ctgaactcca ttataaaagc catggttccc ctccttcaca tagccctttt ggtattattt    840
gtaatcataa tctatgctat tataggattg gaacttttta ttggaaaaat gcacaaaaca    900 tgttttttg ctgactcaga tatcgtagct gaagaggacc cagctccatg tgcgttctca    960
gggaatggac gccagtgtac tgccaatggc acggaatgta ggagtggctg ggttggcccg   1020
aacggaggca tcaccaactt tgataacttt gcctttgcca tgcttactgt gtttcagtgc   1080
atcaccatgg agggctggac agacgtgctc tactggatga atgatgctat gggatttgaa   1140
ttgccctggg tgtattttgt cagtctcgtc atctttgggt cattttttcgt actaaatctt   1200 gtacttggtg tattgagcgg agaattctca aaggaaagag agaaggcaaa agcacgggga   1260
gatttccaga agctccggga gaagcagcag ctggaggagg atctaaaggg ctacttggat   1320
tggatcaccc aagctgagga catcgatccg gagaatgagg aagaaggagg agaggaaggc   1380
aaacgaaata ctagcatgcc caccagcgag actgagtctg tgaacacaga gaacgtcagc   1440
ggtgaaggcg agaaccgagg ctgctgtgga agtctctgtc aagccatctc aaaatccaaa   1500
ctcagccgac gctggcgtcg ctggaaccga ttcaatcgca gaagatgtag ggccgccgtg   1560
```

-continued

```
aagtctgtca cgttttactg gctggttatc gtcctggtgt ttctgaacac cttaaccatt    1620
tcctctgagc actacaatca gccagattgg ttgacacaga ttcaagatat tgccaacaaa    1680
gtcctcttgg ctctgttcac ctgcgagatg ctggtaaaaa tgtacagctt gggcctccaa    1740
gcatatttcg tctctctttt caaccggttt gattgcttcg tggtgtgtgg tggaatcact    1800
gagacgatct tggtggaact ggaaatcatg tctcccctgg ggatctctgt gtttcggtgt    1860
gtgcgcctct taagaatctt caaagtgacc aggcactgga cttccctgtg caacttagtg    1920
gcatccttat taaactccat gaagtccagt gcttcgctgt tgcttctgct ttttctcttc    1980
attatcatct tttccttgct tgggatgcag ctgtttggcg gcaagtttaa ttttgatgaa    2040
acgcaaacca gcggagcac ctttgacaat ttccctcaag cacttctcac agtgttccag     2100
atcctgacag gcgaagactg gaatgctgtg atgtacgatg gcatcatggc ttacgggggc    2160
ccatcctctt caggaatgat cgtctgcatc tacttcatca tcctcttcat tgtgggtaac    2220
tatattctac tgaatgtctt cttggccatc gctgtagaca atttggctga tgctgaaagt    2280
ctgaacactg ctcagaaaga agaagcggaa gaaaaggaga ggaaaaagat tgccagaaaa    2340
gagagcctag aaaataaaaa gaacaacaaa ccagaagtca accagatagc caacagtgac    2400
aacaaggtta caattgatga ctatagaaa gaggatgaag acaaggaccc ctatccgcct     2460
tgcgatgtgc cagtagggga agaggaagag gaagaggagg aggatgaacc tgaggttcct    2520
gccggacccc gtcctcgaag gatctcggag ttgaacatga aggaaaaaat tgcccccatc    2580
cctgaaggga gcgctttctt cattcttagc aagaccaacc cgatccgcgt aggctgccac    2640
aagctcatca accaccacat cttcaccaac ctcatccttg tcttcatcat gctgagcagt    2700
gctgccctgg ccgcagagga ccccatccgc agccactcct tccggaacac gatactgggt    2760
tactttgact atgccttcac agccatcttt actgttgaga tcctgttgaa gatgacaact    2820
tttgagcttt tcctccacaa aggggccttc tgcaggaact acttcaattt gctggatatg    2880
ctggtggttg gggtgtctct ggtgtcattt gggattcaat ccagtgccat ctccgttgtg    2940
aagattctga gggtcttaag ggtcctgcgt cccctcaggg ccatcaacag agcaaaagga    3000
cttaagcacg tggtccagtg cgtcttcgtg gccatccgga ccatcggcaa catcatgatc    3060
gtcaccaccc tcctgcagtt catgtttgcc tgtatcgggg tccagttgtt caagggaag     3120
ttctatcgct gtacggatga agccaaaagt aaccctgaag aatgcagggg acttttcatc    3180
ctctacaagg atggggatgt tgacagtcct gtggtccgtg aacggatctg gcaaaacagt    3240
gatttcaact tcgacaacgt cctctctgct atgatggcgc tcttcacagt ctccacgttt    3300
gagggctggc ctgcgttgct gtataaagcc atcgactcga atggagagaa catcggccca    3360
atctacaacc accgcgtgga gatctccatc ttcttcatca tctacatcat cattgtagct    3420
ttcttcatga tgaacatctt tgtgggcttt gtcatcgtta catttcagga caaggagaa    3480
aaagagtata agaactgtga gctggacaaa atcagcgtc agtgtgttga atacgccttg     3540
aaagcacgtc ccttgcggag atacatcccc aaaaacccct accagtacaa gttctggtac    3600
gtggtgaact cttcgccttt cgaatacatg atgtttgtcc tcatcatgct caacacactc    3660
tgcttggcca tgcagcacta cgagcagtcc aagatgttca atgatgccat ggacattctg    3720
aacatggtct tcaccggggt gttcaccgtc gagatggttt tgaaagtcat cgcatttaag    3780
cctaaggggt attttagtga cgcctggaac acgtttgact ccctcatcgt aatcggcagc    3840
attatagacg tggccctcag cgaagcagac ccaactgaaa gtgaaaatgt ccctgtccca    3900
```

```
actgctacac ctgggaactc tgaagagagc aatagaatct ccatcacctt tttccgtctt    3960
ttccgagtga tgcgattggt gaagcttctc agcagggggg aaggcatccg gacattgctg    4020
tggactttta ttaagttctt tcaggcgctc ccgtatgtgg ccctcctcat agccatgctg    4080
ttcttcatct atgcggtcat tggcatgcag atgtttggga agttgccat gagagataac     4140 aaccagatca ataggaacaa taacttccag acgtttcccc aggcggtgct gctgctcttc    4200
aggtgtgcaa caggtgaggc ctggcaggag atcatgctgg cctgtctccc agggaagctc    4260
tgtgaccctg agtcagatta caaccccggg gaggagcata catgtgggag caactttgcc    4320
attgtctatt tcatcagttt ttacatgctc tgtgcatttc tgatcatcaa tctgtttgtg    4380
gctgtcatca tggataattt cgactatctg acccgggact ggtctatttt ggggcctcac    4440
catttagatg aattcaaaag aatatggtca gaatatgacc ctgaggcaaa gggaaggata    4500
aaacaccttg atgtggtcac tctgcttcga cgcatccagc ctcccctggg gtttgggaag    4560
ttatgtccac acagggtagc gtgcaagaga ttagttgcca tgaacatgcc tctcaacagt    4620
gacgggacag tcatgtttaa tgcaaccctg tttgctttgg ttcgaacggc tcttaagatc    4680
aagaccgaag ggaacctgga gcaagctaat gaagaacttc gggctgtgat aaagaaaatt    4740
tggaagaaaa ccagcatgaa attacttgac caagttgtcc ctccagctgg tgatgatgag    4800
gtaaccgtgg ggaagttcta tgccactttc ctgatacagg actactttag gaaattcaag    4860
aaacggaaag aacaaggact ggtgggaaag taccctgcga agaacaccac aattgcccta    4920
caggcgggat taaggacact gcatgacatt gggccagaaa tccggcgtgc tatatcgtgt    4980
gatttgcaag atgacgagcc tgaggaaaca aaacgagaag aagaagatga tgtgttcaaa    5040
agaaatggtg ccctgcttgg aaaccatgtc aatcatgtta atagtgatag gagagattcc    5100
cttcagcaga ccaataccac ccaccgtccc ctgcatgtcc aaaggccttc aattccacct    5160
gcaagtgata ctgagaaacc gctgtttcct ccagcaggaa attcggtgtg tcataaccat    5220
cataaccata attccatagg aaagcaagtt cccacctcaa caaatgccaa tctcaataat    5280
gccaatatgt ccaaagctgc ccatggaaag cggcccagca ttgggaacct tgagcatgtg    5340
tctgaaaatg ggcatcattc ttcccacaag catgaccggg agcctcagag aaggtccagt    5400
gtgaaaagaa cccgctatta tgaaacttac attaggtccg actcaggaga tgaacagctc    5460
ccaactattt gccgggaaga cccagagata catggctatt tcagggaccc ccactgcttg    5520
ggggagcagg agtatttcag tagtgaggaa tgctacgagg atgacagctc gcccacctgg    5580
agcaggcaaa actatggcta ctacagcaga tacccaggca gaaacatcga ctctgagagg    5640
ccccgaggct accatcatcc ccaaggattc ttggaggacg atgactcgcc cgtttgctat    5700
gattcacgga gatctccaag gagacgccta ctacctccca ccccagcatc ccaccggaga    5760
tcctccttca actttgagtg cctgcgccgg cagagcagcc aggaagaggt cccgtcgtct    5820
cccatcttcc cccatcgcac ggccctgcct ctgcatctaa tgcagcaaca gatcatggca    5880
gttgccggcc tagattcaag taaagcccag aagtactcac cgagtcactc gacccggtcg    5940
tgggccaccc ctccagcaac ccctccctac cgggactgga caccgtgcta cacccccctg    6000
atccaagtgg agcagtcaga ggccctggac caggtgaacg gcagcctgcc gtccctgcac    6060
cgcagctcct ggtacacaga cgagcccgac atctcctacc ggactttcac accagccagc    6120
ctgactgtcc ccagcagctt ccggaacaaa acagcgaca agcagaggag tgcggacagc     6180
ttggtggagg cagtcctgat atccgaaggc ttggacgct atgcaaggga cccaaaattt      6240
gtgtcagcaa caaaacacga aatcgctgat gcctgtgacc tcaccatcga cgagatggag    6300
```

```
agtgcagcca gcaccctgct taatgggaac gtgcgtcccc gagccaacgg ggatgtgggc    6360
cccctctcac accggcagga ctatgagcta caggactttg gtcctggcta cagcgacgaa    6420
gagccagacc ctgggaggga tgaggaggac ctggcggatg aaatgatatg catcaccacc    6480
ttgtag                                                                6486
```

```
<210> SEQ ID NO 6
<211> LENGTH: 2161
<212> TYPE: PRT
<213> ORGANISM: Homo sapiens

<400> SEQUENCE: 6
```

| | | | | | | | | | | | | | | |
|---|---|---|---|---|---|---|---|---|---|---|---|---|---|---|
| Met | Met | Met | Met | Met | Met | Lys | Lys | Met | Gln | His | Gln | Arg | Gln | Gln |
| 1 | | | | 5 | | | | | 10 | | | | | 15 |
| Gln | Ala | Asp | His | Ala | Asn | Glu | Ala | Asn | Tyr | Ala | Arg | Gly | Thr | Arg | Leu |
| | | | | 20 | | | | | 25 | | | | | 30 | |
| Pro | Leu | Ser | Gly | Glu | Gly | Pro | Thr | Ser | Gln | Pro | Asn | Ser | Ser | Lys | Gln |
| | | | 35 | | | | | 40 | | | | | 45 | | |
| Thr | Val | Leu | Ser | Trp | Gln | Ala | Ala | Ile | Asp | Ala | Ala | Arg | Gln | Ala | Lys |
| 50 | | | | | 55 | | | | | 60 | | | | | |
| Ala | Ala | Gln | Thr | Met | Ser | Thr | Ser | Ala | Pro | Pro | Val | Gly | Ser | Leu |
| 65 | | | | 70 | | | | | 75 | | | | | 80 |
| Ser | Gln | Arg | Lys | Arg | Gln | Tyr | Ala | Lys | Ser | Lys | Gln | Gly | Asn |
| | | | | 85 | | | | | 90 | | | | | 95 |
| Ser | Ser | Asn | Ser | Arg | Pro | Ala | Arg | Ala | Leu | Phe | Cys | Leu | Ser | Leu | Asn |
| | | | 100 | | | | | 105 | | | | | 110 | | |
| Asn | Pro | Ile | Arg | Arg | Ala | Cys | Ile | Ser | Ile | Val | Glu | Trp | Lys | Pro | Phe |
| | | | 115 | | | | | 120 | | | | | 125 | | |
| Asp | Ile | Phe | Ile | Leu | Leu | Ala | Ile | Phe | Ala | Asn | Cys | Val | Ala | Leu | Ala |
| 130 | | | | | 135 | | | | | 140 | | | | | |
| Ile | Tyr | Ile | Pro | Phe | Pro | Glu | Asp | Asp | Ser | Asn | Ser | Thr | Asn | His | Asn |
| 145 | | | | | 150 | | | | | 155 | | | | | 160 |
| Leu | Glu | Lys | Val | Glu | Tyr | Ala | Phe | Leu | Ile | Ile | Phe | Thr | Val | Glu | Thr |
| | | | | 165 | | | | | 170 | | | | | 175 | |
| Phe | Leu | Lys | Ile | Ile | Ala | Tyr | Gly | Leu | Leu | Leu | His | Pro | Asn | Ala | Tyr |
| | | | 180 | | | | | 185 | | | | | 190 | | |
| Val | Arg | Asn | Gly | Trp | Asn | Leu | Leu | Asp | Phe | Val | Ile | Val | Val | Gly |
| | | 195 | | | | | 200 | | | | | 205 | | |
| Leu | Phe | Ser | Val | Ile | Leu | Glu | Gln | Leu | Thr | Lys | Glu | Thr | Glu | Gly | Gly |
| | 210 | | | | | 215 | | | | | 220 | | | | |
| Asn | His | Ser | Ser | Gly | Lys | Ser | Gly | Gly | Phe | Asp | Val | Lys | Ala | Leu | Arg |
| 225 | | | | | 230 | | | | | 235 | | | | | 240 |
| Ala | Phe | Arg | Val | Leu | Arg | Pro | Leu | Arg | Leu | Val | Ser | Gly | Val | Pro | Ser |
| | | | | 245 | | | | | 250 | | | | | 255 | |
| Leu | Gln | Val | Val | Leu | Asn | Ser | Ile | Ile | Lys | Ala | Met | Val | Pro | Leu | Leu |
| | | | 260 | | | | | 265 | | | | | 270 | | |
| His | Ile | Ala | Leu | Leu | Val | Leu | Phe | Val | Ile | Ile | Tyr | Ala | Ile | Ile |
| | | 275 | | | | | 280 | | | | | 285 | | |
| Gly | Leu | Glu | Leu | Phe | Ile | Gly | Lys | Met | His | Lys | Thr | Cys | Phe | Phe | Ala |
| | 290 | | | | | 295 | | | | | 300 | | | | |
| Asp | Ser | Asp | Ile | Val | Ala | Glu | Glu | Asp | Pro | Ala | Pro | Cys | Ala | Phe | Ser |
| 305 | | | | | 310 | | | | | 315 | | | | | 320 |
| Gly | Asn | Gly | Arg | Gln | Cys | Thr | Ala | Asn | Gly | Thr | Glu | Cys | Arg | Ser | Gly |
| | | | | 325 | | | | | 330 | | | | | 335 | |

```
Trp Val Gly Pro Asn Gly Gly Ile Thr Asn Phe Asp Asn Phe Ala Phe
            340                 345                 350

Ala Met Leu Thr Val Phe Gln Cys Ile Thr Met Glu Gly Trp Thr Asp
            355                 360                 365

Val Leu Tyr Trp Met Asn Asp Ala Met Gly Phe Glu Leu Pro Trp Val
            370                 375                 380

Tyr Phe Val Ser Leu Val Ile Phe Gly Ser Phe Phe Val Leu Asn Leu
385                 390                 395                 400

Val Leu Gly Val Leu Ser Gly Glu Phe Ser Lys Glu Arg Glu Lys Ala
            405                 410                 415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
            435                 440                 445

Asp Pro Glu Asn Glu Glu Gly Glu Gly Gly Lys Arg Asn Thr
            450                 455                 460

Ser Met Pro Thr Ser Glu Thr Glu Ser Val Asn Thr Glu Asn Val Ser
465                 470                 475                 480

Gly Glu Gly Glu Asn Arg Gly Cys Cys Gly Ser Leu Cys Gln Ala Ile
            485                 490                 495

Ser Lys Ser Lys Leu Ser Arg Arg Trp Arg Arg Trp Asn Arg Phe Asn
            500                 505                 510

Arg Arg Arg Cys Arg Ala Ala Val Lys Ser Val Thr Phe Tyr Trp Leu
            515                 520                 525

Val Ile Val Leu Val Phe Leu Asn Thr Leu Thr Ile Ser Ser Glu His
            530                 535                 540

Tyr Asn Gln Pro Asp Trp Leu Thr Gln Ile Gln Asp Ile Ala Asn Lys
545                 550                 555                 560

Val Leu Leu Ala Leu Phe Thr Cys Glu Met Leu Val Lys Met Tyr Ser
            565                 570                 575

Leu Gly Leu Gln Ala Tyr Phe Val Ser Leu Phe Asn Arg Phe Asp Cys
            580                 585                 590

Phe Val Val Cys Gly Gly Ile Thr Glu Thr Ile Leu Val Glu Leu Glu
            595                 600                 605

Ile Met Ser Pro Leu Gly Ile Ser Val Phe Arg Cys Val Arg Leu Leu
            610                 615                 620

Arg Ile Phe Lys Val Thr Arg His Trp Thr Ser Leu Cys Asn Leu Val
625                 630                 635                 640

Ala Ser Leu Leu Asn Ser Met Lys Ser Ser Ala Ser Leu Leu Leu Leu
            645                 650                 655

Leu Phe Leu Phe Ile Ile Ile Phe Ser Leu Leu Gly Met Gln Leu Phe
            660                 665                 670

Gly Gly Lys Phe Asn Phe Asp Glu Thr Gln Thr Lys Arg Ser Thr Phe
            675                 680                 685

Asp Asn Phe Pro Gln Ala Leu Leu Thr Val Phe Gln Ile Leu Thr Gly
            690                 695                 700

Glu Asp Trp Asn Ala Val Met Tyr Asp Gly Ile Met Ala Tyr Gly Gly
705                 710                 715                 720

Pro Ser Ser Ser Gly Met Ile Val Cys Ile Tyr Phe Ile Ile Leu Phe
            725                 730                 735

Ile Cys Gly Asn Tyr Ile Leu Leu Asn Val Phe Leu Ala Ile Ala Val
            740                 745                 750
```

-continued

```
Asp Asn Leu Ala Asp Ala Glu Ser Leu Asn Thr Ala Gln Lys Glu Glu
            755                 760                 765

Ala Glu Glu Lys Glu Arg Lys Lys Ile Ala Arg Lys Glu Ser Leu Glu
            770                 775                 780

Asn Lys Lys Asn Asn Lys Pro Glu Val Asn Gln Ile Ala Asn Ser Asp
785                 790                 795                 800

Asn Lys Val Thr Ile Asp Asp Tyr Arg Glu Glu Asp Glu Asp Lys Asp
                805                 810                 815

Pro Tyr Pro Pro Cys Asp Val Pro Val Gly Glu Glu Glu Glu Glu Glu
                820                 825                 830

Glu Glu Asp Glu Pro Glu Val Pro Ala Gly Pro Arg Pro Arg Arg Ile
            835                 840                 845

Ser Glu Leu Asn Met Lys Glu Lys Ile Ala Pro Ile Pro Glu Gly Ser
            850                 855                 860

Ala Phe Phe Ile Leu Ser Lys Thr Asn Pro Ile Arg Val Gly Cys His
865                 870                 875                 880

Lys Leu Ile Asn His His Ile Phe Thr Asn Leu Ile Leu Val Phe Ile
                885                 890                 895

Met Leu Ser Ser Ala Ala Leu Ala Ala Glu Asp Pro Ile Arg Ser His
            900                 905                 910

Ser Phe Arg Asn Thr Ile Leu Gly Tyr Phe Asp Tyr Ala Phe Thr Ala
            915                 920                 925

Ile Phe Thr Val Glu Ile Leu Leu Lys Met Thr Thr Phe Gly Ala Phe
            930                 935                 940

Leu His Lys Gly Ala Phe Cys Arg Asn Tyr Phe Asn Leu Leu Asp Met
945                 950                 955                 960

Leu Val Val Gly Val Ser Leu Val Ser Phe Gly Ile Gln Ser Ser Ala
                965                 970                 975

Ile Ser Val Val Lys Ile Leu Arg Val Leu Arg Val Leu Arg Pro Leu
            980                 985                 990

Arg Ala Ile Asn Arg Ala Lys Gly Leu Lys His Val Val Gln Cys Val
            995                1000                1005

Phe Val Ala Ile Arg Thr Ile Gly Asn Ile Met Ile Val Thr Thr Leu
           1010                1015                1020

Leu Gln Phe Met Phe Ala Cys Ile Gly Val Gln Leu Phe Lys Gly Lys
1025                1030                1035                1040

Phe Tyr Arg Cys Thr Asp Glu Ala Lys Ser Asn Pro Glu Glu Cys Arg
                1045                1050                1055

Gly Leu Phe Ile Leu Tyr Lys Asp Gly Asp Val Asp Ser Pro Val Val
            1060                1065                1070

Arg Glu Arg Ile Trp Gln Asn Ser Asp Phe Asn Phe Asp Asn Val Leu
            1075                1080                1085

Ser Ala Met Met Ala Leu Phe Thr Val Ser Thr Phe Glu Gly Trp Pro
            1090                1095                1100

Ala Leu Leu Tyr Lys Ala Ile Asp Ser Asn Gly Glu Asn Ile Gly Pro
1105                1110                1115                1120

Ile Tyr Asn His Arg Val Glu Ile Ser Ile Phe Phe Ile Ile Tyr Ile
                1125                1130                1135

Ile Ile Val Ala Phe Phe Met Met Asn Ile Phe Val Gly Phe Val Ile
            1140                1145                1150

Val Thr Phe Gln Glu Gln Gly Glu Lys Glu Tyr Lys Asn Cys Glu Leu
            1155                1160                1165

Asp Lys Asn Gln Arg Gln Cys Val Glu Tyr Ala Leu Lys Ala Arg Pro
```

-continued

```
        1170                1175                1180
Leu Arg Arg Tyr Ile Pro Lys Asn Pro Tyr Gln Tyr Lys Phe Trp Tyr
1185                1190                1195                1200

Val Val Asn Ser Ser Pro Phe Glu Tyr Met Met Phe Val Leu Ile Met
                1205                1210                1215

Leu Asn Thr Leu Cys Leu Ala Met Gln His Tyr Glu Gln Ser Lys Met
                1220                1225                1230

Phe Asn Asp Ala Met Asp Ile Leu Asn Met Val Phe Thr Gly Val Phe
                1235                1240                1245

Thr Val Glu Met Val Leu Lys Val Ile Ala Phe Lys Pro Lys Gly Tyr
                1250                1255                1260

Phe Ser Asp Ala Trp Asn Thr Phe Asp Ser Leu Ile Val Ile Gly Ser
1265                1270                1275                1280

Ile Ile Asp Val Ala Leu Ser Glu Ala Asp Pro Thr Glu Ser Glu Asn
                1285                1290                1295

Val Pro Val Pro Thr Ala Thr Pro Gly Asn Ser Glu Ser Asn Arg
                1300                1305                1310

Ile Ser Ile Thr Phe Phe Arg Leu Phe Arg Val Met Arg Leu Val Lys
                1315                1320                1325

Leu Leu Ser Arg Gly Glu Gly Ile Arg Thr Leu Leu Trp Thr Phe Ile
                1330                1335                1340

Lys Phe Phe Gln Ala Leu Pro Tyr Val Ala Leu Leu Ile Ala Met Leu
1345                1350                1355                1360

Phe Phe Ile Tyr Ala Val Ile Gly Met Gln Met Phe Gly Lys Val Ala
                1365                1370                1375

Met Arg Asp Asn Asn Gln Ile Asn Arg Asn Asn Asn Phe Gln Thr Phe
                1380                1385                1390

Pro Gln Ala Val Leu Leu Leu Phe Arg Cys Ala Thr Gly Glu Ala Trp
                1395                1400                1405

Gln Glu Ile Met Leu Ala Cys Leu Pro Gly Lys Leu Cys Asp Pro Glu
                1410                1415                1420

Ser Asp Tyr Asn Pro Gly Glu Glu His Thr Cys Gly Ser Asn Phe Ala
1425                1430                1435                1440

Ile Val Tyr Phe Ile Ser Phe Tyr Met Leu Cys Ala Phe Leu Ile Ile
                1445                1450                1455

Asn Leu Phe Val Ala Val Ile Met Asp Asn Phe Asp Tyr Leu Thr Arg
                1460                1465                1470

Asp Trp Ser Ile Leu Gly Pro His His Leu Asp Glu Phe Lys Arg Ile
                1475                1480                1485

Trp Ser Glu Tyr Asp Pro Glu Ala Lys Gly Arg Ile Lys His Leu Asp
                1490                1495                1500

Val Val Thr Leu Leu Arg Arg Ile Gln Pro Pro Leu Gly Phe Gly Lys
1505                1510                1515                1520

Leu Cys Pro His Arg Val Ala Cys Lys Arg Leu Val Ala Met Asn Met
                1525                1530                1535

Pro Leu Asn Ser Asp Gly Thr Val Met Phe Asn Ala Thr Leu Phe Ala
                1540                1545                1550

Leu Val Arg Thr Ala Leu Lys Ile Lys Thr Glu Gly Asn Leu Glu Gln
                1555                1560                1565

Ala Asn Glu Glu Leu Arg Ala Val Ile Lys Lys Ile Trp Lys Lys Thr
                1570                1575                1580

Ser Met Lys Leu Leu Asp Gln Val Val Pro Pro Ala Gly Asp Asp Glu
1585                1590                1595                1600
```

-continued

```
Val Thr Val Gly Lys Phe Tyr Ala Thr Phe Leu Ile Gln Asp Tyr Phe
            1605                1610                1615
Arg Lys Phe Lys Lys Arg Lys Glu Gln Gly Leu Val Gly Lys Tyr Pro
        1620                1625                1630
Ala Lys Asn Thr Thr Ile Ala Leu Gln Ala Gly Leu Arg Thr Leu His
    1635                1640                1645
Asp Ile Gly Pro Glu Ile Arg Arg Ala Ile Ser Cys Asp Leu Gln Asp
    1650                1655                1660
Asp Glu Pro Glu Glu Thr Lys Arg Glu Glu Asp Asp Val Phe Lys
1665                1670                1675                1680
Arg Asn Gly Ala Leu Leu Gly Asn His Val Asn His Val Asn Ser Asp
            1685                1690                1695
Arg Arg Asp Ser Leu Gln Gln Thr Asn Thr Thr His Arg Pro Leu His
        1700                1705                1710
Val Gln Arg Pro Ser Ile Pro Pro Ala Ser Asp Thr Glu Lys Pro Leu
    1715                1720                1725
Phe Pro Pro Ala Gly Asn Ser Val Cys His Asn His His Asn His Asn
    1730                1735                1740
Ser Ile Gly Lys Gln Val Pro Thr Ser Thr Asn Ala Asn Leu Asn Asn
1745                1750                1755                1760
Ala Asn Met Ser Lys Ala Ala His Gly Lys Arg Pro Ser Ile Gly Asn
            1765                1770                1775
Leu Glu His Val Ser Glu Asn Gly His His Ser Ser His Lys His Asp
        1780                1785                1790
Arg Glu Pro Gln Arg Arg Ser Ser Val Lys Arg Thr Arg Tyr Tyr Glu
    1795                1800                1805
Thr Tyr Ile Arg Ser Asp Ser Gly Asp Glu Gln Leu Pro Thr Ile Cys
    1810                1815                1820
Arg Glu Asp Pro Glu Ile His Gly Tyr Phe Arg Asp Pro His Cys Leu
1825                1830                1835                1840
Gly Glu Gln Glu Tyr Phe Ser Ser Glu Glu Cys Tyr Glu Asp Asp Ser
            1845                1850                1855
Ser Pro Thr Trp Ser Arg Gln Asn Tyr Gly Tyr Tyr Ser Arg Tyr Pro
        1860                1865                1870
Gly Arg Asn Ile Asp Ser Glu Arg Pro Arg Gly Tyr His His Pro Gln
    1875                1880                1885
Gly Phe Leu Glu Asp Asp Ser Pro Val Cys Tyr Asp Ser Arg Arg
    1890                1895                1900
Ser Pro Arg Arg Arg Leu Leu Pro Pro Thr Pro Ala Ser His Arg Arg
1905                1910                1915                1920
Ser Ser Phe Asn Phe Glu Cys Leu Arg Arg Gln Ser Ser Gln Glu Glu
            1925                1930                1935
Val Pro Ser Ser Pro Ile Phe Pro His Arg Thr Ala Leu Pro Leu His
        1940                1945                1950
Leu Met Gln Gln Gln Ile Met Ala Val Ala Gly Leu Asp Ser Ser Lys
    1955                1960                1965
Ala Gln Lys Tyr Ser Pro Ser His Ser Thr Arg Ser Trp Ala Thr Pro
    1970                1975                1980
Pro Ala Thr Pro Pro Tyr Arg Asp Trp Thr Pro Cys Tyr Thr Pro Leu
1985                1990                1995                2000
Ile Gln Val Glu Gln Ser Glu Ala Leu Asp Gln Val Asn Gly Ser Leu
            2005                2010                2015
```

```
Pro Ser Leu His Arg Ser Ser Trp Tyr Thr Asp Glu Pro Asp Ile Ser
            2020                2025                2030

Tyr Arg Thr Phe Thr Pro Ala Ser Leu Thr Val Pro Ser Ser Phe Arg
        2035                2040                2045

Asn Lys Asn Ser Asp Lys Gln Arg Ser Ala Asp Ser Leu Val Glu Ala
    2050                2055                2060

Val Leu Ile Ser Glu Gly Leu Gly Arg Tyr Ala Arg Asp Pro Lys Phe
2065            2070                2075                2080

Val Ser Ala Thr Lys His Glu Ile Ala Asp Ala Cys Asp Leu Thr Ile
            2085                2090                2095

Asp Glu Met Glu Ser Ala Ala Ser Thr Leu Leu Asn Gly Asn Val Arg
            2100                2105                2110

Pro Arg Ala Asn Gly Asp Val Gly Pro Leu Ser His Arg Gln Asp Tyr
        2115                2120                2125

Glu Leu Gln Asp Phe Gly Pro Gly Tyr Ser Asp Glu Glu Pro Asp Pro
    2130                2135                2140

Gly Arg Asp Glu Glu Asp Leu Ala Asp Glu Met Ile Cys Ile Thr Thr
2145            2150                2155                2160

Leu

<210> SEQ ID NO 7
<211> LENGTH: 45
<212> TYPE: DNA
<213> ORGANISM: Homo sapiens

<400> SEQUENCE: 7
ccaactgaaa gtgaaaatgt ccctgtccca actgctacac ctggg            45

<210> SEQ ID NO 8
<211> LENGTH: 15
<212> TYPE: PRT
<213> ORGANISM: Homo sapiens

<400> SEQUENCE: 8

Pro Thr Glu Ser Glu Asn Val Pro Val Pro Thr Ala Thr Pro Gly
  1               5                  10                  15

<210> SEQ ID NO 9
<211> LENGTH: 27
<212> TYPE: DNA
<213> ORGANISM: Homo sapiens

<400> SEQUENCE: 9
aacccgctat tatgaaactt acattag                                27

<210> SEQ ID NO 10
<211> LENGTH: 9
<212> TYPE: PRT
<213> ORGANISM: Homo sapiens

<400> SEQUENCE: 10

Thr Arg Tyr Tyr Glu Thr Tyr Ile Arg
  1               5
```

$\alpha_{1D}$ CALCIUM CHANNEL EXPRESSED IN ATRIUM

CROSS-REFERENCE TO RELATED APPLICATIONS

This application is a utility application of and claims benefit of U.S. Provisional Application Ser. No. 60/480,949, filed Jun. 23, 2003, which is incorporated by reference in its entirety.

BACKGROUND

All cells rely on the regulated movement of inorganic ions across cell membranes to perform essential physiological functions. Electrical excitability, synaptic plasticity, and signal transduction are examples of processes in which changes in ion concentration play a critical role. In general, the ion channels that permit these changes are proteinaceous pores consisting of one or multiple subunits, each containing two or more membrane-spanning domains. Most ion channels have selectivity for specific ions, primarily $Na^+$, $K^+$, $Ca^{2+}$, or $Cl^-$, by virtue of physical preferences for size and charge. Electrochemical forces, rather than active transport, drive ions across membranes, thus a single channel may allow the passage of millions of ions per second. Channel opening, or "gating" is tightly controlled by changes in voltage or by ligand binding, depending on the subclass of channel. Ion channels are attractive therapeutic targets due to their involvement in so many physiological processes, yet the generation of drugs with specificity for particular channels in particular tissue types remains a major challenge.

Voltage-gated ion channels open in response to changes in membrane potential. For example, depolarization of excitable cells such as neurons result in a transient influx of $Na^+$ ions, which propagates nerve impulses. This change in $Na^+$ concentration is sensed by voltage-gated $K^+$ channels which then allow an efflux of $K^+$ ions. The efflux of $K^+$ ions repolarizes the membrane. Other cell types rely on voltage-gated $Ca^{2+}$ channels to generate action potentials. Voltage-gated ion channels also perform important functions in non-excitable cells, such as the regulation of secretory, homeostatic, and mitogenic processes. Ligand-gated ion channels can be opened by extracellular stimuli such as neurotransmitters (e.g., glutamate, serotonin, acetylcholine), or intracellular stimuli (e.g., cAMP, $Ca^{2+}$, and phosphorylation).

Calcium channels include voltage-gated and non-voltage-gated classes. Voltage-gated calcium channels can be further subdivided into T, L, N, P, and Q subtypes. T-type channels transiently activate at negative potentials while the other subtypes activate at positive potentials. The a1 subunits of voltage-gated $Ca^{2+}$ channels are similar to the a subunits of voltage-gated sodium channels, and contain four repeat regions, each containing six transmembrane domains. The P/Q type a subunits are expressed in the brain, motor neurons, and kidney and are important for transmitter release. N-type $\alpha_1$ subunits are expressed in the central and peripheral nervous systems and are also important for transmitter release. L-type $\alpha_1$ subunits are expressed in heart, lung, smooth muscle, fibroblasts, brain, pancreas, and the neuroendocrine system and mediate coupling of muscular excitation and contraction. R-type subunits are expressed in brain and muscle and are important for transmitter release. T-type subunits are expressed in brain, cardiac, and smooth muscle. Other $\alpha_1$ subunits are expressed in retina and skeletal muscle. Alpha-1 subunits associate with auxiliary subunits that regulate the function of the channels for example, by modifying the kinetics of $Ca^{2+}$ influx, $Ca^{2+}$ current amplitude, or voltage-dependence.

Non-voltage-gated $Ca^{2+}$ channels include ligand-gated channels. These channels are $Ca^{2+}$ ATPases which are expressed in muscle and other tissues. Mutations in $Ca^{2+}$ ATPases causes Brody myopathy (ATP2A1), Darier-White disease and Keratosis follicularis (ATP2A2), deafness and vestibular imbalance (ATP2B2). Another important class of non-voltage-gated $Ca^{2+}$ channel is the intracellular class, which include ryanodine receptors, inositol -1,4,5-triphosphate (IP3) receptors, nicotinic acid adenine dinucleotide phosphate (NAADP) receptor, and sphingolipid receptor (EDG1). In general, intracellular $Ca^{2+}$ channels form homotetrameric complexes. They are stimulated by second messengers such as elevation in intracellular $Ca^{2+}$ levels, ryanodine, caffeine, $IP_3$, NAADP, and sphingosine-1-phosphate. The release of intracellular $Ca^{2+}$ through these channels leads to amplification of signaling events.

Genetic or pharmacological perturbations in ion channel function can have dramatic clinical consequences. Long QT syndrome, epilepsy, cystic fibrosis, and episodic ataxia are a few examples of heritable diseases resulting from mutations in ion channel subunits. Toxic side affects such as arrhythmia and seizure which are triggered by certain drugs are due to interference with ion channel function (Sirois and Atchison, *Neurotoxicology*, 17(1):63-84, 1996; Keating,M. T., *Science* 272:681-685, 1996). Drugs are useful for the therapeutic modulation of ion channel activity, and have applications in treatment of many pathological conditions, including hypertension, angina pectoris, myocardial ischemia, asthma, bladder overactivity, alopecia, pain, heart failure, dysmenorrhea, type II diabetes, arrhythmia, graft rejection, seizure, convulsions, epilepsy, stroke, gastric hypermotility, psychoses, cancer, muscular dystrophy, and narcolepsy (Coghlan, M. J., et al., *J. Med. Chem.* 44:1627-1653, 2001; Ackerman. M. J., and Clapham, D. E., *N. Eng. J. Med.* 336:1575-1586, 1997). The growing number of identified ion channels and further understanding of their complexity will assist in future efforts at therapies that modify ion channel function.

SUMMARY

Novel $\alpha_{1D}$ calcium channel subunit polypeptides, nucleic acids, and fragments of the polypeptides and nucleic acids are provided herein. Also provided are methods of using the novel subunit polypeptides, nucleic acids, and fragments thereof.

In one aspect, the invention features an isolated L-type calcium channel $\alpha_{1D-KIVA}$ subunit polypeptide, wherein the polypeptide includes the amino acid sequence KIVA (SEQ IDNO: 2). The KIVA (SEQ ID NO: 2) sequence can be in an extracellular domain of the calcium channel. The $\alpha_{1D}$ polypeptide can be human. In one embodiment, the polypeptide does not include the following amino acid sequence: TRYYETYIR (SEQ ID NO: 10).

In one embodiment, the polypeptide includes the amino acid sequence of SEQ ID NO: 4.

In one embodiment, the polypeptide consists of the amino acid sequence of SEQ ID NO: 4.

In another aspect, the invention features an isolated L-type calcium channel $\alpha_{1D+KIVA}$ subunit polypeptide, wherein the polypeptide includes an amino acid sequence at least 85% (e.g., at least 90%, 95%, 99%) homologous to SEQ ID NO: 6, and wherein the polypeptide includes one or more of the following features:
- (a) a deletion of amino acids 1291-1305 of SEQ ID NO: 6;
- (b) an insertion of SEQ ID NO: 2; or
- (c) a deletion of amino acids 1804-1812 of SEQ ID NO: 6.

In one embodiment, the polypeptide includes the insertion of SEQ ID NO: 2, and the insertion is in an extracellular domain. The insertion can be between the third and fourth transmembrane segments of a repeat domain of the calcium channel subunit. For example, the insertion can be between the third and fourth transmembrane segments of the fourth repeat domain. In one embodiment, the insertion occurs after amino acid 1290 of SEQ ID NO: 6, e.g., the insertion is at amino acid 1290 of SEQ ID NO: 6.

In one embodiment, the polypeptide has any two of the features (a), (b), or (c).

In one embodiment, the polypeptide has all three of the features (a), (b), and (c).

In another aspect, the invention features an isolated polypeptide comprising at least 10 contiguous amino acids of SEQ ID NO: 4. The polypeptide can include at least one amino acid from the region between amino acids 1281-1284 and/or amino acids 1792 and 1793. In one embodiment, a portion of the extracellular domain is replaced by an extracellular domain from another calcium channel $\alpha_1$ subunit (e.g., another calcium channel $\alpha_{1D}$ subunit, or a calcium channel $\alpha_{1S}$ subunit, $\alpha_{1C}$ subunit, or $\alpha_{1F}$ subunit) wherein the portion that is replaced does not include a KIVA (SEQ ID NO:2) sequence.

In various embodiments, the calcium channel $\alpha_{1D+KIVA}$ subunit polypeptides described herein are labeled (e.g., with a fluorescent label, a radioactive label, or some other detectable compound, or a toxin).

In yet another aspect, the invention features an isolated L-type calcium channel $\alpha_{1D-KIVA}$ subunit nucleic acid molecule. In one embodiment, the nucleic acid encodes an isolated L-type calcium channel $\alpha_{1D-KIVA}$ subunit polypeptide, wherein the polypeptide includes the amino acid sequence KIVA (SEQ ID NO: 2). In one embodiment, the KIVA sequence (SEQ ID NO: 2) is in an extracellular domain of the calcium channel.

In one embodiment, the nucleic acid encodes a human $\alpha_{1D+KIVA}$ polypeptide. In one embodiment, the nucleic acid encodes a polypeptide that does not include the following amino acid sequence: TRYYETYIR (SEQ ID NO: 10).

In one embodiment, the nucleic acid encodes a polypeptide that includes the amino acid sequence of SEQ ID NO: 4.

In one embodiment, the nucleic acid encodes a polypeptide that consists of the amino acid sequence of SEQ ID NO: 4.

In one embodiment, the nucleic acid encodes an isolated L-type calcium channel $\alpha_{1D+KIVA}$ subunit polypeptide, wherein the polypeptide includes an amino acid sequence at least 85% homologous to SEQ ID NO: 6, and wherein the polypeptide includes one or more of the following features:
- (a) a deletion of amino acids 1291-1305 of SEQ ID NO: 6;
- (b) an insertion of SEQ ID NO: 2; or
- (c) a deletion of amino acids 1804-1812 of SEQ ID NO: 6.

In one embodiment, the nucleic acid encodes an insertion of the amino acids of SEQ ID NO: 2, and the insertion is in an extracellular domain. The insertion can be between the third and fourth transmembrane segments of a repeat domain of the calcium channel subunit. For example, the insertion can be between the third and fourth transmembrane segments of the fourth repeat domain. In one embodiment, the insertion occurs after amino acid 1290 of SEQ ID NO: 6, e.g., the insertion is at amino acid 1290 of SEQ ID NO: 6.

In one embodiment, the nucleic acid encodes a polypeptide that has any two of the features (a), (b), or (c).

In one embodiment, the nucleic acid encodes a polypeptide that has all three of the features (a), (b), and (c).

In one embodiment, the nucleic acid encodes an isolated polypeptide comprising at least 10 contiguous amino acids of SEQ ID NO: 4. The polypeptide can include at least one of amino acids 1281-1284 and/or amino acids 1792 and 1793. In one embodiment, a portion of the extracellular domain is replaced by an extracellular domain from another calcium channel $\alpha_1$ subunit, wherein the portion that is replaced does not include a KIVA (SEQ ID NO:2) sequence.

In one embodiment the nucleic acid includes the nucleotide sequence of SEQ ID NO: 3.

In one embodiment, the nucleic acid molecule consists of the nucleotide sequence of SEQ ID NO: 3.

In one embodiment, the nucleic acid is an allele of the nucleic acid sequence of SEQ ID NO: 3.

In one embodiment, the nucleic acid is a fragment of an L-type calcium $\alpha_{1D+KIVA}$ subunit nucleic acid molecule, and the fragment encodes SEQ ID NO: 2.

In another aspect, the invention features an expression vector including an L-type calcium $\alpha_{1D+KIVA}$ subunit nucleic acid molecule operably linked to a promoter.

In still another aspect, the invention features a host cell including an L-type calcium $\alpha_{1D+KIVA}$ subunit nucleic acid molecule.

In one aspect, the invention features an agent that preferentially binds to an L-type calcium channel $\alpha_{1D+KIVA}$ subunit polypeptide, e.g., an $\alpha_{1D+KIVA}$ subunit polypeptide described herein.

In one embodiment, the agent binds selectively to an L-type calcium channel $\alpha_{1D+KIVA}$ subunit polypeptide and not to an L-type calcium channel $\alpha_{1D}$ subunit polypeptide comprising the sequence of SEQ ID NO: 5.

The agent can be a small molecule, a nucleic acid, or a protein. The agent can modulate (e.g., inhibit or enhance) calcium channel activity of the L-type calcium channel $\alpha_{1D+KIVA}$ subunit polypeptide. The agent can be an antibody or antigen-binding fragment thereof, e.g., a polyclonal antibody, monoclonal antibody, or Fab fragment of a monoclonal or polyclonal antibody.

The invention also features a pharmaceutical composition that includes the agent that preferentially binds to an L-type calcium channel $\alpha_{1D+KIVA}$ subunit polypeptide and a pharmaceutically acceptable carrier.

Also provided herein is a method for detecting the presence of a calcium channel $\alpha_{1D+KIVA}$ subunit polypeptide or nucleic acid in vitro (e.g., a biological sample, such as tissue) or in vivo (e.g., in vivo imaging in a subject). The method includes: (a) contacting a sample with an agent that binds an $\alpha_{1D+KIVA}$ subunit polypeptide or nucleic acid; and (b) detecting formation of a complex between the agent and the sample (e.g., using a binding assay described herein). The method can also include contacting a reference sample (e.g., a control sample) with the agent, and determining the extent of formation of the complex between the agent and the sample relative to the reference sample.

Also provided are kits for screening assays using a calcium channel $\alpha_{1D+KIVA}$ subunit nucleic acid and/or polypeptide described herein, and instructions for use, e.g., the use of calcium channel $\alpha_{1D+KIVA}$ subunit nucleic acid to express an $\alpha_{1D+KIVA}$ subunit polypeptide in vitro, and for identifying modulators of the $\alpha_{1D+KIVA}$ subunit polypeptide. The kit can further contain a least one additional reagent, such as a label or additional agent, e.g., for detecting the $\alpha_{1D+KIVA}$ subunit polypeptide, or for monitoring an activity of the $\alpha_{1D+KIVA}$ subunit polypeptide.

In one aspect, the invention features a method for making a calcium channel. The method can include, for example, providing a nucleic acid encoding an L-type calcium channel $\alpha_{1D+KIVA}$ subunit polypeptide. The method can further include providing one or more nucleic acids encoding a calcium channel $\alpha_2/\delta$ subunit, and/or a calcium channel $\beta$ subunit. The method can further include the step of expressing the nucleic acid(s).

In one aspect, the invention features a method for modulating an L-type calcium channel $\alpha_{1D+KIVA}$ subunit polypeptide activity in a cell. For example, the method includes:

providing an L-type calcium channel comprising an $\alpha_{1D+KIVA}$ subunit polypeptide, wherein the $\alpha_{1D+KIVA}$ subunit polypeptide, e.g., an $\alpha_{1D+KIVA}$ subunit polypeptide described herein;

contacting the channel with an amount of an L-type calcium channel $\alpha_{1D+KIVA}$ subunit modulator effective to modulate an activity of the $\alpha_{1D+KIVA}$ subunit polypeptide.

The modulator can be a small molecule, a nucleic acid, or a protein.

In another aspect, the invention features a method for identifying an agent that modulates the activity of an L-type calcium channel $\alpha_{1D+KIVA}$ subunit polypeptide. For example, the method includes:

providing a first calcium channel comprising an $\alpha_{1D+KIVA}$ subunit polypeptide, e.g., an $\alpha_{1D+KIVA}$ subunit polypeptide described herein;

contacting the channel with a test compound; and evaluating an activity of the calcium channel, wherein a change in activity relative to a reference value is an indication that the compound is an agent that modulates the channel.

The test compound can be a small molecule, a peptide, or a nucleic acid.

The calcium channel can be contained within a biological sample. The sample can include a cell membrane. In one embodiment, the sample includes a cell. The cell can be a eukaryotic cell, e.g., a Xenopus oocyte or a mammalian cell.

The activity that is evaluated in the method can include regulation of calcium concentration. The evaluating can include detecting calcium flux.

The contacting of the calcium channel that includes an $\alpha_{1D+KIVA}$ subunit polypeptide can occur under conditions which, in the absence of the test compound, cause a first amount of calcium flux.

In one embodiment, the evaluating can include using a calcium flux assay.

In one embodiment, the assay uses patch clamp electrophysiology.

In one embodiment, the assay uses two electrode voltage clamp electrophysiology.

In one embodiment, the assay-is a fluorescence assay.

The method for identifying an agent that modulates the activity of an L-type calcium channel $\alpha_{1D+KIVA}$ subunit polypeptide can further include the steps of:

providing a second calcium channel comprising an $\alpha_{1D}$ subunit polypeptide, wherein the $\alpha_{1D}$ subunit polypeptide is other than an $\alpha_{1D+KIVA}$ subunit polypeptide, e.g., an $\alpha_{1D+KIVA}$ subunit polypeptide described herein;

contacting the second channel with the test compound;
evaluating the activity of the second calcium channel.

The method can further include comparing the activity of the first calcium channel in the presence of the test compound to the activity of the second calcium channel in the presence of the test compound.

Optionally, the method can further include providing a record or generating a data set of a result of the method, e.g., a print or computer-readable data set.

In some embodiments of the method, a plurality of calcium channels are provided.

In some embodiments of the method, the $\alpha_{1D+KIVA}$ subunit polypeptide includes the amino acid sequence of SEQ ID NO: 4.

In another aspect, the invention features a method for identifying an agent which selectively binds an L-type calcium channel $\alpha_{1D+KIVA}$ subunit polypeptide. For example, the method includes: providing a first $\alpha_{1D+KIVA}$ subunit polypeptide, e.g., an $\alpha_{1D+KIVA}$ subunit polypeptide described herein;

contacting the first polypeptide with a test compound;

assaying binding of the test compound to the first polypeptide;

providing a second $\alpha_{1D}$ subunit polypeptide, wherein the $\alpha_{1D}$ subunit polypeptide is other than an $\alpha_{1D+KIVA}$ subunit polypeptide;

contacting the second polypeptide with the test compound;

assaying binding of the test compound to the second polypeptide, wherein a compound which binds the first polypeptide and does not substantially bind the second polypeptide is an indication that the compound is an agent which selectively binds an L-type calcium channel $\alpha_{1D+KIVA}$ subunit polypeptide isoform.

In another aspect, the invention features a method for identifying an agent useful in the treatment of a disorder related to calcium current. For example, the method includes:

providing a calcium channel comprising an $\alpha_{1D+KIVA}$ subunit polypeptide, e.g., an $\alpha_{1D+KIVA}$ subunit polypeptide described herein;

contacting the channel with a test compound; and evaluating an activity of the channel, wherein a change in activity relative to a reference value is an indication that the test compound is an agent useful in a disorder related to calcium current.

The disorder can be a heart disorder, or an endocrine disorder, or a neuronal disorder.

The method can further include administering the compound in vivo (e.g., using an animal model).

The method can further include modifying the compound for use in vivo.

In another aspect, the invention features a method for treating a subject having a disorder related to calcium channel current. For example, the method includes:

administering to a subject in need of such treatment an effective amount of a pharmacological agent which is selective for a calcium channel comprising an $\alpha_{1D+KIVA}$ subunit.

In one embodiment, the disorder is a heart disorder.

The method of treating a subject can further include the step of identifying a subject in need of such treatment. Identifying a subject in need of such treatment can be in the judgment of a subject or a health care professional and can be subjective (e.g. opinion) or objective (e.g. measurable by a test or diagnostic method).

The details of one or more embodiments of the invention are set forth in the tables and the description below. Other features, objects, and advantages of the invention will be apparent from the description, and from the claims.

BRIEF DESCRIPTION OF THE SEQUENCES

The following sequences are provided in Table 1.
SEQ ID NO: 1 is the nucleotide sequence of the human L-type calcium channel $\alpha_{1D+KIVA}$ subunit "KIVA" site.

SEQ ID NO: 2 is the amino acid sequence of the human L-type calcium channel $\alpha_{1D+KIVA}$ subunit "KIVA" site.

SEQ ID NO: 3 is the nucleotide sequence of the human L-type calcium channel $\alpha_{1D+KIVA}$ subunit cDNA.

SEQ ID NO: 4 is the amino acid sequence of the human L-type calcium channel $\alpha_{1D+KIVA}$ subunit polypeptide.

SEQ ID NO: 5 is the nucleotide sequence of the coding region of a human L-type calcium channel .alpha..sub. lD subunit (GENBANK® accession number M76558).

SEQ ID NO: 6 is the amino acid sequence of a human L-type calcium channel $\alpha_{1D}$ subunit polypeptide (GenBank® accession number Q01668).

SEQ ID NO: 7 is the nucleotide sequence of SEQ ID NO: 5 (base pairs 3871-3915 of SEQ ID NO: 5) that is replaced by a nucleotide sequence encoding the "KIVA" site in the novel isoform of encoded by SEQ ID NO: 3.

SEQ ID NO: 8 is the amino acid sequence of SEQ ID NO: 6 (amino acids 1291-1305 of SEQ ID NO: 6) that is replaced by the "KIVA" insert in the novel isoform of SEQ ID NO: 4.

SEQ ID NO: 9 is the nucleotide sequence of SEQ ID NO: 5 (base pairs 5409-5435 of SEQ ID NO: 5) that is absent from the nucleotide sequence of SEQ ID NO: 3.

SEQ ID NO: 10 is the amino acid sequence of SEQ ID NO: 6 (amino acids 1804-1812 of SEQ ID NO: 6) that is absent from the nucleotide sequence of SEQ ID NO: 4.

DETAILED DESCRIPTION

The invention is based, in part, on the identification of a cDNA encoding a novel isoform of an L-type calcium channel $\alpha_{1D}$ subunit. The novel cDNA was isolated from human cardiac atrial tissue. The coding sequence of the cDNA is shown in SEQ ID NO: 3. The predicted amino acid sequence of the novel isoform is shown in SEQ ID NO: 4. A related human L-type calcium channel $\alpha_{1D}$ subunit nucleotide sequence was deposited in GENBANK®under accession number M76558 (SEQ ID NO: 5). The novel isoform differs from the related sequence in the GENBANK® database in several respects. First, the nucleotide sequence of the novel isoform contains a deletion of base pairs 4381-4425 of M76558 (this is equivalent to a deletion of base pairs 3871-3915 of SEQ ID NO:5, which is the coding region of the sequence in M76558). Second, the novel isoform contains a replacement of base pairs 4381 to 4425 with the novel nucleotide sequence shown in SEQ ID NO: 1. These changes result in a polypeptide sequence that is related to the channel $\alpha_{1D}$ subunit polypeptide under GENBANK® accession number Q01668, with the following differences. First, the novel isoform contains a deletion of nine amino acids (residues 1291-1305). Second, the replacement of base pairs at nucleotides 43814425 results in a replacement of 15 amino acids with the sequence KIVA (SEQ ID NO: 2). The site of replacement of nucleotides 4381-4425 is at the junction of the third and fourth transmembrane segments (S3 and S4) in the fourth repeat region of the gene (see discussion of channel $\alpha_{1D}$ subunit domain structure in the section below). Interestingly, this junction is the site of an insertion in an atrial channel $\alpha_{1D}$ isoform isolated from rat (Takimoto et al., J. Mol. Cell. Cardiol. 29:3035-3042, 1997). Also, the novel human atrial channel $\alpha_{1D}$ isoform could be isolated on multiple independent occasions. These observations suggest conservation in sites of variation among channel $\alpha_{1D-KIVA}$ subunits and other channel $\alpha_{1D}$ polypeptides.

As used herein, the term "calcium channel $\alpha_{1D-KIVA}$ subunit" or "$\alpha_{1D-KIVA}$" refers to any calcium channel α1D subunit nucleic acid or polypeptide that has one or more of the features of the novel isoform described above. For a calcium channel $\alpha_{1D-KIVA}$ subunit polypeptide, these features include (i) an insertion of a "KIVA (SEQ ID NO: 2)" amino acid sequence; (ii) a deletion of about 15 amino acids at amino acid residues 1291-1305 of a human calcium channel $\alpha_{1D}$ subunit, or a corresponding region or sequence in a related calcium channel subunit; (iii) a deletion of about nine amino acids of a human calcium channel $\alpha_{1D}$ subunit at residues 1803-1811 of the sequence in GENBANK® accession no. Q01668 (also SEQ ID NO: 6), or a corresponding region or sequence in a related calcium channel subunit. The deletions include deletions of amino acids sequences homologous to SEQ ID NO: 8 (for ii), and SEQ ID NO: 10 (for iii). For an $\alpha_{1D-KIVA}$ nucleic acid, these features include (iv) an insertion of 12 nucleotides encoding a "KIVA (SEQ ID NO: 2)" sequence; (v) a deletion of about 45 base pairs corresponding to residues 4381-4425 human calcium channel $\alpha_{1D}$ subunit under GENBANK® accession no. M76558 (or residues 3871-3915 of SEQ ID NO:5), or a corresponding region or sequence in a related (e.g., non-human calcium channel $\alpha_{1D}$ subunit); and (vi) a deletion of about 27 base pairs corresponding to residues 5419-5945 of human calcium channel $\alpha_{1D}$ subunit under GENBANK® accession no. M76558 (or residues 5409-5435 of SEQ ID NO:5), or a corresponding region in a related (e.g., non-human calcium channel $\alpha_{1D}$subunit). The nucleic acid deletions include deletions of nucleotide sequences homologous to the sequence of SEQ ID NO: 1 (for iv), SEQ ID NO: 7 (for v) and SEQ ID NO: 9 (for vi).

L-type Voltage-Gated Calcium Channels

Voltage-gated calcium channels are multisubunit transmembrane proteins having a large $\alpha_1$ subunit of approximately 130-200 kilodaltons (kD), an $\alpha_2$ subunit which covalently associates with a small δ subunit, and a β subunit of approximately 60 kD or less. These channels mediate the influx of calcium ions into cells. The $\alpha_1$ subunit forms the voltage-sensitive, pore-forming part of the channel, and the other subunits regulate activity of the $\alpha_1$ subunit. Voltage-gated ion channels, including the calcium channels described herein, undergo cycles of resting state (polarized; closed channel; activateable), open state (depolarized; open channel; activated) and closed state (depolarized, closed channel; inactivated) in response to changes in membrane polarization. Charged regions of the ion-conducting $\alpha_1$ subunit are sensitive to changes in membrane polarization. β subunits modulate the current, voltage-dependence, activation, and inactivation of the $\alpha_1$ subunits of calcium channels.

L-type calcium channels are high-voltage activated calcium channels that contain $\alpha_{1S}$, $\alpha_{1C}$, $\alpha_{1D}$, or $\alpha_{1F}$ subunits, also referred to as $Ca_v1.1$, $Ca_v1.2$, $Ca_v1.3$, and $Ca_v1.4$, respectively. L-type calcium channels are typically antagonized by dihydropyridines. L-type channels are expressed in many tissues including skeletal muscle, cardiac muscle, endocrine cells, neurons, and retina and mediate a variety of biological effects including excitation-contraction coupling, calcium homeostasis, gene regulation, hormone secretion, and tonic neurotransmitter release (Catterall, Annu. Rev. Cell. Dev. Biol. 16:521-55, 2000).

The $\alpha_1$ subunit of calcium channels contains four repeated domains (I-IV). Each of these repeated domains contains six transmembrane segments (S1-S6) (Reviewed in Catterall, Annu. Rev. Cell. Dev. Biol. 16:521-555, 2000).

As used herein, a "calcium channel" refers to a protein which is involved in receiving, conducting, and transmitting signals, in a cell, such as a muscle cell, e.g., a cardiac cell. Calcium channels are typically expressed in many cell types, e.g., neuron, muscle, and endocrine, cells.

As used herein, a "calcium channel mediated activity" refers to an activity, function, or response which involves a calcium channel, e.g., a calcium channel in a brain cell or a muscle cell. Calcium channel mediated activities are activities involved in receiving, conducting, and transmitting signals in, for example, the nervous system, muscle tissue, cardiac tissue, and other cells and tissues. Calcium channel mediated activities include, for example, regulation of calcium influx into cells, excitation-contraction coupling, regulation of hormone secretion and regulation of neurotransmitter release from cells. Also, as used interchangeably herein a "calcium channel $\alpha_{1D+KIVA}$ subunit activity", "biological activity of calcium channel $\alpha_{1D+KIVA}$ subunit" or "functional activity of a calcium channel $\alpha_{1D+KIVA}$ subunit", refers to an activity, function, or response of a calcium channel $\alpha_{1D+KIVA}$ subunit protein, polypeptide or nucleic acid molecule.

Isolated proteins of the present invention, e.g., calcium channel $\alpha_{1D+KIVA}$ subunit proteins described herein, have an amino acid sequence sufficiently homologous to the amino acid sequence of SEQ ID NO:4 or are encoded by a nucleotide sequence sufficiently homologous to SEQ ID NO:3. As used herein, the term "sufficiently homologous" refers to a first amino acid or nucleotide sequence which contains a sufficient or minimum number of identical or equivalent (e.g., an amino acid residue-which has a similar side chain) amino acid residues or nucleotides to a second amino acid or nucleotide sequence such that the first and second amino acid or nucleotide sequences share common structural domains or motifs or a common functional activity.

Accordingly, another embodiment of the invention features isolated calcium channel $\alpha_{1D+KIVA}$ subunit proteins and polypeptides having a calcium channel $\alpha_{1D+KIVA}$ subunit activity. Preferred proteins are calcium channel $\alpha_{1D+KIVA}$ subunit proteins having a KIVA sequence (SEQ ID NO:2), preferably in an extracellular domain, and lacking a TRYYETYIR sequence (SEQ ID NO: 10). Other preferred proteins are proteins having the sequence of SEQ ID NO: 4.

The novel human calcium channel $\alpha_{1D+KIVA}$ subunit coding sequence (of SEQ ID NO: 3), which is approximately 6,426 nucleotides in length, encodes a protein having a molecular weight of approximately 200 kD and which is approximately 2141 amino acid residues in length. The gene encoding this novel isoform is expressed in the atrium of the heart.

Various aspects of the invention are described in further detail in the following subsections.

Isolated Nucleic Acid Molecules

One aspect of the invention pertains to isolated nucleic acid molecules that encode calcium channel $\alpha_{1D+KIVA}$ subunit polypeptides or biologically active portions thereof, as well as nucleic acid fragments sufficient for use as hybridization probes to identify nucleic acid molecules that encode related isoforms of the novel calcium channel $\alpha_{1D+KIVA}$ subunits described herein and fragments for use as PCR primers for the amplification or mutation of calcium channel $\alpha_{1D+KIVA}$ subunit nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated calcium channel $\alpha_{1D+KIVA}$ subunit nucleic acid molecule can contain less than about 5 kb, 4 kb, 3 kb, 2kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, SEQ ID NO:3, or a portion thereof, can be isolated using standard molecular biology techniques and the sequence information provided herein. Using all or portion of the nucleic acid sequence of SEQ ID NO:1, or SEQ ID NO:3 as a hybridization probe, calcium channel $\alpha_{1D+KIVA}$ nucleic acid molecules can be isolated using standard hybridization and cloning techniques (e.g., as described in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989).

Moreover, a nucleic acid molecule encompassing all or a portion of SEQ ID NO: 3 can be isolated by the polymerase chain reaction (PCR) using synthetic oligonucleotide primers designed based upon the sequence of SEQ ID NO:1 or SEQ ID NO:3.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to calcium channel $\alpha_{1D+KIVA}$ nucleotide sequences can be prepared by standard synthetic techniques, e.g., using an automated DNA synthesizer.

In another embodiment, an isolated nucleic acid molecule of the invention comprises a $\alpha_{1D+KIVA}$ nucleic acid molecule which is a complement of the nucleotide sequence shown in SEQ ID NO: 1, SEQ ID NO: 3, or a portion of these nucleotide sequences. A nucleic acid molecule which is complementary to the nucleotide sequence shown in SEQ ID NO: 1 or SEQ ID NO: 3, is one which is sufficiently complementary to the nucleotide sequence shown in SEQ ID NO:1 or SEQ ID NO: 3, such that it can hybridize to the nucleotide sequence shown in SEQ ID NO: 1 or SEQ ID NO: 3.

In still another preferred embodiment, an isolated nucleic acid molecule of the present invention comprises a nucleotide sequence which is at least about 75%, 85%, 95% or more homologous to the entire length of the nucleotide sequence shown in SEQ ID NO:3, or a portion of this nucleotide sequence.

Moreover, the nucleic acid molecule of the invention can comprise only a portion of the nucleic acid sequence of SEQ ID NO:3, for example a fragment which can be used as a probe or primer or a fragment encoding a biologically active portion of an $\alpha_{1D+KIVA}$ subunit protein. The nucleotide sequence determined from the cloning of the human $\alpha_{1D+KIVA}$ cDNA allows for the generation of probes and primers designed for use in identifying and/or cloning related isoforms, as well as homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, SEQ ID NO:3, of an anti-sense sequence of SEQ ID NO:1, SEQ ID NO:3, or of a naturally occurring allelic variant or mutant of SEQ ID NO:1 or SEQ ID NO:3.

Probes based on the $\alpha_{1D+KIVA}$ nucleotide sequences can be used to detect transcripts encoding related isoforms. The probe can further include a label group attached thereto, e.g., the label group can be a radioisotope, a fluorescent compound, an enzyme, or an enzyme co-factor. Such probes can be used as a part of a diagnostic test kit for identifying cells or tissue which express or misexpress an $\alpha_{1D+KIVA}$ protein, such as by measuring a level of an $\alpha_{1D+KIVA}$-encoding nucleic acid in a sample of cells from a subject e.g., detecting $\alpha_{1D+KIVA}$ mRNA levels or determining whether a genomic $\alpha_{1D}$ subunit gene has been mutated or deleted in a region that would affect expression of the $\alpha_{1D+KIVA}$ isoform.

A nucleic acid fragment encoding a "biologically active portion of an $\alpha_{1D+KIVA}$ protein" can be prepared by isolating a portion of the nucleotide sequence of SEQ ID NO: 3, which encodes a polypeptide having an $\alpha_{1D+KIVA}$ biological activity (the biological activities of the $\alpha_{1D+KIVA}$ proteins are described herein), expressing the encoded portion of the $\alpha_{1D+KIVA}$ protein (e.g., by recombinant expression in vitro) and assessing the activity of the encoded portion of the $\alpha_{1D+KIVA}$ protein.

The invention further encompasses nucleic acid molecules that differ from the nucleotide sequence shown in SEQ ID NO:3, due to degeneracy of the genetic code and thus encode the same $\alpha_{1D+KIVA}$ proteins as those encoded by the nucleotide sequence shown in SEQ ID NO:3. In another embodiment, an isolated nucleic acid molecule of the invention has a nucleotide sequence encoding a protein having an amino acid sequence shown in SEQ ID NO: 4.

In addition to the $\alpha_{1D+KIVA}$ nucleotide sequences shown in SEQ ID NO:1 and SEQ ID NO:3, it will be appreciated by those skilled in the art that DNA sequence polymorphisms that lead to changes in the amino acid sequences of the $\alpha_{1D+KIVA}$ proteins may exist within a population (e.g., the human population). Such genetic polymorphism in the $\alpha_{1D+KIVA}$ genes may exist among individuals within a population due to natural allelic variation. As used herein, the terms "gene" and "recombinant gene" refer to nucleic acid molecules comprising an open reading frame encoding an $\alpha_{1D+KIVA}$ protein, preferably a mammalian $\alpha_{1D+KIVA}$ protein. Such natural allelic variations can typically result in 1-5% variance in the nucleotide sequence of an $\alpha_{1D+KIVA}$ gene. Any and all such nucleotide variations and resulting amino acid polymorphisms in $\alpha_{1D+KIVA}$ genes that are the result of natural allelic variation and that do not alter the functional activity of an $\alpha_{1D+KIVA}$ protein are intended to be within the scope of the invention.

Moreover, nucleic acid molecules encoding other $\alpha_{1D+KIVA}$ calcium channel family members and thus which have a nucleotide sequence which differs from the $\alpha_{1D+KIVA}$ sequences of SEQ ID NO:1 and SEQ ID NO:3, are intended to be within the scope of the invention. For example, another $\alpha_{1D+KIVA}$ cDNA can be identified based on the nucleotide sequence of human $\alpha_{1D+KIVA}$. Moreover, nucleic acid molecules encoding $\alpha_{1D+KIVA}$ proteins from different species, and thus which have a nucleotide sequence which differs from the $\alpha_{1D+KIVA}$ sequences of SEQ ID NO:1 and SEQ ID NO:3 are intended to be within the scope of the invention. For example, a mouse $\alpha_{1D+KIVA}$ cDNA can be identified based on the nucleotide sequence of a human $\alpha_{1D+KIVA}$.

Nucleic acid molecules corresponding to natural allelic variants and homologues of the $\alpha_{1D+KIVA}$ cDNAs of the invention can be isolated based on their homology to the $\alpha_{1D+KIVA}$ nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:3. Preferably, the molecule hybridizes under highly stringent conditions. In other embodiments, the nucleic acid is at least 30, 300, 500, 700, 850, 950, or 2000 nucleotides in length. As used herein, the term "hybridizes under stringent conditions" is intended to describe conditions for hybridization and washing under which nucleotide sequences at least 60%, 85%, or 95% homologous to each other typically remain hybridized to each other. Hybridization conditions are known to those skilled in the art and can be found in Current Protocols in Molecular Biology, John Wiley & Sons, N.Y., 6.3.1-6.3.6, 1991. Moderate hybridization conditions are defined as equivalent to hybridization in 2× sodium chloride/sodium citrate (SSC) at 30° C., followed by a wash in 1×SSC, 0.1% SDS at 50° C. Highly stringent conditions are defined as equivalent to hybridization in 6×sodium chloride/sodium citrate (SSC) at 45° C., followed by a wash in 0.2×SSC, 0.1% SDS at 65° C.

An isolated nucleic acid molecule of the invention that hybridizes under moderate or highly stringent conditions to the sequence of SEQ ID NO: 3 can correspond to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the $\alpha_{1D+KIVA}$ sequences that may exist in the population, the skilled artisan will further appreciate that changes can be introduced by mutation into the nucleotide sequences of SEQ ID NO:1 or SEQ ID NO:3, thereby leading to changes in the amino acid sequence of the encoded $\alpha_{1D+KIVA}$ proteins, without altering the functional ability of the $\alpha_{1D+KIVA}$ proteins. For example, nucleotide substitutions leading to amino acid substitutions at "non-essential" amino acid residues can be made in the sequence of SEQ ID NO:1 or SEQ ID NO:3. A "non-essential" amino acid residue is a residue that can be altered from the wild-type sequence of $\alpha_{1D+KIVA}$ (e.g., the sequence of SEQ ID NO: 4) without altering the biological activity, whereas an "essential" amino acid residue is required for biological activity. For example, amino acid residues that are conserved among the $\alpha_{1D+KIVA}$ proteins of the present invention, are predicted to be particularly unamenable to alteration. Furthermore, additional amino acid residues that are conserved between the $\alpha_{1D+KIVA}$ proteins of the present invention and other $\alpha_{1D}$ calcium channel subunits are not likely to be amenable to alteration.

Accordingly, another aspect of the invention pertains to nucleic acid molecules encoding $\alpha_{1D+KIVA}$ proteins that contain changes in amino acid residues that are not essential for activity. Such $\alpha_{1D+KIVA}$ proteins differ in amino acid sequence from SEQ ID NO:4 yet retain biological activity. Biological activity can be measured by an assay described herein, e.g., a calcium channel activity assay, e.g., a $Ca^{2+}$ influx assay. In one embodiment, the isolated nucleic acid molecule comprises a nucleotide sequence encoding a protein, wherein the protein comprises an amino acid sequence at least about 65%, 75%, 85%, 95% or more homologous to SEQ ID NO: 4.

An isolated nucleic acid molecule encoding an $\alpha_{1D+KIVA}$ protein homologous to the protein of SEQ ID NO: 4 can be created by introducing one or more nucleotide substitutions, additions or deletions into the nucleotide sequence of SEQ ID NO: 3 such that one or more amino acid substitutions, additions or deletions are introduced into the encoded protein. Mutations can be introduced into SEQ ID NO: 3 by standard techniques, such as site-directed mutagenesis and PCR-mediated mutagenesis. Conservative amino acid substitutions can be made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an $\alpha_{1D+KIVA}$ protein is preferably replaced with another amino acid residue from the same side chain family. Following mutagenesis of SEQ ID NO: 3, the encoded protein can be expressed recombinantly and the activity of the protein can be determined.

A mutant $\alpha_{1D+KIVA}$ protein can be assayed for the ability to (1) interact with a non-$\alpha_{1D+KIVA}$ protein molecule, e.g., calcium channel $\beta$, $\gamma$, or $\alpha_2/\delta$ subunits, protein kinase A, protein kinase C; (2) activate an $\alpha_{1D+KIVA}$-dependent signal transduction pathway; (3) modulate the release of neurotransmitters, (4) modulate membrane excitability, (5) modulate excitation-contraction coupling.

In addition to the nucleic acid molecules encoding $\alpha_{1D+KIVA}$ proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire $\alpha_{1D+KIVA}$ coding strand, or to only a portion thereof. In one embodiment, an antisense nucleic acid molecule is antisense to a "coding region" of the coding strand of a nucleotide sequence encoding $\alpha_{1D+KIVA}$. The term "coding region" refers to the region of the nucleotide sequence comprising codons which are translated into amino acid residues (e.g., the coding region of the human calcium channel $\alpha_{1D+KIVA}$ subunit corresponds to SEQ ID NO:3). In another embodiment, the antisense nucleic acid molecule is antisense to a "noncoding region" of the coding strand of a nucleotide sequence encoding $\alpha_{1D+KIVA}$. The term "noncoding region" refers to 5' and 3' sequences which flank the coding region that are not translated into amino acids (i.e., also referred to as 5' and 3' untranslated regions).

Given the coding strand sequences encoding $\alpha_{1D-KIVA}$ disclosed herein (e.g., SEQ ID NO: 1 and SEQ ID NO: 3), antisense nucleic acids of the invention can be designed according to the rules of Watson and Crick base pairing. The antisense nucleic acid molecule can be complementary to the entire coding region of $\alpha_{1D-KIVA}$ mRNA, but more preferably is an oligonucleotide which is antisense to only a portion of the coding or noncoding region of $\alpha_{1D-KIVA}$ mRNA. For example, the antisense oligonucleotide can be complementary to the region surrounding the translation start site of $\alpha_{1D-KIVA}$ mRNA. The antisense oligonucleotide can be complementary to the region encoding the KIVA sequence (SEQ ID NO: 2), e.g., complementary to SEQ ID NO: 1. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to ncrease the physical stability of the duplex formed between the antisense and sense nucleic acids, e.g., phosphorothioate derivatives and acridine substituted nucleotides can be used. amples of modified nucleotides which can be used to generate the antisense nucleic acid include 5-fluorouracil. 5-bromouracil, 5 -chiorouracil, 5-iodouracil, hypoxanthine, antine, 4-acetylcytosine, 5-(carboxyhydroxylmethyl)-uraci 1 ,5-carboxymethylaminomethyl-2-thiouridine, 5 -carboxymethylaminomethyluracil, dihydro-uracil, beta-D-galactosylqueosine, inosine, N6isopentenyladenine, 1 -methylguanine, 1 -methyl-inosine, 2,2-dimethylguanine, 2-methyladenine, 2-methylguanine, 3 -methylcytosine. 5 -methyl-cytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5 -methoxyuracil, 2-methylthio-N6-isopenten- yladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2, 6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an $\alpha_{1D+KIVA}$ protein to thereby inhibit expression of the protein, e.g., by inhibiting transcription and/or translation. The hybridization can be by conventional nucleotide complementarity to form a stable duplex, or, for example, in the case of an antisense nucleic acid mlecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. *Nucleic Acids. Res.* 15:6625-6641, 1987). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. *FEBS Lett.* 215:327-330, 1987).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach *Nature* 334:585-591, 1988)) can be used to catalytically cleave $\alpha_{1D+KIVA}$ mRNA transcripts to thereby inhibit translation of $\alpha_{1D+KIVA}$ mRNA. A ribozyme having specificity for an $\alpha_{1D+KIVA}$-encoding nucleic acid can be designed based upon the nucleotide sequence of an $\alpha_{1D+KIVA}$ cDNA disclosed herein (i.e., SEQ ID NO:1 or SEQ ID NO:3). For example, a derivative of a Tetrahymena L-19 IVS RNA can be constructed in which the nucleotide sequence of the active site is complementary to the nucleotide sequence to be cleaved in an $\alpha_{1D+KIVA}$-encoding mRNA. See, e.g., Cech et al. U.S. Pat. No. 4,987,071; and Cech et al. U.S. Pat. No. 5,116,742. Alternatively, $\alpha_{1D+KIVA}$ mRNA can be used to select a catalytic RNA having a specific ribonuclease activity from a pool of RNA molecules. See, e.g., Bartel, D. and Szostak, J. W. *Science* 261:1411-1418, 1993.

In another embodiment of the present invention, RNA interference (RNAi) can be used to inhibit the expression of an $\alpha_{1D+KIVA}$ protein. Various inhibitory RNAi molecules can be identified and those that inhibit expression of an $\alpha_{1D+KIVA}$ subunit can be formulated as pharmaceutical compositions to be administered in the methods of treatment described herein.

RNAi is a term used to refer to the mechanism by which a particular mRNA is degraded in host cells. To inhibit an mRNA, double-stranded RNA (dsRNA) corresponding to a portion of the gene to be silenced (e.g., a gene encoding an $\alpha_{1D+KIVA}$ subunit polypeptide) is introduced into a cell. The dsRNA is digested into 21-25 nucleotide-long duplexes called short interfering RNAs (or siRNAs), which bind to a nuclease complex to form what is known as the RNA-induced silencing complex (or RISC). The RISC targets the homologous transcript by base pairing interactions between one of the siRNA strands and the endogenous mRNA. It then cleaves the mRNA about 12 nucleotides from the 3' terminus of the siRNA (see Sharp et al., *Genes Dev.* 15:485-490,2001, and Hammond et al., *Nature Rev. Gen.* 2:110-119, 2001). RNAi has proven successful in human cells, including human embryonic kidney and HeLa cells (see, e.g., Elbashir et al., *Nature* 411:494-498, 2001). Gene silencing can be induced in mammalian cells by enforcing endogenous expression of RNA hairpins (see Paddison et al., *Proc. Natl. Acad. Sci. USA* 99:1443-1448, 2002) or by transfection of small (21-23 nt) dsRNA (reviewed in Caplen, *Trends in Biotech.* 20:49-51, 2002).

RNAi technology utilizes standard molecular biology methods. The dsRNA (which, here, for example, would correspond to the sequence encoding an $\alpha_{1D+KIVA}$ subunit polypeptide) can be produced by standard methods (e.g., by simultaneously transcribing both strands of a template DNA corresponding to an $\alpha_{1D+KIVA}$ subunit sequence with T7 RNA polymerase; the RNA can also be chemically synthesized or recombinantly produced). Kits for producing dsRNA are available commercially (from, e.g., New England Biolabs, Inc). The RNA used to mediate RNAi can include synthetic or modified nucleotides, such as phosphorothioate nucleotides. Methods of transfecting cells with dsRNA or with plasmids engineered to make dsRNA are also routine in the art.

Gene silencing effects similar to those observed with RNAi have been reported in mammalian cells transfected with an mRNA-cDNA hybrid construct (Lin et al., *Biochem. Biophys. Res. Comm.* 281:639-644, 2001). Accordingly, mRNA-cDNA hybrids containing $\alpha_{1D+KIVA}$ subunit sequence, as well as duplexes that contain $\alpha_{1D+KIVA}$ subunit sequence (e.g., duplexes containing 21-23 bp monomers), are within the scope of the present invention. The hybrids and duplexes can be tested for activity according to the assays described herein (i.e., they can serve as the test agents), and those that exhibit inhibitory activity can be used to treat patients who have, or who may develop, a disease or condition associated with an $\alpha_{1D+KIVA}$ subunit activity, e.g., a heart disease.

The dsRNA molecules of the invention (double-stranded RNA molecules corresponding to portions of an $\alpha_{1D+KIVA}$ subunit gene) can vary in a number of ways. For example, they can include a 3' hydroxyl group and, as noted above, can contain strands of 21, 22, or 23 consecutive nucleotides. Moreover, they can be blunt ended or include an overhanging end at either the 3' end, the 5' end, or both ends. For example, at least one strand of the RNA molecule can have a 3' overhang from about 1 to about 6 nucleotides (e.g., 1-5, 1-3, 2-4 or 3-5 nucleotides (whether pyrimidine or purine nucleotides) in length. Where both strands include an overhang, the length of the overhangs may be the same or different for each strand. To further enhance the stability of the RNA duplexes, the 3' overhangs can be stabilized against degradation (by, e.g., including purine nucleotides, such as adenosine or guanosine nucleotides or replacing pyrimidine nucleotides by modified analogues (e.g., substitution of uridine 2 nucleotide 3' overhangs by 2'-deoxythymidine is tolerated and does not affect the efficiency of RNAi). The single stranded $\alpha_{1D+KIVA}$ subunit RNA molecules that make up the duplex or hybrid inhibitor, or that act simply as antisense RNA oligonucleotides, are also within the scope of the invention. Any dsRNA can be used in the methods of the present invention, provided it has sufficient homology to a target gene of interest, e.g., an $\alpha_{1D+KIVA}$ subunit gene, to mediate RNAi. While duplexes having 21-23 nucleotides are described above, the invention is not so limited; there is no upper limit on the length of the dsRNA that can be used (e.g., the dsRNA can range from about 21 base pairs of the gene to the full length of the gene or more (e.g., 50-100, 100-250, 250-500, 500-1000, or over 1000 base pairs).

When these nucleic acids are administered to a human, they can reduce $\alpha_{1D+KIVA}$ subunit mRNA levels, thereby inhibiting expression of an $\alpha_{1D+KIVA}$ subunit. The cell or organism is maintained under conditions in which $\alpha_{1D+KIVA}$ subunit mRNA is degraded, thereby mediating RNAi in the cell or organism. Alternatively, cells can be obtained from the individual, treated ex vivo, and re-introduced into the individual.

In yet another embodiment, the $\alpha_{1D+KIVA}$ nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. *Bioorganic & Medicinal Chemistry* 4 (1): 5-23, 1996). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. supra; Perry-O'Keefe et al. *Proc. Natl. Acad. Sci.* 93: 14670-675, 1996.

PNAs of $\alpha_{1D+KIVA}$ nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of $\alpha_{1D+KIVA}$ nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B., supra)); or as probes or primers for DNA sequencing or hybridization (Hyrup B. et al., supra; Perry-O'Keefe, supra).

In another embodiment, PNAs of $\alpha_{1D+KIVA}$ can be modified, (e.g., to enhance their stability or cellular uptake), by attaching lipophilic or other helper groups to PNA, by the formation of PNA-DNA chimeras, or by the use of liposomes or other techniques of drug delivery known in the art.

In other embodiments, the oligonucleotide may include other appended groups such as peptides (e.g., for targeting host cell receptors in vivo), or agents facilitating transport across the cell membrane (see, e.g., Letsinger et al. *Proc. Natl. Acad. Sci. US.* 86:6553-6556, 1989; Lemaitre et al. *Proc. Natl. Acad. Sci. USA* 84:648-652, 1987; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. *Bio-Techniques* 6:958-976, 1988) or intercalating agents. (See, e.g., Zon *Pharm. Res.* 5:539-549, 1988). To this end, the oligonucleotide may be conjugated to another molecule, (e.g., a peptide, hybridization triggered cross-linking agent, transport agent, or hybridization-triggered cleavage agent).

Isolated $\alpha_{1D+KIVA}$ Proteins and Anti-$\alpha_{1D+KIVA}$ Antibodies

One aspect of the invention pertains to isolated calcium channel $\alpha_{1D+KIVA}$ subunit proteins, and biologically active portions thereof, as well as polypeptide fragments suitable for use as immunogens to raise anti-$\alpha_{1D+KIVA}$ antibodies. In one embodiment, native $\alpha_{1D+KIVA}$ proteins can be isolated from cells or tissue sources by an appropriate purification scheme using standard protein purification techniques. In another embodiment, $\alpha_{1D+KIVA}$ proteins are produced by recombinant DNA techniques. Alternative to recombinant expression, an $\alpha_{1D+KIVA}$ protein or polypeptide can be synthesized chemically using standard peptide synthesis techniques.

An "isolated" or "purified" protein or biologically active portion thereof is substantially free of cellular material or other contaminating proteins from the cell or tissue source from which the $\alpha_{1D+KIVA}$ protein is derived, or substantially free from chemical precursors or other chemicals when chemically synthesized. The language "substantially free of cellular material" includes preparations of $\alpha_{1D+KIVA}$ protein in which the protein is separated from cellular components of the cells from which it is isolated or recombinantly produced. In one embodiment, the language "substantially free of cellular material" includes preparations of $\alpha_{1D+KIVA}$ protein having less than about 30% (by dry weight) of non-$\alpha_{1D+KIVA}$ protein (also referred to herein as a "contaminating protein"), more preferably less than about 20%, 10%, or 5% of non-$\alpha_{1D+KIVA}$ protein. When the $\alpha_{1D+KIVA}$ protein or biologically active portion thereof is recombinantly produced, it is also preferably substantially free of culture medium, i.e., culture medium represents less than about 20%, 10%, or 5% of the volume of the protein preparation.

The language "substantially free of chemical precursors or other chemicals" includes preparations of $\alpha_{1D+KIVA}$ protein in which the protein is separated from chemical precursors or other chemicals which are involved in the synthesis of the protein. In one embodiment, the language "substantially free of chemical precursors or other chemicals" includes preparations of $\alpha_{1D+KIVA}$ protein having less than about 30%, 20%, 10%, or 5% (by dry weight) of chemical precursors or non-$\alpha_{1D+KIVA}$ chemicals.

As used herein, a "biologically active portion" of an $\alpha_{1D+KIVA}$ protein includes a fragment of an $\alpha_{1D+KIVA}$ protein which participates in an interaction between an $\alpha_{1D+KIVA}$ molecule and a non-$\alpha_{1D+KIVA}$ molecule. Biologically active portions of an $\alpha_{1D+KIVA}$ protein include peptides comprising amino acid sequences sufficiently homologous to or derived from the amino acid sequence of the $\alpha_{1D+KIVA}$ protein, e.g., the amino acid sequence shown in SEQ ID NO: 2 or SEQ ID NO: 4, which include less amino acids than the full length $\alpha_{1D+KIVA}$ proteins, and exhibit at least one activity of an $\alpha_{1D+KIVA}$ protein. Typically, biologically active portions comprise a domain or motif with at least one activity of the $\alpha_{1D+KIVA}$ protein, e.g., binding of a β, γ, or $\alpha_2/\delta$ calcium channel subunit. Biologically active portions of an $\alpha_{1D+KIVA}$ protein can be used as targets for developing agents which modulate a calcium channel mediated activity.

In one embodiment, a biologically active portion of an $\alpha_{1D-KIVA}$ protein comprises at least one transmembrane domain. Biologically active portions of $\alpha_{1D-KIVA}$ proteins mediate an $\alpha_{1D-KIVA}$ subunit activity and include one or more features of an $\alpha_{1D-KIVA}$ subunit protein, e.g., a KIVA sequence (SEQ ID NO: 2), and/or the absence of the amino acid sequence of SEQ ID NO: 8 and/or SEQ ID NO: 10. Biologically active portions, in which other regions of the protein are deleted, can be prepared by recombinant techniques and evaluated for one or more of the functional activities of a native $\alpha_{1D-KIVA}$ protein.

In one embodiment, the $\alpha_{1D+KIVA}$ protein has an amino acid sequence shown in SEQ ID NO: 2 or SEQ ID NO: 4, or is substantially homologous to SEQ ID NO: 2 or SEQ ID NO: 4, and retains the functional activity of the protein of SEQ ID NO: 4, yet differs in amino acid sequence due to natural allelic variation or mutagenesis, as described in detail in the section on nucleotides.

Accordingly, in another embodiment, the $\alpha_{1D+KIVA}$ protein is a protein which comprises an amino acid sequence at least about 50%, 75%, 85%, 95%, 99% or more homologous to SEQ ID NO: 2 or SEQ ID NO: 4.

To determine the percent homology of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence and non-homologous sequences can be disregarded for comparison purposes). The length of a reference sequence aligned for comparison purposes can be at least 50%, even 70%, 80%, or 90% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

The comparison of sequences and determination of percent homology between two sequences can be accomplished using a mathematical algorithm. A preferred, non-limiting example of a mathematical algonthim utilized for the comparison of sequences is the algorithm of Karlin and Altschul *Proc. Natl. Acad. Sci. USA* 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. *J. Mol. Biol.* 215: 403-10, 1990. BLAST nucleotide searches can be performed with the NBLAST program, score=100, wordlength=12 to obtain nucleotide sequences homologous to $\alpha_{1D+KIVA}$ nucleic acid molecules of the invention. BLAST protein searches can be performed with the XBLAST program, score=50, wordlength=3 to obtain amino acid sequences homologous to $\alpha_{1D+KIVA}$ protein molecules of the invention. To obtain gapped alignments for comparison purposes, Gapped BLAST can be utilized as described in Altschul et al., *Nucleic Acids Res.* 25(17): 3389-3402, 1997. When utilizing BLAST and Gapped BLAST programs, the default parameters of the respective programs (e.g., XBLAST and NBLAST) can be used. See the website for the National Center for Biotechnology Information. Another non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAMI120 weight residue table, a gap length penalty of 12, and a gap penalty of 4 can be used.

The invention also provides $\alpha_{1D-KIVA}$ chimeric or fusion proteins. As used herein, an $\alpha_{1D-KIVA}$ "chimeric protein" or "fusion protein" comprises an $\alpha_{1D-KIVA}$ polypeptide operativelylinked to a non-$\alpha_{1D-KIVA}$ polypeptide. An "$\alpha_{1D-KIVA}$ polypeptide" refers to a polypeptide havingan amino acid sequence corresponding to $\alpha_{1D-KIVA}$, whereas a "non-$\alpha_{1D-KIVA}$ polypeptide" refersto a polypeptide having an amino acid sequence corresponding to a protein which is notsubstantially homologous to the $\alpha_{1D-KIVA}$ protein, e.g., a protein which is different from the $\alpha_{1D-KIVA}$ protein and which is derived from the same or a different organism, or a protein which doesnot contain one or more of the features of the $\alpha_{1D-KIVA}$ proteins described herein, such as thepresence of a KIVA sequence (SEQ ID NO: 2), and the absence of the sequences of SEQ ID NO: 8 and/or SEQ ID NO: 10. Within an $\alpha_{1D-KIVA}$ fusion protein the $\alpha_{1D-KIVA}$ polypeptide cancorrespond to all or a portion of an $\alpha_{1D-KIVA}$ protein. In a preferred embodiment, an $\alpha_{1D-KIVA}$ fusion protein comprises at least one biologically active portion of an $\alpha_{1D-KIVA}$ protein. In anotherpreferred embodiment, an $\alpha_{1D-KIVA}$ fusion protein comprises at least two biologically activeportions of an $\alpha_{1D-KIVA}$ protein. Within the fusion protein, the term "operatively linked" isintended to indicate that the $\alpha_{1D-KIVA}$ polypeptide and the non-$\alpha_{1D-KIVA}$ polypeptide are fused in-frame to each other. The non-$\alpha_{1D-KIVA}$ polypeptide can be fused to the N-terminus or C-terminusof the $\alpha_{1D-KIVA}$ polypeptide.

For example, in one embodiment, the fusion protein is a GST-$\alpha_{1D+KIVA}$ fusion protein in which the $\alpha_{1D+KIVA}$ sequences are fused to the C-terminus of the GST sequences. Such fusion proteins can facilitate the purification of recombinant $\alpha_{1D+KIVA}$ In another embodiment, the fusion protein is an $\alpha_{1D+KIVA}$ protein containing a heterologous signal sequence at its N-terminus. In certain host cells (e.g., mammalian host cells), expression of $\alpha_{1D+KIVA}$ can be increased through use of a heterologous signal sequence.

The $\alpha_{1D+KIVA}$ fusion proteins of the invention can be incorporated into pharmaceutical compositions and administered to a subject in vivo. The $\alpha_{1D+KIVA}$ fusion proteins can be used to affect the bioavailability of an $\alpha_{1D+KIVA}$ substrate. Use of $\alpha_{1D+KIVA}$ fusion proteins may be useful therapeutically for the treatment of disorders related to calcium channel activity, e.g., cardiovascular disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia.

Moreover, the $\alpha_{1D+KIVA}$-fusion proteins of the invention can be used as immunogens to produce anti-$\alpha_{1D+KIVA}$ antibodies in a subject, to purify $\alpha_{1D+KIVA}$ ligands and in screening assays to identify molecules which inhibit the interaction of $\alpha_{1D+KIVA}$ with an $\alpha_{1D+KIVA}$ substrate.

An $\alpha_{1D+KIVA}$ chimeric or fusion protein of the invention can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. The fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST polypeptide). An $\alpha_{1D+KIVA}$-encoding nucleic acid can be cloned into such an expression vector such that the fusion moiety is linked in-frame to the $\alpha_{1D+KIVA}$ protein.

The present invention also pertains to variants of the $\alpha_{1D+KIVA}$ proteins which function as either $\alpha_{1D+KIVA}$ agonists (mimetics) or as $\alpha_{1D+KIVA}$ antagonists. Variants of the $\alpha_{1D+KIVA}$ proteins can be generated by mutagenesis, e.g., discrete point mutation or truncation of an $\alpha_{1D+KIVA}$ protein. An agonist of the $\alpha_{1D+KIVA}$ proteins can retain substantially the same, or a subset, of the biological activities of the naturally occurring form of an $\alpha_{1D+KIVA}$ protein. An antagonist of an $\alpha_{1D+KIVA}$ protein can inhibit one or more of the activities of the naturally occurring form of the $\alpha_{1D+KIVA}$ protein by, for example, competitively modulating a calcium channel mediated activity of an $\alpha_{1D+KIVA}$ protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the $\alpha_{1D+KIVA}$ protein.

In one embodiment, variants of an $\alpha_{1D+KIVA}$ protein which function as either $\alpha_{1D+KIVA}$ agonists (mimetics) or as $\alpha_{1D+KIVA}$ antagonists can be identified by screening combinatorial libraries of mutants, e.g., truncation mutants, of an $\alpha_{1D+KIVA}$ protein for $\alpha_{1D+KIVA}$ protein agonist or antagonist activity. In one embodiment, a variegated library of $\alpha_{1D+KIVA}$ variants is generated by combinatorial mutagenesis at the nucleic acid level and is encoded by a variegated gene library. A variegated library of $\alpha_{1D+KIVA}$ variants can be produced by, for example, enzymatically ligating a mixture of synthetic oligonucleotides into gene sequences such that a degenerate set of potential $\alpha_{1D+KIVA}$ sequences is expressible as individual polypeptides, or alternatively, as a set of larger fusion proteins (e.g., for phage display) containing the set of $\alpha_{1D+KIVA}$ sequences therein. There are a variety of methods that can be used to produce libraries of potential $\alpha_{1D+KIVA}$ variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential $\alpha_{1D+KIVA}$ sequences. Methods for synthesizing degenerate oligonucleotides are known in the art (see, e.g., Narang, S. A. *Tetrahedron* 39:3, 1983; Itakura et al. *Annu. Rev. Biochem.* 53:323, 1984; Itakura et al. *Science* 198:1056, 1984; Ike et al. *Nucleic Acid Res.* 11:477, 1983.

In addition, libraries of fragments of an $\alpha_{1D+KIVA}$ protein coding sequence can be used to generate a variegated population of $\alpha_{1D+KIVA}$ fragments for screening and subsequent selection of variants of an $\alpha_{1D+KIVA}$ protein.

The $\alpha_{1D+KIVA}$ proteins described herein can be directly or indirectly labeled with a detectable substance to facilitate detection of the bound or unbound binding agent. Suitable detectable substances include various enzymes, prosthetic groups, fluorescent materials, luminescent materials and radioactive materials.

An isolated $\alpha_{1D+KIVA}$ protein, or a portion or fragment thereof, can be used as an immunogen to generate antibodies that bind $\alpha_{1D+KIVA}$ using standard techniques for polyclonal and monoclonal antibody preparation. A full-length $\alpha_{1D+KIVA}$ protein can be used or, alternatively, the invention provides antigenic peptide fragments of $\alpha_{1D+KIVA}$ for use as immunogens. The antigenic peptide of $\alpha_{1D+KIVA}$ comprises the amino acid sequence of SEQ ID NO: 2, or at least 8 amino acid residues of the amino acid sequence shown in SEQ ID NO: 4, particularly in the regions of $\alpha_{1D+KIVA}$ which are distinct from the amino acid sequence of SEQ ID NO: 6, and encompasses an epitope of $\alpha_{1D+KIVA}$ such that an antibody raised against the peptide forms a specific immune complex with $\alpha_{1D+KIVA}$. Preferably, the antigenic peptide comprises at least 10, 15, 20 or 30 amino acid residues. An $\alpha_{1D+KIVA}$ immunogen typically is used to prepare antibodies by immunizing a suitable subject, (e.g., rabbit, goat, mouse or other mammal) with the immunogen. An appropriate immunogenic preparation can contain, for example, recombinantly expressed $\alpha_{1D+KIVA}$ protein or a chemically synthesized $\alpha_{1D+KIVA}$ polypeptide. The preparation can further include an adjuvant, such as Freund's complete or incomplete adjuvant, or similar immunostimulatory agent. Immunization of a suitable subject with an immunogenic $\alpha_{1D+KIVA}$ preparation induces a polyclonal antix-$\alpha_{1D+KIVA}$ antibody response.

Accordingly, another aspect of the invention pertains to anti-$\alpha_{1D+KIVA}$ antibodies. The term "antibody" as used herein refers to immunoglobulin molecules and immunologically active portions of immunoglobulin molecules, i.e., molecules that contain an antigen binding site which specifically binds (immunoreacts with) an antigen, such as $\alpha_{1D+KIVA}$. Examples of immunologically active portions of immunoglobulin molecules include F(ab) and $F(ab')_2$ fragments which can be generated by treating the antibody with an enzyme such as pepsin. The invention provides polyclonal and monoclonal antibodies that bind $\alpha_{1D+KIVA}$. The term "monoclonal antibody" or "monoclonal antibody composition", as used herein, refers to a population of antibody molecules that contain only one species of an antigen binding site capable of immunoreacting with a particular epitope of $\alpha_{1D+KIVA}$. A monoclonal antibody composition thus typically displays a single binding affinity for a particular $\alpha_{1D+KIVA}$ protein with which it immunoreacts.

Polyclonal anti-$\alpha_{1D+KIVA}$ antibodies can be prepared as described above by immunizing a suitable subject with an $\alpha_{1D+KIVA}$ immunogen. The anti-$\alpha_{1D+KIVA}$ antibody titer in the immunized subject can be monitored over time by standard techniques, such as with an enzyme linked immunosorbent assay (ELISA) using immobilized $\alpha_{1D+KIVA}$. If desired, the antibody molecules directed against $\alpha_{1D+KIVA}$ can be isolated from the mammal (e.g., from the blood) and further purified by known techniques, such as protein A chromatography to obtain the IgG fraction. At an appropriate time after immunization, e.g., when the anti-$\alpha_{1D+KIVA}$ antibody titers are highest, antibody-producing cells can be obtained from the subject and used to prepare monoclonal antibodies by standard techniques, such as the hybridoma technique originally described by Kohler and Milstein (1975) *Nature* 256:495497) (see also, Brown et al. *J. Immunol.* 127:539-46, 1981; Brown et al. *J. Biol. Chem.* 255:4980-83, 1980; Yeh et al. *Proc. Natl. Acad. Sci. USA* 76:2927-31, 1976; and Yeh et al. *Int. J. Cancer* 29:269-75, 1982), the more recent human B cell hybridoma technique (Kozbor et al. *Immunol Today* 4:72, 1983), the EBV-hybridoma technique (Cole et al. Monoclonal Antibodies and Cancer Therapy, Alan R. Liss, Inc., pp. 77-96, 1985) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner Yale *J. Biol. Med.,* 54:387-402, 1981; M. L. Gefter et al. Somatic Cell Genet. 3:231-36, 1977). Briefly, an immortal cell line (typically a myeloma) is fused to lymphocytes (typically splenocytes) from a mammal immunized with an $\alpha_{1D+KIVA}$ immunogen as described above, and the culture supernatants of the resulting hybridoma cells are screened to identify a hybridoma producing a monoclonal antibody that binds $\alpha_{1D+KIVA}$.

Any of the many well known protocols used for fusing lymphocytes and immortalized cell lines can be applied for the purpose of generating an anti-$\alpha_{1D+KIVA}$ monoclonal antibody (see, e.g., G. Galfre et al. *Nature* 266:55052, 1977; Gefter et al. *Somatic Cell Genet.,* cited supra; Lemer, Yale *J. Biol. Med.,* cited supra; Kenneth, Monoclonal Antibodies, cited supra). Moreover, the skilled worker will appreciate that there are many variations of such methods which also would be useful.

Alternative to preparing monoclonal antibody-secreting hybridomas, a monoclonal anti-$\alpha_{1D+KIVA}$ antibody can be identified and isolated by screening a recombinant combinatorial immunoglobulin library (e.g., an antibody phage display library) with $\alpha_{1D+KIVA}$ to thereby isolate immunoglobulin library members that bind $\alpha_{1D+KIVA}$. Kits for generating and screening phage display libraries are commercially available (e.g., the Pharmacia Recombinant Phage Antibody System, Catalog No. 27-9400-01). Additionally, examples of methods and reagents particularly amenable for use in generating and screening antibody display libraries can be found in, for example, Ladner et al. U.S. Pat. No. 5,223,409; Kang et al. PCT International Publication No. WO 92/18619; and McCafferty et al. *Nature* 348:552-554, 1990.

Additionally, recombinant anti-o:I+KIVA antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. *Science* 240:1041-1043, 1988; Liu et al. *Proc. Natl. Acad. Sci. USA* 84:3439-3443, 1987; Liu et al. *J. Immunol.* 139:3521-3526, 1987; Sun et al. *Proc. Natl. Acad. Sci. USA* 84:214-218, 1987; Nishimura et al. *Canc. Res.* 47:999-1005, 1987; Wood et al. *Nature* 314:446-449, 1985; and Shaw et al. *J. Natl. Cancer Inst.* 80:1553-1559, 1988); Morrison, S. L. *Science* 229:1202-1207, 1985; Oi et al. *BioTechniques* 4:214, 1986; Winter U.S. Pat. No. 5,225,539; Jones et al. *Nature* 321:552-525, 1986; Verhoeyan et al. *Science* 239:1534, 1988; and Beidler et al. *J. Immunol.* 141:4053-4060, 1988.

An anti-$\alpha_{1D+KIVA}$ antibody (e.g., monoclonal antibody) can be used to isolate $\alpha_{1D+KIVA}$ by standard techniques, such as affinity chromatography or immunoprecipitation. An anti-$\alpha_{1D+KIVA}$ antibody can facilitate the purification of natural $\alpha_{1D+KIVA}$ from cells and of recombinantly produced $\alpha_{1D+KIVA}$ expressed in host cells. Moreover, an anti-$\alpha_{1D+KIVA}$ antibody can be used to detect $\alpha_{1D+KIVA}$ protein (e.g., in a cellular lysate or cell supernatant) in order to evaluate the abundance and pattern of expression of the $\alpha_{1D+KIVA}$ protein. Anti-$\alpha_{1D+KIVA}$ antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{35}$S, or $^{3}$H.

Recombinant Expression Vectors and Host Cells

Another aspect of the invention pertains to vectors, preferably expression vectors, containing a nucleic acid encoding an O$\alpha_{1D+KIVA}$ protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other types of vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. Herein, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., $\alpha_{1D+KIVA}$ proteins, mutant forms of $\alpha_{1D+KIVA}$ proteins, fusion proteins, and the like).

The recombinant expression vectors of the invention can be designed for expression of $\alpha_{1D+KIVA}$ proteins in prokaryotic or eukaryotic cells. For example, $\alpha_{1D+KIVA}$ proteins can be expressed in bacterial cells such as *E. coli*, insect cells (using baculovirus expression vectors), yeast cells, amphibian cells, or mammalian cells. Suitable host cells are discussed further in Goeddel, Gene Expression Technology: Methods in Enzymology 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins.

Purified fusion proteins can be utilized in $\alpha_{1D+KIVA}$ activity assays, (e.g., direct assays or competitive assays described in detail below), or to generate antibodies specific for $\alpha_{1D+KIVA}$, for example.

In another embodiment, the $\alpha_{1D+KIVA}$ expression vector is a yeast expression vector: Examples of vectors for expression in yeast *S. cerivisae* include pYepSec1 (Baldari, et al., (1987) *EMBO J.* 6:229-234), pMFa (Kuijan and Herskowitz, *Cell* 30:933-943, 1982), pJRY88 (Schultz et al., *Gene* 54:113-123, 1987), pYES2 (Invitrogen Corporation, San Diego, Calif.), and picZ (InVitrogen Corp, San Diego, Calif.).

Alternatively, $\alpha_{1D+KIVA}$ proteins can be expressed in insect cells using baculovirus expression vectors. Baculovirus vectors available for expression of proteins in cultured insect cells (e.g., Sf9 cells) include the pAc series (Smith et al. *Mol. Cell Biol.* 3:2156-2165, 1983) and the pVL series (Lucklow and Summers *Virol.* 170:31-39, 1989).

In yet another embodiment, a nucleic acid of the invention is expressed in mammalian cells using a mammalian expression vector. Examples of mammalian expression vectors include pCDM8 (Seed, B. *Nature* 329:840, 1987) and pMT2PC (Kaufman et al. *EMBO J.* 6:187-195, 1987). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. Molecular Cloning: A Laboratory Manual. 2nd, ed, Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. *Genes Dev.* 1:268-277, 1987), lymphoid-specific promoters (Calame and Eaton *Adv. Immunol.* 43:235-275, 1988), in particular promoters of T cell receptors (Winoto and Baltimore *EMBO J.* 8:729-733, 1989) and immunoglobulins (Banerji et al. *Cell* 33:729-740, 1983; Queen and Baltimore *Cell* 33:741-748, 1983), neuron-specific promoters (e.g., the neurofilament promoter; Byrne and Ruddle *Proc. Natl. Acad. Sci. USA* 86:5473-5477, 1989), pancreas-specific promoters (Edlund et al. *Science* 230:912-916, 1985), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss *Science* 249:374-379, 1990 and the α-fetoprotein promoter (Campes and Tilghman *Genes Dev.* 3:537-546, 1989).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to $\alpha_{1D+KIVA}$ mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Trends in Genet., Vol.* 1(1) 1986.

Another aspect of the invention pertains to host cells into which a nucleic acid, e.g., an $\alpha_{1D+KIVA}$ mRNA, or a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an $\alpha_{1D+KIVA}$ protein can be expressed in bacterial cells such as *E. coli*, insect cells, yeast cells, Xenopus cells, e.g., Xenopus oocytes, or mammalian cells (such as Chinese hamster ovary cells (CHO) or COS cells). Other suitable host cells are known to those skilled in the art.

Vector DNA can be introduced into prokaryptic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (Molecular Cloning: A Laboratory Manual. 2nd, ed, Cold Spring Harbor Laboratory, Cold Spring Harbor Laboratory Press, Cold Spring Harbor, N.Y., 1989), and other laboratory manuals. Nucleic acids can also be introduced by microinjection.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an $\alpha_{1D+KIVA}$ protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) an $\alpha_{1D+KIVA}$ protein. Accordingly, the invention further provides methods for producing an $\alpha_{1D+KIVA}$ protein using the host cells of the invention.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. *Proc. Natl. Acad Sci. USA* 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express $\alpha_{1D+KIVA}$ protein (e.g., via a recombinant expression vector in a host cell in gene therapy applications), to detect $\alpha_{1D+KIVA}$ mRNA (e.g., in a biological sample) or a genetic alteration in a gene encoding an $\alpha_{1D+KIVA}$ protein, and to modulate $\alpha_{1D+KIVA}$ activity, as described further below. The $\alpha_{1D+KIVA}$ proteins can be used to treat disorders characterized by insufficient or excessive production of an $\alpha_{1D+KIVA}$ substrate or production of $\alpha_{1D+KIVA}$ inhibitors. In addition, the $\alpha_{1D+KIVA}$ proteins can be used to screen for naturally occurring $\alpha_{1D+KIVA}$ substrates, to screen for drugs or compounds which modulate $\alpha_{1D+KIVA}$ activity, as well as to treat disorders characterized by insufficient or excessive production of $\alpha_{1D+KIVA}$ protein or production of $\alpha_{1D+KIVA}$ protein forms which have decreased or aberrant activity compared to $\alpha_{1D+KIVA}$ wild type protein, e.g., cardiovascular disorders such as arteriosclerosis, ischemia reperfusion injury, restenosis, arterial inflammation, vascular wall remodeling, ventricular remodeling, rapid ventricular pacing, coronary microembolism, tachycardia, bradycardia, pressure overload, aortic bending, coronary artery ligation, vascular heart disease, atrial fibrilation, long-QT syndrome, congestive heart failure, sinus node disfunction, angina, heart failure, hypertension, atrial fibrillation, atrial flutter, dilated cardiomyopathy, idiopathic cardiomyopathy, myocardial infarction, coronary artery disease, coronary artery spasm, or arrhythmia. Moreover, the anti-$\alpha_{1D+KIVA}$ antibodies of the invention can be used to detect and isolate $\alpha_{1D+KIVA}$ proteins and modulate $\alpha_{1D+KIVA}$ activity.

Screening Assays

The invention provides methods for identifying modulators, i.e., candidate or test compounds or agents (e.g., proteins, peptides, peptidomimetics, peptoids, small molecules or other drugs) which bind to calcium channels comprising an $\alpha_{1D+KIVA}$ subunit described herein. Compounds thus identified can be used to modulate the activity of these calcium channels e.g., in a therapeutic protocol.

In one embodiment, the invention provides assays for screening test compounds which are substrates of calcium channels that include an $\alpha_{1D+KIVA}$ subunit described herein, or a biologically active portion of the subunit. In another embodiment, the invention provides assays for screening candidate or test compounds that bind to or modulate an activity of these calcium channels.

Ion channel-modulating compounds can be identified through both in vitro (e.g., cell and non-cell based) and in vivo methods. In one embodiment, $Ca^{2+}$ influx assays are used to measure calcium channel activity. Assays that measure changes in $Ca^{2+}$ concentration are known in the art. For example, the test system can be loaded with a detectable, $Ca^{2+}$-sensitive agent. Detection of the $Ca^{2+}$-sensitive agent in the following treatment with a test compound can give an indication of a change in $Ca^{2+}$ concentration. In one embodiment, the assay involves detection of calcium following stimulation by application of a voltage to the test system (e.g., a cell or an enclosed membrane preparation).

Assays to measure ion channel activity include flux assays, patch-clamp electrophysiology, and two electrode voltage clamp electrophysiology (see, e.g., Lin et al., Neuron 18:153-166, 1997). Patch-clamp physiology can be performed as follows. Briefly, a pipette tip containing a small electrode is pressed against a cell membrane to create a tight seal between the pipette and the membrane. The electrode captures the ions flowing through the membrane defined by the edges of the pipette tip. Various configurations can be employed to measure currents within the cell or within a patch of membrane or over the entire cell.

Two electrode voltage-clamp (TEVC) physiology can be performed as follows. Briefly, two sharp microelectrodes are pressed through a cell membrane. One electrode monitors membrane potential and the other electrode injects current to hold the membrane potential at the desired level. Both patch-clamp and TEVC techniques provide information regarding both kinetics and intensity of ion channel currents.

In one embodiment, calcium channel modulation is assayed using a Xenopus oocyte system. For a detailed description of transient expression of calcium channels and and recording from Xenopus oocytes, see, e.g., Xu and Lipscombe, J. Neurosci. 21(16):5944-5951, 2001; Lin et al., supra). In another embodiment, the assay is a mammalian-cell based assay, e.g., using a human or mouse cell.

Compounds

The test compounds of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al., J. Med. Chem. 37:2678-85, 1994); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, Anticancer Drug Des. 12:145, 1997).

Examples of methods for the synthesis of molecular libraries can be found in the art, for example in: DeWitt et al., Proc. Natl. Acad. Sci. U.S.A. 90:6909, 1993; Erb et al., Proc. Natl. Acad. Sci. USA 91:11422, 1994; Zuckermann et al., J. Med. Acad. Chem. 37:267 8, 1994; Cho et al., Science 261:1303, 1993; Carrell et al., Angew. Chem. Int. Ed. Engl. 33:2059, 1994; Carell et al., Angew. Chem. Int. Ed. Engl. 33:2061, 1994; and Gallop et al., J. Med. Chem. 37:1233, 1994.

Libraries of compounds may be presented in solution (e.g., Houghten, Biotechniques 13:412-421, 1992), or on beads (Lam, Nature 354:82-84, 1991), chips (Fodor, Nature 364: 555-556, 1993), bacteria (Ladner, U.S. Pat. No. 5,223,409), spores (Ladner U.S. Pat. No. 5,223,409), plasmids (Cull et al., Proc Natl Acad Sci USA 89:1865-1869, 1992) or on phage (Scott and Smith, Science 249:386-390, 1990; Devlin, Science 249:404-406, 1990; Cwirla et al. Proc. Natl. Acad. Sci. 87:6378-6382, 1990; Felici, J. Mol. Biol. 222:301-310, 199 1; Ladner supra.).

Chemical compounds to be used as test compounds (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In one aspect the compounds are organic small molecules, that is, compounds having molecular weight less than 1,000 amu, alternatively between 350-750 amu. In other aspects, the compounds are: (i) those that are non-peptidic; (ii) those having between 1 and 5, inclusive, heterocyclyl, or heteroaryl ring groups, which may bear further substituents; (iii) those in their respective pharmaceutically acceptable salt forms; or (iv) those that are peptidic.

The term "heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S monocyclic, bicyclic, or tricyclic, respectively), wherein 0, 1, 2 or 3 atoms of each ring can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring can be substituted by a substituent.

The term "substituents" refers to a group "substituted" on an alkyl, cycloalkyl, aryl, heterocyclyl, or heteroaryl group at any atom of that group. Suitable substituents include, without limitation, alkyl, alkenyl, alkynyl, alkoxy, halo, hydroxy, cyano, nitro, amino, $SO_3H$, perfluoroalkyl, perfluoroalkoxy, methylenedioxy, ethylenedioxy, carboxyl, oxo, thioxo, imino (alkyl, aryl, aralkyl), $S(O)_n$alkyl (where n is 0-2), $S(O)$n aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

Combinations of substituents and variables in compounds envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

Pharmaceutically acceptable salts of the compounds herein include those derived from pharmaceutically acceptable inorganic and organic acids and bases. Examples of suitable acid salts include acetate, adipate, alginate, aspartate, benzoate, benzenesulfonate, bisulfate, butyrate, citrate, digluconate, ethanesulfonate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, pectinate, persulfatephosphate, picrate, pivalate, propionate, salicylate, succinate, sulfate, tartrate, thiocyanate, tosylate and undecanoate.

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis-or trans-or E-or Z-double bond isomeric forms. All such isomeric forms of such compounds are expressly included in the present invention.

Binding Assays

The ability of the test compound to bind to a calcium channel comprising an $\alpha_{1D+KIVA}$ subunit can also be evaluated. While calcium channel binding is not a prerequisite for channel modulatory activity, compounds that bind a calcium channel can be useful in modulating activity of the channel. This can be accomplished, for example, by coupling the compound, e.g., the substrate, with a radioisotope or enzymatic label such that binding of the compound, e.g., the substrate, to calcium channels can be determined by detecting the labeled compound, e.g., substrate, in a complex. Alternatively, a calcium channel comprising an $\alpha_{1D+KIVA}$ subunit described herein could be coupled with a radioisotope or enzymatic label to monitor the ability of a test compound to modulate the complex. For example, compounds can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a test compound to interact with a calcium channel comprising an $\alpha_{1D}$ subunit or without the labeling of any of the interactants can be evaluated. For example, a microphysiometer can be used to detect the interaction of a compound with a calcium channel without the labeling of either the compound or the calcium channel (McConnell, H. M. et al., Science 257:1906-1912, 1992). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and calcium channel.

In yet another embodiment, a cell-free assay is provided in which a calcium channel described herein or biologically active portion thereof is contacted with a test compound and the ability of the test compound to bind to the channel or biologically active portion thereof is evaluated. Preferably, the cell-free assay comprises a membrane. Cell-free assays involve preparing a reaction mixture of the target gene protein and the test compound under conditions and for a time sufficient to allow the two components to interact and bind, thus forming a complex that can be removed and/or detected.

The interaction between two molecules can also be detected, e.g., using fluorescence energy transfer (FET) (see, for example, Lakowicz et al., U.S. Pat. No. 5,631,169; Stavrianopoulos et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of a test compound to bind to a calcium channel described herein can be accomplished using real-time Biomolecular Interaction Analysis (BIA) (see, e.g., Sjolander, S. and Urbaniczky, C., Anal. Chem. 63:2338-2345, 1991; and Szabo et al., Curr. Opin. Struct. Biol. 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

In one embodiment, the sample comprising the calcium channel or the test compound is anchored onto a solid phase. The channel/test compound complexes anchored on the solid phase can be detected at the end of the reaction.

It may be desirable to immobilize either the calcium channel, an anti-calcium channel antibody or its target molecule to facilitate separation of complexed from uncomplexed forms of one or both of the proteins, as well as to accommodate automation of the assay. Binding of a test compound to a calcium channel, or interaction of a calcium channel with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/$\alpha_{1D+KIVA}$ subunit fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and a sample comprising the calcium channel comprising the GST-tagged subunit, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above.

Other techniques for immobilizing a complex of calcium channel subunits on matrices include using conjugation of biotin and streptavidin. For example, biotinylated $\alpha_{1D+KIVA}$ subunit proteins can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with an epitope on the calcium channel but which do not interfere with binding of the channel to a target molecule. Such antibodies can be derivatized to the wells of the plate, and unbound target or calcium channels trapped in the wells by antibody conjugation. Methods for detecting such complexes, in addition to those described above for the GST-immobilized complexes, include immunodetection of complexes using antibodies reactive with a component of the calcium channel, as well as enzyme-linked assays which rely on detecting an enzymatic activity associated with the channel.

Alternatively, cell free assays can be conducted in a liquid phase. In such an assay, the reaction products are separated from unreacted components, by any of a number of standard techniques, including but not limited to: differential centrifugation (see, for example, Rivas, G., and Minton, A. P., Trends Biochem Sci 18:284-7, 1993); chromatography (gel filtration chromatography, ion-exchange chromatography); electrophoresis and immunoprecipitation (see, for example, Ausubel, F. et al., eds. (1999) Current Protocols in Molecular Biology, J. Wiley: New York). Such resins and chromatographic techniques are known to one skilled in the art (see, e.g., Heegaard, N. H., J Mol Recognit 11: 141-8, 1998; Hage, D. S., and Tweed, S. A., J Chromatogr B Biomed Sci Appl. 699:499-525, 1997). Further, fluorescence energy transfer may also be conveniently utilized, as described herein, to detect binding without further purification of the complex from solution. Preferably, cell free assays preserve the structure of the calcium channel complex, e.g., by including a membrane component or synthetic membrane components.

In a preferred embodiment, the assay includes contacting the calcium channel or channel comprising biologically active portions of the $\alpha_{1D+KIVA}$ subunit with a known compound which binds the channel to form an assay mixture, contacting the assay mixture with a test compound, and determining the ability of the test compound to interact with a calcium channel, wherein determining the ability of the test compound to interact with a calcium channel includes determining the ability of the test compound to preferentially bind to the calcium channel, or to modulate the activity of the channel, as compared to the known compound.

The calcium channels described herein can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. In an alternative embodiment, the invention provides methods for determining the ability of the test compound to modulate the activity of a calcium channel through modulation of the activity of a downstream effector of a calcium channel, e.g., a calcium-sensitive protein. For example, the activity of the calcium-sensitive molecule (e.g., a calcium-activated phosphatase, such as calcineurin, or a calcium-activated transcription factor) on an appropriate target (e.g., dephosphorylation of a substrate of calcinuerin, or DNA binding and transcriptional activation by a calcium-activated transcription factor) can be determined, or the binding of the calcium-sensitive molecule to an appropriate target can be determined, as previously described.

To identify compounds that interfere with the interaction between the calcium channel and an extracellular binding partner(s), a reaction mixture containing the target gene product and the binding partner is prepared, under conditions and for a time sufficient, to allow the two products to form a complex. In order to test an inhibitory agent, the reaction mixture is provided in the presence and absence of the test compound. The test compound can be initially included in the reaction mixture, or can be added at a time subsequent to the addition of the calcium channel and its cellular or extracellular binding partner. Control reaction mixtures are incubated without the test compound or with a placebo. The formation of any complexes between the calcium channel and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and a calcium channel comprising one or more mutant subunits. This comparison can be important in those cases wherein it is desirable to identify compounds that disrupt interactions of mutant but not normal target gene products.

These assays can be conducted in a heterogeneous or homogeneous format. Heterogeneous assays involve anchoring either the calcium channel or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the calcium channel subunits or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the calcium channel proteins or fragments thereof can be used as "bait proteins" in a two-hybrid assay or three-hybrid assay (see, e.g., U.S. Pat. No. 5,283, 317; Zervos et al., *Cell.*72:223-232, 1993; Madura et al., *J. Biol. Chem.* 268:12046-12054, 1993; Bartel et al., *Biotechniques* 14:920-924, 1993; Iwabuchi et al., *Oncogene* 8:1693-1696, 1993; and Brent WO94/10300), to identify other proteins, which bind to or interact with calcium channel proteins ("calcium channel-binding proteins" or "calcium channel-bp") and are involved in calcium channel activity. Such calcium channel-bps can be activators or inhibitors of signals by the calcium channels or calcium-sensitive targets as, for example, downstream elements of a calcium-mediated signaling pathway.

The two-hybrid system is based on the modular nature of most transcription factors, which consist of separable DNA-binding and activation domains. Briefly, the assay utilizes two different DNA constructs. In one construct, the gene that codes for a calcium channel $\alpha_{1D+KIV4}$ subunit protein or fragment thereof (e.g., corresponding to a soluble portion of an extracellular domain of the subunit) is fused to a gene encoding the DNA binding domain of a known transcription factor (e.g., GALA). In the other construct, a DNA sequence, from a library of DNA sequences, which encodes an unidentified protein ("prey" or "sample") is fused to a gene that codes for the activation domain of the known transcription factor. (Alternatively, the calcium channel subunit can be the fused to the activator domain.) If the "bait" and the "prey" proteins are able to interact, in vivo, forming a calcium channel subunit-dependent complex, the DNA-binding and activation domains of the transcription factor are brought into close proximity. This proximity allows transcription of a reporter gene (e.g., lacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with the calcium channel subunit.

In another embodiment, modulators of calcium channel subunit expression are identified. For example, a cell or cell free mixture is contacted with a candidate compound and the expression of calcium channel $\alpha_{1D+KIVA}$ subunit mRNA or protein evaluated relative to the level of expression of $\alpha_{1D+KIVA}$ mRNA or protein in the absence of the candidate compound. When expression of $\alpha_{1D+KIVA}$ mRNA or protein is greater in the presence of the candidate compound than in its absence, the candidate compound is identified as a stimulator of $\alpha_{1D+KIVA}$ mRNA or protein expression. Alternatively, when expression of $\alpha_{1D+KIVA}$ mRNA or protein is less (statistically significantly less) in the presence of the candidate compound than in its absence, the candidate compound is identified as an inhibitor of $\alpha_{1D+KIVA}$ mRNA or protein expression. The level of $\alpha_{1D+KIVA}$ mRNA or protein expression can be determined by methods described herein for detecting $\alpha_{1D+KIVA}$ mRNA or protein.

In another aspect, the invention pertains to a combination of two or more of the assays described herein. For example, a modulating agent can be identified using a cell-based or a cell free assay, and the ability of the agent to modulate the activity of a calcium channel can be confirmed in vivo, e.g., in an animal such as an animal model for a pain disorder or a disorder associated with stroke or traumatic brain injury.

This invention further pertains to novel agents identified by the above-described screening assays. Accordingly, it is within the scope of this invention to further use an agent identified as described herein (e.g., a calcium channel-modulating agent, an antisense nucleic acid molecule corresponding to one or more of the calcium channel subunits described herein, a calcium channel-specific antibody, or a calcium channel-binding partner) in an appropriate animal model to determine the efficacy, toxicity, side effects, or mechanism of action, of treatment with such an agent. Furthermore, novel agents identified by the above-described screening assays can be used for treatments as described herein.

Diagnostic and prognostic assays of the invention include methods for assessing the expression level of calcium channel $\alpha_{1D+KIVA}$ subunit and for identifying variations and mutations in the nucleotide or amino acid sequence of calcium channel $\alpha_{1D+KIVA}$ molecules.

Expression Monitoring and Profiling. The presence, level, or absence of calcium channel $\alpha_{1D+KIVA}$ subunit protein or nucleic acid in a biological sample can be evaluated by obtaining a biological sample from a test subject and contacting the biological sample with a compound or an agent capable of detecting calcium channel $\alpha_{1D+KIVA}$ subunit protein or nucleic acid (e.g., mRNA, genomic DNA) that encodes calcium channel $\alpha_{1+KIVA}$ subunit protein such that the presence of the protein or nucleic acid is detected in the biological sample. The term "biological sample" includes tissues, cells and biological fluids isolated from a subject, as well as tissues, cells and fluids present within a subject. A preferred biological sample is cardiac tissue. The level of expression of the calcium channel $\alpha_{1D+KIVA}$ gene can be measured in a number of ways, including, but not limited to: measuring the mRNA encoded by the calcium channel $\alpha_{1D+KIVA}$ gene; measuring the amount of protein encoded by the calcium channel $\alpha_{1D+KIVA}$ gene; or measuring the activity of the protein encoded by the calcium channel $\alpha_{1D+KIVA}$ subunit.

The level of mRNA corresponding to a calcium channel $\alpha_{1D+KIVA}$ gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length calcium channel $\alpha_{1D+KIVA}$ subunit nucleic acid, such as the nucleic acids described herein, or a portion thereof, such as an oligonucleotide of at least 7, 15, 30, 50, 100, 250 or 500 nucleotides in length and sufficient to specifically hybridize under stringent conditions to calcium channel $\alpha_{1D+KIVA}$ subunit mRNA or genomic DNA. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the calcium channel $\alpha_{1D+KIVA}$ genes.

The level of mRNA in a sample that is encoded by one of calcium channel $\alpha_{1D+KIVA}$ subunits can be evaluated with nucleic acid amplification, e.g., by rtPCR (Mullis (1987) U.S. Pat. No. 4,683,202), ligase chain reaction (Barany, *Proc. Natl. Acad. Sci. USA* 88:189-193, 1991), self sustained sequence replication (Guatelli et al., *Proc. Natl. Acad. Sci. USA* 87:1874-1878, 1990), transcriptional amplification system (Kwoh et al., *Proc. Natl. Acad. Sci. USA* 86:1173-1177, 1989), Q-Beta Replicase (Lizardi et al., *Bio/Technology* 6:1197, 1988), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the calcium channel $\alpha_{1D+KIVA}$ gene being analyzed.

In another embodiment, the methods herein include further contacting a control sample with a compound or agent capable of detecting calcium channel $\alpha_{1D+KIVA}$ subunit mRNA, or genomic DNA, and comparing the presence of calcium channel $\alpha_{1D+KIVA}$ mRNA or genomic DNA in the control sample with the presence of calcium channel $\alpha_{1D+KIVA}$ mRNA or genomic DNA in the test sample. In still another embodiment, serial analysis of gene expression, as described in U.S. Pat. No. 5,695,937, is used to detect calcium channel $\alpha_{1D+KIVA}$ transcript levels.

A variety of methods can be used to determine the level of protein encoded by calcium channel $\alpha_{1D+KIVA}$ genes. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect calcium channel $\alpha_{1D+KIVA}$ subunit protein in a biological sample in vitro as well as in vivo. In vitro techniques for detection of proteins include enzyme linked immunosorbent assays (ELISAs), immunoprecipitations, immunofluorescence, enzyme immunoassay (EIA), radioimmunoassay (RIA), and Western blot analysis. In vivo techniques for detection of proteins include introducing into a subject a labeled anti-calcium channel $\alpha_{1D+KIVA}$ subunit antibody. For example, the antibody can be labeled with a radioactive marker whose presence and location in a subject can be detected by standard imaging techniques. In another embodiment, the sample is labeled, e.g., biotinylated and then contacted to the antibody, e.g., an anti-calcium channel $\alpha_{1D+KIVA}$ subunit antibody positioned on an antibody array (as described below). The sample can be detected, e.g., with avidin coupled to a fluorescent label.

In another embodiment, the methods further include contacting the control sample with a compound or agent capable of detecting a calcium channel $\alpha_{1D+KIVA}$ protein, and comparing the presence of the protein in the control sample with the presence of the protein in the test sample.

The invention also includes kits for detecting the presence of calcium channel $\alpha_{1D+KIVA}$ subunit proteins in a biological sample. For example, the kit can include a compound or agent capable of detecting calcium channel $\alpha_{1D+KIVA}$ subunit protein or mRNA in a biological sample; and a standard. The compound or agent can be packaged in a suitable container. The kit can further comprise instructions for using the kit to detect calcium channel $\alpha_{1D+KIVA}$ subunit proteins or nucleic acids.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also include a buffering agent, a preservative, or a protein stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with calcium channel expression or activity. As used herein, the term "unwanted" includes an unwanted phenomenon involved in a biological response such as cardiac arrhythmia or ventricular fibrillation.

In one embodiment, a disease or disorder associated with calcium channel expression or activity is identified. A test sample is obtained from a subject and one or more calcium channel proteins or nucleic acids (e.g., mRNA or genomic DNA) are evaluated, wherein the level, e.g., the presence or absence, of a calcium channel protein or nucleic acid is diagnostic for a subject having or at risk of developing a disease or disorder associated with calcium channel expression or activity. As used herein, a "test sample" refers to a biological sample obtained from a subject of interest, including a biological fluid (e.g., serum), cell sample, or tissue, e.g., cardiac tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with calcium channel expression or activity. For example, such methods can be used to determine whether a subject can be effectively treated with an agent for a pain disorder or for stroke or traumatic brain injury.

In another aspect, the invention features a computer medium having a plurality of digitally encoded data records. Each data record includes a value representing the level of expression or activity of a calcium channel in a sample, and a descriptor of the sample. The descriptor of the sample can be an identifier of the sample, a compound which with the sample was treated, a subject from which the sample was derived (e.g., a patient), a diagnosis, or a treatment (e.g., a preferred treatment). In a preferred embodiment, the data record further includes values representing the level of expression of genes other than the calcium channel (e.g., other genes associated with a disorder related to activity of the calcium channel, or other genes on an array). The data record can be structured as a table, e.g., a table that is part of a database such as a relational database (e.g., a SQL database of the Oracle or Sybase database environments).

Also featured is a method of evaluating a sample. The method includes providing a sample, e.g., from the subject, and determining a gene expression profile of the sample, wherein the profile includes a value representing the level of calcium channel expression or activity. The method can further include comparing the value or the profile (i.e., multiple values) to a reference value or reference profile. The gene expression profile of the sample can be obtained by any of the methods described herein (e.g., by providing a nucleic acid from the sample and contacting the nucleic acid to an array, or by assaying the activity of a calcium channel in the sample). The method can be used to diagnose a cardiac disorder in a subject wherein a change in L-type calcium channel expression is an indication that the subject has or is disposed to having a cardiac disorder. The method can be used to monitor a treatment for cardiac, neuroendocrine, or neuronal (e.g., brain or peripheral neuronal) disorder in a subject. For example, the gene expression profile can be determined for a sample from a subject undergoing treatment. The profile can be compared to a reference profile or to a profile obtained from the subject prior to treatment or prior to onset of the disorder (see, e.g., Golub et al., *Science* 286:531, 1999).

In yet another aspect, the invention features a method of evaluating a test compound (see also, "Screening Assays", above). The method includes providing a cell and a test compound; contacting the test compound to the cell; obtaining a subject expression profile for the contacted cell; and comparing the subject expression profile to one or more reference profiles. The profiles include a value representing the level of calcium channel activity or expression. In a preferred embodiment, the subject activity or expression profile is compared to a target profile, e.g., a profile for a normal cell or for a desired condition of a cell. The test compound is evaluated favorably if the subject expression profile is more similar to the target profile than an expression profile obtained from an uncontacted cell.

In another aspect, the invention features, a method of evaluating a subject. The method includes: a) obtaining a sample from a subject, e.g., from a caregiver, e.g., a caregiver who obtains the sample from the subject; b) determining a subject expression profile for the sample. Optionally, the method further includes either or both of steps: c) comparing the subject expression profile to one or more reference expression profiles; and d) selecting the reference profile most similar to the subject reference profile. The subject expression profile and the reference profiles include a value representing the level of calcium channel activity or expression. A variety of routine statistical measures can be used to compare two reference profiles. One possible metric is the length of the distance vector that is the difference between the two profiles. Each of the subject and reference profile is represented as a multi-dimensional vector, wherein each dimension is a value in the profile.

The method can further include transmitting a result to a caregiver. The result can be the subject expression profile, a result of a comparison of the subject expression profile with another profile, a most similar reference profile, or a descriptor of any of the aforementioned. The result can be transmitted across a computer network, e.g., the result can be in the form of a computer transmission, e.g., a computer data signal embedded in a carrier wave.

Also featured is a computer medium having executable code for effecting the following steps: receive a subject expression profile (e.g., any subject expression profile described herein); access a database of reference expression profiles; and either i) select a matching reference profile most similar to the subject expression profile or ii) determine at least one comparison score for the similarity of the subject expression profile to at least one reference profile. The subject-expression profile, and the reference expression profiles each include a value representing the level of calcium channel activity or expression.

Arrays and Uses Thereof

In another aspect, the invention features an array that includes a substrate having a plurality of addresses. At least one address of the plurality includes a capture probe that binds specifically to a molecule corresponding to a calcium channel $\alpha_{1D+KIVA}$ subunit e.g., a calcium channel $\alpha_{1D+KIVA}$ nucleic acid or polypeptide. The array can have a density of at least 10, 100, 1,000, or 10,000 or more addresses/cm², and ranges between. The substrate can be a two-dimensional substrate such as a glass slide, a wafer (e.g., silica or plastic), a mass spectroscopy plate, or a three-dimensional substrate such as a gel pad. Addresses in addition to address of the plurality can be disposed on the array.

In a preferred embodiment, at least one address of the plurality includes a nucleic acid capture probe that hybridizes specifically to a calcium channel $\alpha_{1D+KIVA}$ nucleic acid, e.g., the sense or anti-sense strand. A subset of addresses of the plurality of addresses can be a nucleic acid capture probe for a calcium channel gene encoding a $\alpha_{1D+KIVA}$ subunit. Each address of the subset can include a capture probe that hybridizes to a different region of a calcium channel $\alpha_{1D+KIVA}$ nucleic acid. The array can be used to sequence the gene by hybridization (see, e.g., U.S. Pat. No. 5,695,940).

An array can be generated by various methods, e.g., by photolithographic methods (see, e.g., U.S. Pat. Nos. 5,143,854; 5,510,270; and 5,527,681), mechanical methods (e.g., directed-flow methods as described in U.S. Pat. No. 5,384,261), pin-based methods (e.g., as described in U.S. Pat. No. 5,288,514), and bead-based techniques (e.g., as described in PCT US/93/04145).

In another embodiment, at least one address of the plurality includes a polypeptide capture probe that binds specifically to a calcium channel $\alpha_{1D+KIVA}$ polypeptide or fragment thereof. The polypeptide can be a naturally-occurring interaction partner of a calcium channel $\alpha_{1D+KIVA}$ polypeptide. Preferably, the polypeptide is an antibody, e.g., an antibody described herein (see "Anti-calcium channel $\alpha_{1D+KIVA}$ Antibodies,"), such as a monoclonal antibody or a single-chain antibody.

In another aspect, the invention features a method of analyzing the expression of calcium channel $\alpha_{1D+KIVA}$ subunits. The method includes providing an array as described above; contacting the array with a sample and detecting binding of calcium channel $\alpha_{1D+KIVA}$ molecule (e.g., nucleic acid or polypeptide) to the array. Optionally the method further includes amplifying nucleic acid from the sample prior or during contact with the array.

In another embodiment, the array can be used to assay gene expression in a tissue to ascertain tissue specificity of genes in the array, particularly the expression of calcium channel $\alpha_{1D+KIVA}$ subunits. If a sufficient number of diverse samples is analyzed, clustering (e.g., hierarchical clustering, k-means clustering, Bayesian clustering and the like) can be used to identify other genes which are co-regulated with calcium channel $\alpha_{1D+KIVA}$ subunits. For example, the array can be used for the quantitation of the expression of multiple genes. Thus, not only tissue specificity, but also the level of expression of a battery of genes in the tissue is ascertained. Quantitative data can be used to group (e.g., cluster) genes on the basis of their tissue expression per se and level of expression in that tissue.

For example, array analysis of gene expression can be used to assess the effect of cell-cell interactions on calcium channel $\alpha_{1D+KIVA}$ subunit expression. A first tissue can be perturbed and nucleic acid from a second tissue that interacts with the first tissue can be analyzed. In this context, the effect of one cell type on another cell type in response to a biological stimulus can be determined, e.g., to monitor the effect of cell-cell interaction at the level of gene expression.

In another embodiment, cells are contacted with a therapeutic agent. The expression profile of the cells is determined using the array, and the expression profile is compared to the profile of like cells not contacted with the agent. For example, the assay can be used to determine or analyze the molecular basis of an undesirable effect of the therapeutic agent. If an agent is administered therapeutically to treat one cell type but has an undesirable effect on another cell type, the invention provides an assay to determine the molecular basis of the undesirable effect and thus provides the opportunity to co-administer a counteracting agent or otherwise treat the undesired effect. Similarly, even within a single cell type, undesirable biological effects can be determined at the molecular level. Thus, the effects of an agent on expression of other than the target gene can be ascertained and counteracted.

In another embodiment, the array can be used to monitor expression of one or more genes in the array with respect to time. For example, samples obtained from different time points can be probed with the array. Such analysis can identify and/or characterize the development of a disease or disorder associated with calcium channel activity. The method can also evaluate the treatment and/or progression of a calcium channel-associated disease or disorder.

The array is also useful for ascertaining differential expression patterns of one or more genes in normal and abnormal cells. This provides a battery of genes (e.g., including genes encoding calcium channel $\alpha_{1D+KIVA}$ subunits) that could serve as a molecular target for diagnosis or therapeutic intervention.

In another aspect, the invention features an array having a plurality of addresses. Each address of the plurality includes a unique polypeptide. At least one address of the plurality has disposed thereon a calcium channel $\alpha_{1D+KIVA}$ polypeptide or fragment thereof. Methods of producing polypeptide arrays are described in the art, e.g., in De Wildt et al., *Nature Biotech.* 18: 989-994, 2000; Lueking et al., *Anal. Biochem.* 270:103-111, 1999; Ge, H., *Nucleic Acids Res.* 28:e3, I-VII, 2000; MacBeath, G., and Schreiber, S. L., *Science* 289:1760-1763, 2000; and WO 99/51773A1. In a preferred embodiment, each addresses of the plurality has disposed thereon a polypeptide at least 60%-99% identical to a calcium channel $\alpha_{1D+KIVA}$ polypeptide or fragment thereof. For example, multiple variants of a calcium channel $\alpha_{1D+KIVA}$ polypeptide (e.g., encoded by allelic variants, site-directed mutants, random mutants, or combinatorial mutants) can be disposed at individual addresses of the plurality.

The polypeptide array can be used to detect a calcium channel-binding compound, e.g., an antibody in a sample from a subject with specificity for a calcium channel $\alpha_{1D+KIVA}$ polypeptide or the presence of a calcium channel-binding protein or ligand.

In another aspect, the invention features a method of analyzing a plurality of probes. The method is useful, e.g., for analyzing gene expression. The method includes: providing a two-dimensional array having a plurality of addresses, each address of the plurality being positionally distinguishable from each other address of the plurality having a unique capture probe, e.g., wherein the capture probes are from a cell or subject which express calcium channels comprising $\alpha_{1D+KIVA}$ subunits or from a cell or subject in which a calcium channel-mediated response has been elicited, e.g., by contact of the cell with calcium channel $\alpha_{1D+KIVA}$ nucleic acids or proteins, or administration to the cell or subject calcium channel $\alpha_{1D+KIVA}$ nucleic acids or proteins; providing a two dimensional array having a plurality of addresses, each address of the plurality being positionally distinguishable from each other address of the plurality, and each address of the plurality having a unique capture probe, e.g., wherein the capture probes are from a cell or subject which does not express calcium channel $\alpha_{1D+KIVA}$ subunits (or does not express as highly as in the case of the calcium channel $\alpha_{1D+KIVA}$ subunit-positive plurality of capture probes) or from a cell or subject which in which a calcium channel-mediated response has not been elicited (or has been elicited to a lesser extent than in the first sample); contacting the array with one or more inquiry probes (which is preferably other than a calcium channel $\alpha_{1D+KIVA}$ nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features a method of analyzing calcium channel $\alpha_{1D+KIVA}$ subunits, e.g., analyzing structure, function, or relatedness to other nucleic acid or amino acid sequences. The method includes: providing a calcium channel $\alpha_{1D+KIVA}$ nucleic acid or amino acid sequence; comparing the sequence(s) with one or more preferably a plurality of sequences from a collection of sequences, e.g., a nucleic acid or protein sequence database; to thereby analyze calcium channel $\alpha_{1D+KIVA}$ subunits.

Detection Assays

Portions or fragments of the cDNA sequences identified herein (and the corresponding complete gene sequences) can be used in numerous ways as polynucleotide reagents.

For example, polynucleotide reagents can be used for diagnostic assays, prognostic assays, and monitoring clinical trials are used for prognostic (predictive) purposes to thereby treat an individual prophylactically. Accordingly, one aspect of the present invention relates to diagnostic assays for determining $\alpha_{1D+KIVA}$ protein and/or nucleic acid expression as well as $\alpha_{1D+KIVA}$ activity, in the context of a biological sample (e.g., blood, serum, cells, tissue) to thereby determine whether an individual is afflicted with a disease or disorder, or is at risk of developing a disorder, associated with aberrant or unwanted $\alpha_{1D+KIVA}$ expression or activity. The invention also provides for prognostic (or predictive) assays for determining whether an individual is at risk of developing a disorder associated with $\alpha_{1D+KIVA}$ protein, nucleic acid expression or activity. For example, mutations in a gene encoding an $\alpha_{1D+KIVA}$ subunit can be assayed in a biological sample and used for prognostic or predictive purposes.

Another aspect of the invention pertains to monitoring the influence of agents (e.g., drugs, compounds) on the expression or activity of $\alpha_{1D+KIVA}$ in vivo.

Monitoring the influence of agents (e.g., drugs) on the expression or activity of an $\alpha_{1D+KIVA}$ subunit protein (e.g., the modulation of membrane excitability) can be applied not only in basic drug screening, but also in clinical trials. For example, the effectiveness of an agent determined by a screening assay as described herein to increase $\alpha_{1D+KIVA}$ gene expression, protein levels, or upregulate $\alpha_{1D+KIVA}$ activity, can be monitored in clinical trials of subjects exhibiting decreased or increased $\alpha_{1D+KIVA}$ gene expression, protein levels, or downregulated $\alpha_{1D+KIVA}$. Other genes that have been implicated in, for example, a calcium channel associated disorder can be used markers of the phenotype of a particular cell.

Therapeutic Methods

Another aspect of the invention pertains to methods of modulating $\alpha_{1D+KIVA}$ expression or activity for therapeutic purposes. Accordingly, in an exemplary embodiment, the modulatory method of the invention involves contacting a cell with an $\alpha_{1D+KIVA}$ subunit or agent that modulates one or more of the activities of $\alpha_{1D+KIVA}$ subunit protein activity associated with the cell. An agent that modulates $\alpha_{1D+KIVA}$ subunit protein activity can be an agent as described herein, such as a nucleic acid or a protein, a naturally-occurring target molecule of an $\alpha_{1D+KIVA}$ protein (e.g., an $\alpha_{1D+KIVA}$ substrate), an $\alpha_{1D+KIVA}$ antibody, an $\alpha_{1D+KIVA}$ agonist or antagonist, a peptidomimetic of an $\alpha_{1D+KIVA}$ agonist or antagonist, or other small molecule. In one embodiment, the agent stimulates one or more $\alpha_{1D+KIVA}$ activities. Examples of such stimulatory agents include active $\alpha_{1D+KIVA}$ protein and a nucleic acid molecule encoding $\alpha_{1D+KIVA}$ that has been introduced into the cell. In another embodiment, the agent inhibits one or more $\alpha_{1D+KIVA}$ activities. Examples of such inhibitory agents include antisense $\alpha_{1D+KIVA}$ nucleic acid molecules, anti-$\alpha_{1D+KIVA}$ antibodies, and $\alpha_{1D+KIVA}$ inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of an $\alpha_{1D+KIVA}$ protein or nucleic acid molecule. In one embodiment, the method involves administering an agent (e.g., an agent identified by a screening assay described herein), or combination of agents that modulates (e.g., upregulates or downregulates) $\alpha_{1D+KIVA}$ expression or activity. In another embodiment, the method involves administering an $\alpha_{1D+KIVA}$ protein or nucleic acid molecule as therapy to compensate for reduced or aberrant $\alpha_{1D+KIVA}$ expression or activity.

Stimulation of $\alpha_{1D+KIVA}$ activity is desirable in situations in which $\alpha_{1D+KIVA}$ is abnormally downregulated and/or in which increased $\alpha_{1D+KIVA}$ activity is likely to have a beneficial effect. Antagonism of activity may also be desirable. For example, modulators may be desirable for regulation of cardiac rhythm.

Pharmaceutical Compositions

As used herein, the compounds of this invention, e.g., calcium channel modulators identified by the methods described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, digluconate, dodecylsulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

The compositions delineated herein include the compounds of the formulae delineated herein, as well as additional therapeutic agents if present, in amounts effective for achieving a modulation of disease or disease symptoms, including ion channel-mediated disorders or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried cornstarch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan-monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds and methods described above can be used for the therapeutic modulation of calcium channel function.

TABLE 1

| Description | Sequence | SEQ ID NO. |
|---|---|---|
| Nucleotides encoding KIVA insert | AAAATTGTAGCG | SEQ ID NO: 1 |
| amino acid sequence (SEQ ID NO:2) of KIVA insert | SEQ ID NO: 2 | |
| nucleotide sequence (SEQ ID NO: 1) of novel $\alpha_{1D}$ calcium channel subunit | ATGATGATGATGATGATGATGAAAAAAATGCAGCATCAACGGCAGCAGCA<br>AGCGGACCACGCGAACGAGGCAAACTATGCAAGAGGCACCAGACTTCCTC<br>TTTCTGGTGAAGGACCAACTTCTCAGCCGAATAGCTCCAAGCAAACTGTC<br>CTGTCTTGGCAAGCTGCAATCGATGCTGCTAGACAGGCCAAGGCTGCCCA<br>AACTATGAGCACCTCTGCACCCCCACCTGTAGGATCTCTCTCCCAAAGAA<br>AACGTCAGCAATACGCCAAGAGCAAAAAACAGGGTAACTCGTCCAACAGC<br>CGACCTGCCCGCGCCCTTTTCTGTTTATCACTCAATAACCCCATCCGAAG<br>AGCCTGCATTAGTATAGTGGAATGGAAACCATTTGACATATTTATATTAT<br>TGGCTATTTTTGCCAATTGTGTGGCCTTAGCTATTTACATCCCATTCCCT<br>GAAGATGATTCTAATTCAACAAATCATAACTTGGAAAAAGTAGAATATGC<br>CTTCCTGATTATTTTTACAGTCGAGACATTTTTGAAGATTATAGCGTATG<br>GATTATTGCTACATCCTAATGCTTATGTTAGGAATGGATGGAATTTACTG<br>GATTTTGTTATAGTAATAGTAGGATTGTTTAGTGTAATTTTGGAACAATT<br>AACCAAAGAAACAGAAGGCGGGAACCACTCAAGCGGCAAATCTGGAGGCT<br>TTGATGTCAAAGCCCTCCGTGCCTTTCGAGTGTTGCGACCACTTCGACTA<br>GTGTCAGGAGTGCCCAGTTTACAAGTTGTCCTGAACTCCATTATAAAAGC<br>CATGGTTCCCCTCCTTCACATAGCCCTTTTGGTATTATTTGTAATCATAA<br>TCTATGCTATTATAGGATTGGAACTTTTTATTGGAAAAATGCACAAAACA<br>TGTTTTTTTGCTGACTCAGATATCGTAGCTGAAGAGGACCCAGCTCCATG<br>TGCGTTCTCAGGGAATGGACGCCAGTGTACTGCCAATGGCACGGAATGTA<br>GGAGTGGCTGGGTTGGCCCGAACGGAGGCATCACCAACTTTGATAACTTT<br>GCCTTTGCCATGCTTACTGTGTTTCAGTGCATCACCATGGAGGGCTGGAC | SEQ ID NO: 3 |

TABLE 1-continued

| Description | Sequence | SEQ ID NO. |
|---|---|---|
| | AGACGTGCTCTACTGGATGAATGATGCTATGGGATTTGAATTGCCCTGGG | |
| | TGTATTTTGTCAGTCTCGTCATCTTTGGGTCATTTTTCGTACTAAATCTT | |
| | GTACTTGGTGTATTGAGCGGAGAATTCTCAAAGGAAAGAGAGAAGGCAAA | |
| | AGCACGGGAGATTTCCAGAAGCTCCGGGAGAAGCAGCAGCTGGAGGAGG | |
| | ATCTAAAGGGCTACTTGGATTGGATCACCCAAGCTGAGGACATCGATCCG | |
| | GAGAATGAGGAAGAAGGAGGAGAGGAAGGCAAACGAAATACTAGCATGCC | |
| | CACCAGCGAGACTGAGTCTGTGAACACAGAGAACGTCAGCGGTGAAGGCG | |
| | AGAACCGAGGCTGCTGTGGAAGTCTCTGTCAAGCCATCTCAAAATCCAAA | |
| | CTCAGCCGACGCTGGCGTCGCTGGAACCGATTCAATCGCAGAAGATGTAG | |
| | GGCCGCCGTGAAGTCTGTCACGTTTTACTGGCTGGTTATCGTCCTGGTGT | |
| | TTCTGAACACCTTAACCATTTCCTCTGAGCACTACAATCAGCCAGATTGG | |
| | TTGACACAGATTCAAGATATTGCCAACAAAGTCCTCTTGGCTCTGTTCAC | |
| | CTGCGAGATGCTGGTAAAAATGTACAGCTTGGGCCTCCAAGCATATTTCG | |
| | TCTCTCTTTTCAACCGGTTTGATTGCTTCGTGGTGTGTGGTGGAATCACT | |
| | GAGACGATCTTGGTGGAACTGGAAATCATGTCTCCCCTGGGGATCTCTGT | |
| | GTTTCGGTGTGTGCGCCTCTTAAGAATCTTCAAAGTGACCAGGCACTGGA | |
| | CTTCCCTGTGCAACTTAGTGGCATCCTTATTAAACTCCATGAAGTCCAGT | |
| | GCTTCGCTGTTGCTTCTGCTTTTTCTCTTCATTATCATCTTTTCCTTGCT | |
| | TGGGATGCAGCTGTTTGGCGGCAAGTTTAATTTTGATGAAACGCAAACCA | |
| | AGCGGAGCACCTTTGACAATTTCCCTCAAGCACTTCTCACAGTGTTCCAG | |
| | ATCCTGACAGGCGAAGACTGGAATGCTGTGATGTACGATGGCATCATGGC | |
| | TTACGGGGGCCCATCCTCTTCAGGAATGATCGTCTGCATCTACTTCATCA | |
| | TCCTCTTCATTTGTGGTAACTATATTCTACTGAATGTCTTCTTGGCCATC | |
| | GCTGTAGACAATTTGGCTGATGCTGAAAGTCTGAACACTGCTCAGAAAGA | |
| | AGAAGCGGAAGAAAAGGAGAGGAAAAAGATTGCCAGAAAAGAGAGCCTAG | |
| | AAAATAAAAAGAACAACAAACCAGAAGTCAACCAGATAGCCAACAGTGAC | |
| | AACAAGGTTACAATTGATGACTATAGAGAAGAGGATGAAGACAAGGACCC | |
| | CTATCCGCCTTGCGATGTGCCAGTAGGGGAAGAGGAAGAGGAAGAGGAGG | |
| | AGGATGAACCTGAGGTTCCTGCCGGACCCCGTCCTCGAAGGATCTCGGAG | |
| | TTGAACATGAAGGAAAAAATTGCCCCCATCCCTGAAGGGAGCGCTTTCTT | |
| | CATTCTTAGCAAGACCAACCCGATCCGCGTAGGCTGCCACAAGCTCATCA | |
| | ACCACCACATCTTCACCAACCTCATCCTTGTCTTCATCATGCTGAGCAGT | |
| | GCTGCCCTGGCCGCAGAGGACCCCATCCGCAGCCACTCCTTCCGGAACAC | |
| | GATACTGGGTTACTTTGACTATGCCTTCACAGCCATCTTTACTGTTGAGA | |
| | TCCTGTTGAAGATGACAACTTTTGGAGCTTTCCTCCACAAAGGGGCCTTC | |
| | TGCAGGAACTACTTCAATTTGCTGGATATGCTGGTGGTTGGGGTGTCTCT | |
| | GGTGTCATTTGGGATTCAATCCAGTGCCATCTCCGTTGTGAAGATTCTGA | |
| | GGGTCTTAAGGGTCCTGCGTCCCCTCAGGGCCATCAACAGAGCAAAAGGA | |
| | CTTAAGCACGTGGTCCAGTGCGTCTTCGTGGCCATCCGGACCATCGGCAA | |

TABLE 1-continued

| Description | Sequence | SEQ ID NO. |
|---|---|---|
| | CATCATGATCGTCACCACCCTCCTGCAGTTCATGTTTGCCTGTATCGGGG | |
| | TCCAGTTGTTCAAGGGGAAGTTCTATCGCTGTACGGATGAAGCCAAAAGT | |
| | AACCCTGAAGAATGCAGGGGACTTTTCATCCTCTACAAGGATGGGGATGT | |
| | TGACAGTCCTGTGGTCCGTGAACGGATCTGGCAAAACAGTGATTTCAACT | |
| | TCGACAACGTCCTCTCTGCTATGATGGCGCTCTTCACAGTCTCCACGTTT | |
| | GAGGGCTGGCCTGCGTTGCTGTATAAAGCCATCGACTCGAATGGAGAGAA | |
| | CATCGGCCCAATCTACAACCACCGCGTGGAGATCTCCATCTTCTTCATCA | |
| | TCTACATCATCATTGTAGCTTTCTTCATGATGAACATCTTTGTGGGCTTT | |
| | GTCATCGTTACATTTCAGGAACAAGGAGAAAAAGAGTATAAGAACTGTGA | |
| | GCTGGACAAAAATCAGCGTCAGTGTGTTGAATACGCCTTGAAAGCACGTC | |
| | CCTTGCGGAGATACATCCCCAAAAACCCCTACCAGTACAAGTTCTGGTAC | |
| | GTGGTGAACTCTTCGCCTTTCGAATACATGATGTTTGTCCTCATCATGCT | |
| | CAACACACTCTGCTTGGCCATGCAGCACTACGAGCAGTCCAAGATGTTCA | |
| | ATGATGCCATGGACATTCTGAACATGGTCTTCACCGGGGTGTTCACCGTC | |
| | GAGATCGTTTTGAAAGTCATCGCATTTAAGCCTAAGGGGTATTTTAGTGA | |
| | CGCCTGGAACACGTTTGACTCCCTCATCGTAATCGGCAGCATTATAGACG | |
| | TGGCCCTCAGCGAAGCAGACAAAATTGTAGCGAACTCTGAAGAGAGCAAT | |
| | AGAATCTCCATCACCTTTTTCCGTCTTTTCCGAGTGATGCGATTGGTGAA | |
| | GCTTCTCAGCAGGGGGAAGGCATCCGGACATTGCTGTGGACTTTTATTA | |
| | AGTTCTTTCAGGCGCTCCCGTATGTGGCCCTCCTCATAGCCATGCTGTTC | |
| | TTCATCTATGCGGTCATTGGCATGCAGATGTTTGGGAAAGTTGCCATGAG | |
| | AGATAACAACCAGATCAATAGGAACAATAACTTCCAGACGTTTCCCCAGG | |
| | CGGTGCTGCTGCTCTTCAGGTGTGCAACAGGTGAGGCCTGGCAGGAGATC | |
| | ATGCTGGCCTGTCTCCCAGGGAAGCTCTGTGACCCTGAGTCAGATTACAA | |
| | CCCCGGGGAGGAGCATACATGTGGGAGCAACTTTGCCATTGTCTATTTCA | |
| | TCAGTTTTTACATGCTCTGTGCATTTCTGATCATCAATCTGTTTCTGGCT | |
| | GTCATCATGGATAATTTCGACTATCTGACCCGGGACTGGTCTATTTTGGG | |
| | GCCTCACCATTTAGATGAATTCAAAAGAATATGGTCAGAATATGACCCTG | |
| | AGGCAAAGGGAAGGATAAAACACCTTGATGTGGTCACTCTGCTTCGACGC | |
| | ATCCAGCCTCCCCTGGGGTTTGGGAAGTTATGTCCACACAGGGTAGCGTG | |
| | CAAGACATTAGTTGCCATGAACATGCCTCTCAACAGTGACGGGACAGTCA | |
| | TGTTTAATGCAACCCTGTTTGCTTTGGTTCGAACGGCTCTTAAGATCAAG | |
| | ACCGAAGGGAACCTGGAGCAAGCTAATGAAGAACTTCGGGCTGTGATAAA | |
| | GAAAATTTGGAAGAAAACCAGCATGAAATTACTTGACCAAGTTGTCCCTC | |
| | CAGCTGGTGATGATGAGGTAACCGTGGGGAAGTTCTATGCCACTTTCCTG | |
| | ATACAGGACTACTTTAGGAAATTCAAGAAACGGAAAGAACAAGGACTGGT | |
| | GGGAAAGTACCCTGCGAAGAACACCACAATTGCCCTACAGGCGGGATTAA | |
| | GGACACTGCATGACATTGGGCCAGAAATCCGGCGTGCTATATCGTGTGAT | |

TABLE 1-continued

| Description | Sequence | SEQ ID NO. |
|---|---|---|
| | TTGCAAGATGACGAGCCTGAGGAAACAAAACGAGAAGAAGAAGATGATGT | |
| | GTTCAAAAGAAATGGTGCCCTGCTTGGAAACCATGTCAATCATGTTAATA | |
| | GTGATAGGAGAGATTCCCTTCAGCAGACCAATACCACCCACCGTCCCCTG | |
| | CATGTCCAAAGGCCTTCAATTCCACCTGCAAGTGATACTGAGAAACCGCT | |
| | GTTTCCTCCAGCAGGAAATTCGGTGTGTCATAACCATCATAACCATAATT | |
| | CCATAGGAAAGCAAGTTCCCACCTCAACAAATGCCAATCTCAATAATGCC | |
| | AATATGTCCAAAGCTGCCCATGGAAAGCGGCCCAGCATTGGGAACCTTGA | |
| | GCATGTGTCTGAAAATGGGCATCATTCTTCCCACAAGCATGACCGGGAGC | |
| | CTCAGAGAAGGTCCAGTGTGAAAAGGTCCGACTCAGGAGATGAACAGCTC | |
| | CCAACTATTTGCCGGGAAGACCCAGAGATACATGGCTATTTCAGGGACCC | |
| | CCACTGCTTGGGGGAGCAGGAGTATTTCAGTAGTGAGGAATGCTACGAGG | |
| | ATGACAGCTCGCCCACCTGGAGCAGGCAAAACTATGGCTACTACAGCAGA | |
| | TACCCAGCCAGAAACATCGACTCTGAGAGGCCCCGAGGCTACCATCATCC | |
| | CCAAGGATTCTTGGAGGACGATGACTCGCCCGTTTGCTATGATTCACGGA | |
| | GATCTCCAAGGAGACGCCTACTACCTCCCACCCCAGCATCCCACCGGAGA | |
| | TCCTCCTTCAACTTTGAGTGCCTGCGCCGGCAGAGCAGCCAGGAAGAGGT | |
| | CCCGTCGTCTCCCATCTTCCCCCATCGCACGGCCCTGCCTCTGCATCTAA | |
| | TGCAGCAACAGATCATGGCAGTTGCCGGCCTAGATTCAAGTAAAGCCCAG | |
| | AAGTACTCACCGAGTCACTCGACCCGGTCGTGGGCCACCCCTCCAGCAAC | |
| | CCCTCCCTACCGGGACTGGACACCGTGCTACACCCCCCTGATCCAAGTGG | |
| | AGCAGTCAGAGGCCCTGGACCAGGTGAACGGCAGCCTGCCGTCCCTGCAC | |
| | CGCAGCTCCTGGTACACAGACGAGCCCGACATCTCCTACCGGACTTTCAC | |
| | ACCAGCCAGCCTGACTGTCCCCAGCAGCTTCCGGAACAAAAACAGCGACA | |
| | AGCAGAGGAGTGCGGACAGCTTGGTGGAGGCAGTCCTGATATCCGAAGGC | |
| | TTGGGACGCTATGCAAGGGACCCAAAATTTGTGTCAGCAACAAAACACGA | |
| | AATCGCTGATGCCTGTGACCTCACCATCGACGAGATGGAGAGTGCAGCCA | |
| | GCACCCTGCTTAATGGGAACGTGCGTCCCCGAGCCAACGGGGATGTGGGC | |
| | CCCCTCTCACACCGGCAGGACTATGAGCTACAGGACTTTGGTCCTGGCTA | |
| | CAGCGACGAAGAGCCAGACCCTGGGAGGGATGAGGAGGACCTGGCGGATG | |
| | AAATGATATGCATCACCACCTTGTAG | |
| amino acid sequence of a novel human $\alpha_{1D}$ calcium channel subunit | MMMMMMMKKMQHQRQQQADHANEANYARGTRLPLSGEGPTSQPNSSKQTV LSWQAAIDAARQAKAAQTMSTSAPPPVGSLSQRKRQQYAKSKKQGNSSNS RPARALFCLSLNNPIRRACISIVEWKPFDIFILLAIFANCVALAIYIPFP EDDSNSTNHNLEKVEYAFLIIFTVETFLKIIAYGLLLHPNAYVRNGWNLL DFVIVIVGLFSVILEQLTKETEGGNHSSGKSGGFDVKALRAFRVLRPLRL VSGVPSLQVVLNSIIKAMVPLLHIALLVLFVIIIYAIIGLELFIGKMHKT CFFADSDIVAEEDPAPCAFSGNGRQCTANGTECRSCWVGPNGGITNFDNF AFAMLTVFQCITMEGWTDVLYWMNDAMGFELPWVYFVSLVIFGSFFVLNL VLGVLSGEFSKEREKAKARGDFQKLREKQQLEEDLKGYLDWITQAEDIDP | SEQ ID NO: 4 |

TABLE 1-continued

| Description | Sequence | SEQ ID NO. |
|---|---|---|
| | ENEEEGGEEGKRNTSMPTSETESVNTENVSGEGENRGCCGSLCQAISKSK | |
| | LSRRWRRWNRFNRRRCRAAVKSVTFYWLVIVLVFLNTLTISSEHYNQPDW | |
| | LTQIQDIANKVLLALFTCEMLVKMYSLGLQAYFVSLFNRFDCFVVCGGIT | |
| | ETILVELEIMSPLGISVFRCVRLLRIFKVTRHWTSLCNLVASLLNSMKSS | |
| | ASLLLLLFLFIIIFSLLGMQLFGGKFNFDETQTKRSTFDNFPQALLTVFQ | |
| | ILTGEDWNAVMYDGIMAYGGPSSSGMIVCIYFIILFICGNYILLNVFLAI | |
| | AVDNLADAESLNTAQKEEAEEKERKKIARKESLENKKNNKPEVNQIANSD | |
| | NKVTIDDYREEDEDKDPYPPCDVPVGEEEEEEEEDEPEVPAGPRPRRISE | |
| | LNMKEKIAPIPEGSAFFILSKTNPIRVGCHKLINHHIFTNLILVFIMLSS | |
| | AALAAEDPIRSHSFRNTILGYFDYAFTAIFTVEILLKMTTFGAFLHKGAF | |
| | CRNYFNLLDMLVVGVSLVSFGIQSSAISVVKILRVLRVLRPLRAINRAKG | |
| | LKHVVQCVFVAIRTIGNIMIVTTLLQFMFACIGVQLFKGKFYRCTDEAKS | |
| | NPEECRGLFILYKDGDVDSPVVRERIWQNSDFNFDNVLSAMMALFTVSTF | |
| | EGWPALLYKAIDSNGENIGPIYNHRVEISIFFIIYIIIVAFFMMNIFVGF | |
| | VIVTFQEQGEKEYKNCELDKNQRQCVEYALKARPLRRYIPKNPYQYKFWY | |
| | VVNSSPFEYMMFVLIMLNTLCLAMQHYEQSKMFNDAMDILNMVFTGVFTV | |
| | EMVLKVIAFKPKGYFSDAWNTFDSLIVIGSIIDVALSEADKIVANSEESN | |
| | RISITFFRLFRVMRLVKLLSRGEGIRTLLWTFIKFFQALPYVALLIAMLF | |
| | FIYAVIGMQMFGKVAMRDNNQINRNNNFQTFPQAVLLLFRCATGEAWQEI | |
| | MLACLPGKLCDPESDYNPGEEHTCGSNFAIVYFISFYMLCAFLIINLFVA | |
| | VIMDNFDYLTRDWSILGPHHLDEFKRIWSEYDPEAKGRIKHLDVVTLLRR | |
| | IQPPLGFGKLCPHRVACKRLVAMNMPLNSDGTVMFNATLFALVRTALKIK | |
| | TEGNLEQANEELRAVIKKIWKKTSMKLLDQVVPPAGDDEVTVGKFYATFL | |
| | IQDYFRKFKKRKEQGLVGKYPAKNTTIALQAGLRTLHDIGPEIRRAISCD | |
| | LQDDEPEETKREEEDDVFKRNGALLGNHVNHVNSDRRDSLQQTNTTHRPL | |
| | HVQRPSIPPASDTEKPLFPPAGNSVCHNHHNHNSIGKQVPTSTNANLNNA | |
| | NMSKAAHGKRPSIGNLEHVSENGHHSSHKHDREPQRRSSVKRSDSGDEQL | |
| | PTICREDPEIHGYFRDPHCLGEQEYFSSEECYEDDSSPTWSRQNYGYYSR | |
| | YPGRNIDSERPRGYHHPQGFLEDDDSPVCYDSRRSPRRRLLPPTPASHRR | |
| | SSFNFECLRRQSSQEEVPSSPIFPHRTALPLHLMQQQIMAVAGLDSSKAQ | |
| | KYSPSHSTRSWATPPATPPYRDWTPCYTPLIQVEQSEALDQVNGSLPSLH | |
| | RSSWYTDEPDISYRTFTPASLTVPSSFRNKNSDKQRSADSLVEAVLISEG | |
| | LGRYARDPKFVSATKHEIADACDLTIDEMESAASTLLNGNVRPRANGDVG | |
| | PLSHRQDYELQDFGPGYSDEEPDPGRDEEDLADEMICITTL | |
| Nucleotide sequence of the coding region of a | ATGATGATGATGATGATGAAAAAAATGCAGCATCAACGGCAGCAGCA AGCGGACCACGCGAACGAGGCAAACTATGCAAGAGGCACCAGACTTCCTC TTTCTGGTGAAGGACCAACTTCTCAGCCGAATAGCTCCAAGCAAACTGTC CTGTCTTGGCAAGCTGCAATCGATGCTGCTAGACAGGCCAAGGCTGCCCA | SEQ ID NO: 5 |

TABLE 1-continued

| Description | Sequence | SEQ ID NO. |
|---|---|---|
| human L-type calcium channel $\alpha_{1D}$ subunit (see also GENBANK® accession number M76558.) | AACTATGAGCACCTCTGCACCCCCACCTGTAGGATCTCTCTCCCAAAGAA<br>AACGTCAGCAATACGCCAAGAGCAAAAAACAGGGTAACTCGTCCAACAGC<br>CGACCTGCCCGCGCCCTTTTCTGTTTATCACTCAATAACCCCATCCGAAG<br>AGCCTGCATTAGTATAGTGGAATGGAAACCATTTGACATATTTATATTAT<br>TGGCTATTTTTGCCAATTGTGTGGCCTTAGCTATTTACATCCCATTCCCT<br>GAAGATGATTCTAATTCAACAAATCATAACTTGGAAAAAGTAGAATATGC<br>CTTCCTGATTATTTTTACAGTCGACACATTTTTGAAGATTATAGCGTATG<br>GATTATTGCTACATCCTAATGCTTATGTTAGGAATGGATGGAATTTACTG<br>GATTTTGTTATAGTAATAGTAGGATTGTTTAGTGTAATTTTGGAACAATT<br>AACCAAAGAAACAGAAGGCGGGAACCACTCAAGCGGCAAATCTGGAGGCT<br>TTGATGTCAAAGCCCTCCGTGCCTTTCGAGTGTTGCGACCACTTCGACTA<br>GTGTCAGGAGTGCCCAGTTTACAAGTTGTCCTGAACTCCATTATAAAAGC<br>CATGGTTCCCCTCCTTCACATAGCCCTTTTGGTATTATTTGTAATCATAA<br>TCTATGCTATTATAGGATTGGAACTTTTTATTGGAAAAATGCACAAAACA<br>TGTTTTTTTGCTGACTCAGATATCGTAGCTGAAGAGGACCCAGCTCCATG<br>TGCGTTCTCAGGGAATGGACGCCAGTGTACTGCCAATGGCACGGAATGTA<br>GGAGTGGCTGGGTTGGCCCGAACCGAGGCATCACCAACTTTGATAACTTT<br>GCCTTTGCCATGCTTACTGTGTTTCAGTGCATCACCATGGAGGGCTGGAC<br>AGACGTGCTCTACTGGATGAATGATGCTATGGGATTTGAATTGCCCTGGG<br>TGTATTTTGTCAGTCTCGTCATCTTTGGGTCATTTTTCGTACTAAATCTT<br>GTACTTGGTGTATTGAGCGGAGAATTCTCAAAGGAAAGAGAGAAGGCAAA<br>AGCACGGGGAGATTTCCAGAAGCTCCGGGAGAAGCAGCAGCTGGAGGAGG<br>ATCTAAAGGGCTACTTGGATTGGATCACCCAAGCTGAGGACATCGATCCG<br>GAGAATGAGGAAGAAGGAGGAGAGGAAGGCAAACGAAATACTAGCATGCC<br>CACCAGCGAGACTGAGTCTGTGAACACAGAGAACGTCAGCGGTGAAGGCG<br>AGAACCGAGGCTGCTGTGGAAGTCTCTGTCAAGCCATCTCAAAATCCAAA<br>CTCAGCCGACGCTGGCGTCGCTGGAACCGATTCAATCGCAGAAGATGTAG<br>CGCCGCCGTGAAGTCTGTCACGTTTTACTGGCTGGTTATCGTCCTGGTGT<br>TTCTGAACACCTTAACCATTTCCTCTGAGCACTACAATCAGCCAGATTGG<br>TTGACACAGATTCAAGATATTGCCAACAAAGTCCTCTTGGCTCTGTTCAC<br>CTGCGAGATGCTGGTAAAAATGTACAGCTTGGGCCTCCAAGCATATTTCG<br>TCTCTCTTTTCAACCGGTTTGATTGCTTCGTGGTGTGTGGTGGAATCACT<br>GAGACGATCTTGGTGGAACTGGAAATCATGTCTCCCCTGGGGATCTCTGT<br>GTTTCGGTGTGTGCGCCTCTTAAGAATCTTCAAAGTGACCAGGCACTGGA<br>CTTCCCTGTGCAACTTAGTGGCATCCTTATTAAACTCCATGAAGTCCAGT<br>GCTTCGCTGTTGCTTCTGCTTTTTCTCTTCATTATCATCTTTTCCTTGCT<br>TGGGATGCAGCTGTTTGGCGGCAAGTTTAATTTTGATGAAACGCAAACCA<br>AGCGGAGCACCTTTGACAATTTCCCTCAAGCACTTCTCACAGTGTTCCAG<br>ATCCTGACAGGCGAAGACTGGAATGCTGTGATGTACGATGGCATCATGGC |

TABLE 1-continued

| Description | Sequence | SEQ ID NO. |
|---|---|---|
| | TTACGGGGCCCATCCTCTTCAGGAATGATCGTCTGCATCTACTTCATCA | |
| | TCCTCTTCATTTGTGGTAACTATATTCTACTGAATGTCTTCTTGGCCATC | |
| | GCTGTAGACAATTTGGCTGATGCTGAAAGTCTGAACACTGCTCAGAAAGA | |
| | AGAAGCGGAAGAAAAGGAGAGGAAAAAGATTGCCAGAAAAGAGAGCCTAG | |
| | AAAATAAAAAGAACAACAAACCAGAAGTCAACCAGATAGCCAACAGTGAC | |
| | AACAAGGTTACAATTGATGACTATAGAGAAGAGGATGAAGACAAGCACCC | |
| | CTATCCGCCTTGCGATGTGCCAGTAGGGGAAGAGGAAGAGGAAGAGGAGG | |
| | AGGATGAACCTGAGGTTCCTGCCGGACCCCGTCCTCGAAGGATCTCGGAG | |
| | TTGAACATGAAGGAAAAAATTGCCCCCATCCCTGAAGGGAGCGCTTTCTT | |
| | CATTCTTAGCAAGACCAACCCGATCCGCGTAGGCTGCCACAAGCTCATCA | |
| | ACCACCACATCTTCACCAACCTCATCCTTGTCTTCATCATGCTGAGCAGT | |
| | GCTGCCCTGGCCGCAGAGGACCCCATCCGCAGCCACTCCTTCCGGAACAC | |
| | GATACTGGCTTACTTTGACTATGCCTTCACAGCCATCTTTACTGTTGAGA | |
| | TCCTGTTGAAGATGACAACTTTTGGAGCTTTCCTCCACAAAGCGGCCTTC | |
| | TGCAGGAACTACTTCAATTTGCTGGATATGCTGGTGGTTGGGGTGTCTCT | |
| | GGTGTCATTTGGGATTCAATCCAGTGCCATCTCCGTTGTGAAGATTCTGA | |
| | GGGTCTTAAGGGTCCTGCGTCCCCTCAGGGCCATCAACAGAGCAAAAGGA | |
| | CTTAAGCACGTGGTCCAGTGCGTCTTCGTGGCCATCCGGACCATCGGCAA | |
| | CATCATGATCGTCACCACCCTCCTGCAGTTCATGTTTGCCTGTATCGGGG | |
| | TCCAGTTGTTCAAGGGGAAGTTCTATCGCTGTACGGATGAAGCCAAAAGT | |
| | AACCCTGAAGAATGCAGGGGACTTTTCATCCTCTACAAGGATGGGGATGT | |
| | TGACAGTCCTGTGGTCCGTGAACGGATCTGGCAAAACAGTGATTTCAACT | |
| | TCGACAACGTCCTCTCTGCTATGATGGCGCTCTTCACAGTCTCCACGTTT | |
| | GAGGGCTGGCCTGCGTTGCTGTATAAAGCCATCGACTCGAATGGAGAGAA | |
| | CATCGGCCCAATCTACAACCACCGCGTGGAGATCTCCATCTTCTTCATCA | |
| | TCTACATCATCATTGTAGCTTTCTTCATGATGAACATCTTTGTGGGCTTT | |
| | GTCATCGTTACATTTCAGGAACAAGGAGAAAAAGAGTATAAGAACTGTGA | |
| | GCTGGACAAAAATCAGCGTCAGTGTGTTGAATACGCCTTGAAAGCACGTC | |
| | CCTTGCGGAGATACATCCCCAAAAACCCCTACCAGTACAAGTTCTGGTAC | |
| | GTGGTGAACTCTTCGCCTTTCGAATACATGATGTTTGTCCTCATCATGCT | |
| | CAACACACTCTGCTTGGCCATGCAGCACTACGAGCAGTCCAAGATGTTCA | |
| | ATGATGCCATGGACATTCTGAACATGGTCTTCACCGGGGTGTTCACCGTC | |
| | GAGATGGTTTTGAAAGTCATCGCATTTAAGCCTAAGGGGTATTTTAGTGA | |
| | CGCCTGGAACACGTTTGACTCCCTCATCGTAATCGGCAGCATTATAGACG | |
| | TGGCCCTCAGCGAAGCAGACCCAACTGAAAGTGAAAATGTCCCTGTCCCA | |
| | ACTGCTACACCTGGGAACTCTGAAGAGAGCAATAGAATCTCCATCACCTT | |
| | TTTCCGTCTTTTCCGAGTGATGCGATTGGTGAAGCTTCTCAGCAGGGGGG | |
| | AAGGCATCCGGACATTGCTGTGGACTTTTATTAAGTTCTTTCAGGCGCTC | |

TABLE 1-continued

| Description | Sequence | SEQ ID NO. |
|---|---|---|
| | CCGTATGTGGCCCTCCTCATAGCCATGCTGTTCTTCATCTATGCGGTCAT | |
| | TGGCATGCAGATGTTTGGGAAAGTTGCCATGAGAGATAACAACCAGATCA | |
| | ATAGGAACAATAACTTCCAGACGTTTCCCCAGGCGGTGCTGCTGCTCTTC | |
| | AGGTGTGCAACAGGTGAGGCCTGCCAGGAGATCATGCTGGCCTGTCTCCC | |
| | AGGGAAGCTCTGTGACCCTGAGTCAGATTACAACCCCGGGGAGGAGCATA | |
| | CATGTGGGAGCAACTTTGCCATTGTCTATTTCATCAGTTTTTACATGCTC | |
| | TGTGCATTTCTGATCATCAATCTGTTTGTGGCTGTCATCATGGATAATTT | |
| | CGACTATCTGACCCGGGACTGGTCTATTTTGGGGCCTCACCATTTAGATG | |
| | AATTCAAAAGAATATGGTCAGAATATGACCCTGAGGCAAAGGGAAGGATA | |
| | AAACACCTTGATGTGGTCACTCTGCTTCGACGCATCCAGCCTCCCCTGGG | |
| | GTTTGGGAAGTTATGTCCACACAGGGTAGCGTGCAAGAGATTAGTTGCCA | |
| | TGAACATGCCTCTCAACAGTGACGGGACAGTCATGTTTAATGCAACCCTG | |
| | TTTGCTTTGGTTCGAACGGCTCTTAAGATCAAGACCGAAGGGAACCTGGA | |
| | GCAAGCTAATGAAGAACTTCGGGCTGTGATAAAGAAAATTTGGAAGAAAA | |
| | CCAGCATGAAATTACTTGACCAAGTTGTCCCTCCAGCTGGTGATGATGAG | |
| | GTAACCGTGGGGAAGTTCTATGCCACTTTCCTGATACAGGACTACTTTAG | |
| | GAAATTCAAGAAACGGAAAGAACAAGGACTGGTGGGAAAGTACCCTGCGA | |
| | AGAACACCACAATTGCCCTACAGGCGGGATTAAGGACACTGCATGACATT | |
| | GGGCCAGAAATCCGGCGTGCTATATCGTGTGATTTGCAAGATGACGAGCC | |
| | TGAGGAAACAAAACGAGAAGAAGAAGATGATGTGTTCAAAAGAAATGGTG | |
| | CCCTGCTTGGAAACCATGTCAATCATGTTAATAGTGATAGGAGAGATTCC | |
| | CTTCAGCAGACCAATACCACCCACCGTCCCCTGCATGTCCAAAGGCCTTC | |
| | AATTCCACCTGCAAGTGATACTGAGAAACCGCTGTTTCCTCCAGCAGGAA | |
| | ATTCGGTGTGTCATAACCATCATAACCATAATTCCATAGGAAAGCAAGTT | |
| | CCCACCTCAACAAATGCCAATCTCAATAATGCCAATATGTCCAAAGCTGC | |
| | CCATGGAAAGCGGCCCAGCATTGGGAACCTTGAGCATGTGTCTGAAAATG | |
| | GGCATCATTCTTCCCACAAGCATGACCGGGAGCCTCAGAGAAGGTCCAGT | |
| | GTGAAAACAACCCGCTATTATGAAACTTACATTAGGTCCGACTCAGGAGA | |
| | TGAACAGCTCCCAACTATTTGCCGGGAAGACCCAGAGATACATGGCTATT | |
| | TCAGGGACCCCCACTGCTTGGGGGAGCAGGAGTATTTCAGTAGTGAGGAA | |
| | TGCTACGAGGATGACAGCTCGCCCACCTGGAGCAGGCAAAACTATGGCTA | |
| | CTACAGCAGATACCCAGGCAGAAACATCGACTCTGAGAGGCCCCGAGGCT | |
| | ACCATCATCCCCAAGGATTCTTGGAGGACGATGACTCGCCCGTTTGCTAT | |
| | GATTCACGGAGATCTCCAAGGAGACGCCTACTACCTCCCACCCCAGCATC | |
| | CCACCGCAGATCCTCCTTCAACTTTGAGTGCCTGCGCCGGCACAGCAGCC | |
| | AGGAAGAGGTCCCGTCGTCTCCCATCTTCCCCATCGCACGGCCCTGCCT | |
| | CTGCATCTAATGCAGCAACAGATCATGGCAGTTGCCGGCCTAGATTCAAG | |
| | TAAAGCCCAGAAGTACTCACCGAGTCACTCGACCCGGTCGTGGGCCACCC | |
| | CTCCAGCAACCCCTCCCTACCGGGACTGGACACCGTGCTACACCCCCCTG | |

TABLE 1-continued

| Description | Sequence | SEQ ID NO. |
|---|---|---|
| | ATCCAAGTGGAGCAGTCAGAGGCCCTGGACCAGGTGAACGGCAGCCTGCC | |
| | GTCCCTGCACCGCAGCTCCTGGTACACAGACGAGCCCGACATCTCCTACC | |
| | GGACTTTCACACCAGCCAGCCTGACTGTCCCCAGCAGCTTCCGGAACAAA | |
| | AACAGCGACAAGCAGAGGAGTGCGGACAGCTTGGTGGAGGCAGTCCTGAT | |
| | ATCCGAAGGCTTGGGACGCTATGCAAGGGACCCAAAATTTGTGTCAGCAA | |
| | CAAAACACGAAATCGCTGATGCCTGTGACCTCACCATCGACGAGATGGAG | |
| | AGTGCAGCCAGCACCCTGCTTAATGGGAACGTGCGTCCCCGAGCCAACGG | |
| | GGATGTGGGCCCCCTCTCACACCGGCAGGACTATGAGCTACAGGACTTTG | |
| | GTCCTGGCTACAGCGACGAAGAGCCAGACCCTGGGAGGGATGAGGAGGAC | |
| | CTGGCGGATGAAATGATATGCATCACCACCTTGTAG | |
| Amino acid sequence of a human L-type calcium channel α<sub>1D</sub> subunit (see also GENBANK® accession number Q01668.) | MMMMMMMKKMQHQRQQQADHANEANYARGTRLPLSGEGPTSQPNSSKQTV LSWQAAIDAARQAKAAQTMSTSAPPPVGSLSQRKRQQYAKSKKQGNSSNS RPARALFCLSLNNPIRRACISIVEWKPFDIFILLAIFANCVALAIYIPFP EDDSNSTNHNLEKVEYAFLIIFTVETFLKIIAYGLLLHPNAYVRNGWNLL DFVIVIVGLFSVILEQLTKETEGGNHSSGKSGGFDVKALRAFRVLRPLRL VSGVPSLQVVLNSIIKAMVPLLHIALLVLFVIIIYAIIGLELFIGKMHKT CFFADSDIVAEEDPAPCAFSGNGRQCTANGTECRSGWVGPNGGITNFDNF AFAMLTVFQCITMEGWTDVLYWMNDAMGFELPWVYFVSLVIFGSFFVLNL VLGVLSGEFSKEREKAKARGDFQKLREKQQLEEDLKGYLDWITQAEDIDP ENEEEGGEEGKRNTSMPTSETESVNTENVSGEGENRGCCGSLCQAISKSK LSRRWRRWNRFNRRRCRAAVKSVTFYWLVIVLVFLNTLTISSEHYNQPDW LTQIQDIANKVLLALFTCEMLVKMYSLGLQAYFVSLFNRFDCFVVCGGIT ETILVELEIMSPLGISVFRCVRLLRIFKVTRHWTSLCNLVASLLNSMKSS ASLLLLLFLFIIIFSLLGMQLFGGKFNFDETQTKRSTFDNFPQALLTVFQ ILTGEDWNAVMYDGIMAYGGPSSSGMIVCIYFIILFICGNYILLNVFLAI AVDNLADAESLNTAQKEEAEEKERKKIARKESLENKKNNKPEVNQIANSD NKVTIDDYREEDEDKDPYPPCDVPVGEEEEEEEEDEPEVPAGPRPRRISE LNMKEKIAPIPEGSAFFILSKTNPIRVGCHKLINHHIFTNLILVFIMLSS AALAAEDPIRSHSFRNTILGYFDYAFTAIFTVEILLKMTTFGAFLHKGAF CRNYFNLLDMLVVGVSLVSFGIQSSAISVVKILRVLRVLRPLRAINRAKG LKHVVQCVFVAIRTIGNIMIVTTLLQFMFACIGVQLFKGKFYRCTDEAKS NPEECRGLFILYKDGDVDSPVVRERIWQNSDFNFDNVLSAMMALFTVSTF EGWPALLYKAIDSNGENIGPIYNHRVEISIFFIIYIIIVAFFMMNIFVGF VIVTFQEQGEKEYKNCELDKNQRQCVEYALKARPLRRYIPKNPYQYKFWY VVNSSPFEYMMFVLIMLNTLCLAMQHYEQSKMFNDAMDILNMVFTGVFTV EMVLKVIAFKPKGYFSDAWNTFDSLIVIGSIIDVALSEADPTESENVPVP TATPGNSEESNRISITFFRLFRVMRLVKLLSRGEGIRTLLWTFIKFFQAL PYVALLIAMLFFIYAVIGMQMFGKVAMRDNNQINRNNNFQTFPQAVLLLF | SEQ ID NO: 6 |

TABLE 1-continued

| Description | Sequence | SEQ ID NO. |
|---|---|---|
| | RCATGEAWQEIMLACLPGKLCDPESDYNPGEEHTCGSNFAIVYFISFYML | |
| | CAFLIINLFVAVIMDNFDYLTRDWSILGPHHLDEFKRIWSEYDPEAKGRI | |
| | KHLDVVTLLRRIQPPLGFGKLCPHRVACKRLVAMNMPLNSDGTVMFNATL | |
| | FALVRTALKIKTEGNIEQANEELRAVIKKIWKKTSMKLLDQVVPPAGDDE | |
| | VTVGKFYATFLIQDYFRKFKKRKEQGLVGKYPAKNTTIALQAGLRTLHDI | |
| | GPEIRRAISCDLQDDEPEETKREEEDDVFKRNGALLGNHVNHVNSDRRDS | |
| | LQQTNTTHRPLHVQRPSIPPASDTEKPLFPPAGNSVCHNHHNHNSIGKQV | |
| | PTSTNANLNNANMSKAAHGKRPSIGNLEHVSENGHHSSHKHDREPQRRSS | |
| | VKRTRYYETYIRSDSGDEQLPTICREDPEIHGYFRDPHCLGEQEYFSSEE | |
| | CYEDDSSPTWSRQNYGYYSRYPGRNIDSERPRGYHHPQGFLEDDDSPVCY | |
| | DSRRSPRRRLLPPTPASHRRSSFNFECLRRQSSQEEVPSSPIFPHRTALP | |
| | LHLMQQQIMAVAGLDSSKAQKYSPSHSTRSWATPPATPPYRDWTPCYTPL | |
| | IQVEQSEALDQVNGSLPSLHRSSWYTDEPDISYRTFTPASLTVPSSFRNK | |
| | NSDKQRSADSLVEAVLISEGLGRYARDPKFVSATKHEIADACDLTIDEME | |
| | SAASTLLNGNVRPRANGDVGPLSHRQDYELQDFGPGYSDEEPDPGRDEED | |
| | LADEMICITTL | |
| nucleotides 3871-3915 of SEQ ID NO: 5 | CCAACTGAAAGTGAAAATGTCCCTGTCCCAACTGCTACACCTGGG | SEQ ID NO: 7 |
| amino acids 1291-1305 of SEQ ID NO: 6 | PTESENVPVPTATPG | SEQ ID NO: 8 |
| base pairs 5409-5435 of SEQ ID NO: 5 | AACCCGCTATTATGAAACTTACATTAG | SEQ ID NO: 9 |
| amino acids 1804-1812 of SEQ ID NO: 6 | TRYYETYIR | SEQ ID NO: 10 |

All references cited herein, whether in print, electronic, computer readable storage media or other form, are expressly incorporated by reference in their entirety, including but not limited to, abstracts, articles, journals, publications, texts, treatises, internet web sites, databases, software packages, patents, and patent publications. A number of embodiments of the invention have been described. Nevertheless, it will be understood that various modifications may be made without departing from the spirit and scope of the invention. Accordingly, other embodiments are within the scope of the following claims.

What is claimed is:

1. An isolated L-type calcium channel α1$_{D\text{-}KIVA}$ subunit polypeptide, wherein the polypeptide comprises the amino acid sequence of SEQ ID NO: 4.

2. The polypeptide of claim 1, wherein the polypeptide consists of the amino acid sequence of SEQ ID NO: 4.

3. An isolated L-type calcium channel α1$_{D\text{-}KIVA}$ subunit polypeptide, wherein the polypeptide comprises an amino acid sequence that is at least 95% identical to SEQ ID NO: 4, and wherein the polypeptide comprises the following features: (a) a deletion of amino acids 1291-1305 of SEQ ID NO: 6; (b) an insertion of SEQ ID NO:2; and (c) a deletion of amino acids 1804-1812 of SEQ IL) NO: 6; and wherein the polypeptide has calcium channel α subunit activity.

* * * * *